US006686176B2

(12) United States Patent
Beasley et al.

(10) Patent No.: US 6,686,176 B2
(45) Date of Patent: Feb. 3, 2004

(54) ISOLATED HUMAN KINASE PROTEINS, NUCLEIC ACID MOLECULES ENCODING HUMAN KINASE PROTEINS, AND USES THEREOF

(75) Inventors: Ellen M. Beasley, Darnestown, MD (US); Jane Ye, Boyds, MD (US); Chunhua Yan, Boyds, MD (US); Karen A. Ketchum, Germantown, MD (US); Valentina Di Francesco, Rockville, MD (US)

(73) Assignee: Applera Corporation, Norwalk, CT (US)

( * ) Notice: Subject to any disclaimer, the term of this patent is extended or adjusted under 35 U.S.C. 154(b) by 95 days.

(21) Appl. No.: 09/819,607

(22) Filed: Mar. 29, 2001

(65) Prior Publication Data

US 2003/0022337 A1 Jan. 30, 2003

Related U.S. Application Data

(60) Provisional application No. 60/263,162, filed on Jan. 23, 2001.

(51) Int. Cl.[7] .......................... C12P 21/06; C12N 15/63; C07H 21/04
(52) U.S. Cl. .................. 435/69.1; 435/320.1; 435/91.4; 435/325; 435/455; 536/23.1; 536/23.2; 536/23.5
(58) Field of Search .............................. 536/23.1, 23.2, 536/23.5; 435/320.1, 69.1, 91.4, 325, 455

(56) References Cited

U.S. PATENT DOCUMENTS

2002/0034780 A1 * 3/2002 Myers et al. .............. 435/69.1

FOREIGN PATENT DOCUMENTS

| WO | WO 00/73469 | * 12/2000 |
| WO | WO 01/53312 a1 | * 7/2002 |

OTHER PUBLICATIONS

Russell et al. Structural features can be unconserved in proteins with similar folds pp. 332 350 1994.*

Go hunting in sequence databases but watch out for the traps pp. 425–434 1996.*

Roberts Evolution and orthology of hedgehog genes pp. 496–497 1996.*

Bork Powers and pitfalls in sequence analysis: The 70% hurdle 398–400 1997.*

Ngo et al. Computational complexity, protein structure prediction, and the levinthal paradox pp. 491–495 1994.*

Results of BLAST search of SEQ ID No:2 against Derwent (FastAlert and GeneSeqP) and NCBI (pataa) protein patent databases on Jun. 26, 2003.

* cited by examiner

*Primary Examiner*—Dave T. Nguyen
(74) *Attorney, Agent, or Firm*—Celera Genomics; Justin D. Karjala

(57) ABSTRACT

The present invention provides amino acid sequences of peptides that are encoded by genes within the human genome, the kinase peptides of the present invention. The present invention specifically provides isolated peptide and nucleic acid molecules, methods of identifying orthologs and paralogs of the kinase peptides, and methods of identifying modulators of the kinase peptides.

19 Claims, 16 Drawing Sheets

```
   1 CGAGTGCGCT GCTGAGTCCT GTAGATAAAG CCGCCAACCC CGGGGACTGG
  51 TGTCTCCTGA GTGACCGTGC AGCCGTGGGC GCCATAGAAA GCAGAGAAGG
 101 CAGTGAACTT CGACCACTTC CAGATCCTTC GGGCCATTGG GAAGGGCAGC
 151 TTTGGCAAGG TGTGCATTGT GCAGAAGCGG GACACGGAGA AGATGTACGC
 201 CATGAAGTAC ATGAACAAGC AGCAGTGCAT CGAGCGCGAC GAGGTCCGCA
 251 ACGTCTTCCG GGAGCTGGAG ATCCTGCAGG AGATCGAGCA CGTCTTCCTG
 301 GTGAACCTCT GGTACTCCTT CCAGGACGAG GAGGACATGT TCATGGTCGT
 351 GGACCTGCTA CTGGGCGGGG ACCTGCGCTA CCACCTGCAG CAGAACGTGC
 401 AGTTCTCCGA GGACACGGTG AGGCTGTACA TCTGCGAGAT GGCACTGGCT
 451 CTGGACTACC TGCGCGGCCA GCACATCATC CACAGAGATG TCAAGCCTGA
 501 CAACATTCTC CTGGATGAGA GAGGACATGC ACACCTGACC GACTTCAACA
 551 TTGCCACCAT CATCAAGGAC GGGGAGCGGG CGACGGCATT AGCAGGCACC
 601 AAGCCGTACA TGGCTTCCGGA GATCTTCCAC TCTTTTGTCA ACGGCGGGAC
 651 CGGCTACTCC TTCGAGGTGG ACTGGTGGTC GGTGGGGGTG ATGGCCTATG
 701 AGCTGCTGCG AGGATGGAGG CCCTATGACA TCCACTCCAG CAACGCCGTG
 751 GAGTCCCTGG TGCAGCTGTT CAGCACCGTG AGCGTCCAGT ATGTCCCCAC
 801 GTGGTCCAAG GAGATGGTGG CCTTGCTGCG GAAGCTCCTC ACTGTGAACC
 851 CCGAGCACCG GCTCTCCAGC CTCCAGGACG TGCAGGCAGC CCCGGCGCTG
 901 GCCGGCGTGC TGTGGGACCA CCTGAGCGAG AAGAGGGTGG AGCCGGGCTT
 951 CGTGCCCAAC AAAGGCCGTC TGCACTGCGA CCCCACCTTT GAGCTGGAGG
1001 AGATGATCCT GGAGTCCAGG CCCCTGCACA AGAAGAAGAA GCGCCTGGCC
1051 AAGAACAAGT CCCGGGACAA CAGCAGGGAC AGCTCCCAGT CCGAGAATGA
1101 CTATCTTCAA GACTGCCTCG ATGCCATCCA GCAAGACTTC GTGATTTTTA
1151 ACAGAGAAAA GCTGAAGAGG AGCCAGGACC TCCCGAGGGA GCCTCTCCCC
1201 GCCCCTGAGT CCAGGGATGC TGCGGAGCCT GTGGAGGACG AGGCGGAACG
1251 CTCCGCCCTG CCCATGTGCG GCCCCATTTG CCCCTCGGCC GGGAGCGGCT
1301 AGGCCGGGAC GCCCGTGGTC CTCACCCCTT GAGCTGCTTT GGAGACTCGG
1351 CTGCCAGAGG GAGGGCCATG GGCCGAGGCC TGGCATTCAC GTTCCCACCC
1401 AGCCTGGCTG GCGGTGCCCA CAGTGCCCCG GACACATTTC ACACCTCAGG
1451 CTCGTGGTGG TGCAGGGGAC AAGAGGCTGT GGGTGCAGGG GACACCTGTG
1501 GAGGGCATTT CCCGTGGGCC CCCGAGACCC GCCTAGATGG AGGAAGCGCT
1551 GCTGGGCGCC CTCTTACCGC TCACGGGGAG CTGGGGCCAT GGATGGGACA
1601 GGAGTCTTTG TCCCTGCTCA GCCCGGAGGC TGTGCACGGC CCTCGTCACA
1651 AGGTGACCCT TGCAGCACAG GCCGCGGGTG CCCCAGGCTC GGCTCAGTTC
1701 TTGGAGGTCA AGGGCATGGG TTGGGGTAGT GGGTGGGGAG GTGAATGTTT
1751 TCTAGAGATT CAAACTGCTC CAGCAATTTC TGTATAGTTT TCACCTCTGA
1801 GAATTACAAT GTGAGAACCG CACAAAAAAA AAAAAAAAAA AAAAAAAAAA
1851 AAAAAAAAAA AAAA
     (SEQ ID NO: 1)
```

FEATURES:
5'UTR:        1 - 192
Start Codon:  193
Stop Codon:   1300
3'UTR:        1303

Homologous proteins:
Top 10 BLAST Hits:

```
                                                              Score    E
Sequences producing significant alignments:                   (bits)   Value
CRA|103000001515936 /altid=gi|10946600 /def=ref|NP_067277.1| hy...   760    0.0
CRA|120000042903164 /altid=gi|13358640 /def=dbj|BAB33045.1| (AB...   733    0.0
CRA|87000000001314  /altid=gi|8923754  /def=ref|NP_060871.1| gene... 556    e-157
CRA|87000000001426  /altid=gi|7161864  /def=emb|CAB76566.1| (AJ25... 554    e-156
CRA|108000024647823 /altid=gi|12730486 /def=ref|XP_003392.2| ge...   423    e-117
CRA|18000005184360  /altid=gi|7505957  /def=pir||T23688 hypotheti... 335    1e-90
CRA|18000005004115  /altid=gi|1730069  /def=sp|P54644|KRAC_DICDI ... 217    4e-55
CRA|18000004912236  /altid=gi|464395   /def=sp|P28178|PK2_DICDI PR... 203   8e-51
CRA|18000004910302  /altid=gi|1170689  /def=sp|P42818|KPK1_ARATH ... 202    1e-50
CRA|89000000197925  /altid=gi|7295638  /def=gb|AAF50945.1| (AE003... 201    2e-50
```

FIGURE 1A

EST:

Sequences producing significant alignments:
gi|13032240 /dataset=dbest /taxon=960...
gi|6588496 /dataset=dbest /taxon=9606 ...
gi|883123 /dataset=dbest /taxon=9606 /...
gi|946492 /dataset=dbest /taxon=9606 /...

```
Score      E
(bits)   Value
1348     0.0
1021     0.0
 702     0.0
 236     1e-59
```

EXPRESSION INFORMATION FOR MODULATORY USE:
gi|13032240 prostate
gi|6588496 /lung
gi|883123 /whole brain
gi|946492 / Adult brain Tissue Expression
Whole brain

FIGURE 1B

```
  1 MYAMKYMNKQ QCIERDEVRN VFRELEILQE IEHVFLVNLW YSFQDEEDMF
 51 MVVDLLLGGD LRYHLQQNVQ FSEDTVRLYI CEMALALDYL RGQHIIHRDV
101 KPDNILLDER GHAHLTDFNI ATIIKDGERA TALAGTKPYM APEIFHSFVN
151 GGTGYSFEVD WWSVGVMAYE LLRGWRPYDI HSSNAVESLV QLFSTVSVQY
201 VPTWSKEMVA LLRKLLTVNP EHRLSSLQDV QAAPALAGVL WDHLSEKRVE
251 PGFVPNKGRL HCDPTFELEE MILESRPLHK KKKRLAKNKS RDNSRDSSQS
301 ENDYLQDCLD AIQQDFVIFN REKLKRSQDL PREPLPAPES RDAAEPVEDE
351 AERSALPMCG PICPSAGSG
    (SEQ ID NO: 2)
```

FEATURES:
Functional domains and key regions:
[1] PDOC00001 PS00001 ASN_GLYCOSYLATION
N-glycosylation site 288-291 NKSR

---

[2] PDOC00005 PS00005 PKC_PHOSPHO_SITE
Protein kinase C phosphorylation site

Number of matches: 2
    1     75-77 TVR
    2   245-247 SEK

---

[3] PDOC00006 PS00006 CK2_PHOSPHO_SITE
Casein kinase II phosphorylation site

Number of matches: 4
    1     42-45 SFQD
    2   226-229 SLQD
    3   298-301 SQSE
    4   300-303 SEND

---

[4] PDOC00008 PS00008 MYRISTYL
N-myristoylation site 152-157 GTGYSF

---

[5] PDOC00100 PS00108 PROTEIN_KINASE_ST
Serine/Threonine protein kinases active-site signature 95-107 IIHRDVKPDNILL Membrane spanning structure and domains:

| Helix | Begin | End | Score | Certainty |
|---|---|---|---|---|
| 1 | 185 | 205 | 0.727 | Putative |

FIGURE 2A

BLAST Alignment to Top Hit:

>CRA|103000001515936 /altid=gi|10946600 /def=ref|NP_067277.1|
    hypothetical serine/threonine protein kinase [Mus
    musculus] /org=Mus musculus /taxon=10090 /dataset=nraa
    /length=488
            Length = 488

Score = 760 bits (1942), Expect = 0.0
 Identities = 371/399 (92%), Positives = 381/399 (94%), Gaps = 1/399 (0%)
 Frame = +1

Query: 103   VNFDHFQILRAIGKGSFGKVCIVQKRDTEKMYAMKYMNKQQCIERDEVRNVFRELEILQE 282
             VNFDHFQILRAIGKGSFGKVCIVQKRDTEKMYAMKYMNKQQCIERDEVRNVFRELEILQE
Sbjct: 89    VNFDHFQILRAIGKGSFGKVCIVQKRDTEKMYAMKYMNKQQCIERDEVRNVFRELEILQE 148

Query: 283   IEHVFLVNLWYSFQDEEDMFMVVDLLLGGDLRYHLQQNVQFSEDTVRLYICEMALALDYL 462
             IEHVFLVNLWYSFQDEEDMFMVVDLLLGGDLRYHLQQNVQFSEDTVRLYICEMALALDYL
Sbjct: 149   IEHVFLVNLWYSFQDEEDMFMVVDLLLGGDLRYHLQQNVQFSEDTVRLYICEMALALDYL 208

Query: 463   RGQHIIHRDVKPDNILLDERGHAHLTDFNIATIIKDGERATALAGTKPYMAPEIFHSFVN 642
             R QHIIHRDVKPDNILLDE+GHAHLTDFNIATIIKDGERATALAGTKPYMAPEIFHSFVN
Sbjct: 209   RSQHIIHRDVKPDNILLDEQGHAHLTDFNIATIIKDGERATALAGTKPYMAPEIFHSFVN 268

Query: 643   GGTGYSFEVDWWSVGVMAYELLRGWRPYDIHSSNAVESLVQLFSTVSVQYVPTWSKEMVA 822
             GGTGYSFEVDWWSVGVMAYELLRGWRPYDIHSSNAVESLVQLFSTVSVQYVPTWSKEMVA
Sbjct: 269   GGTGYSFEVDWWSVGVMAYELLRGWRPYDIHSSNAVESLVQLFSTVSVQYVPTWSKEMVA 328

Query: 823   LLRKLLTVNPEHRLSSLQDVQAAPALAGVLWDHLSEKRVEPGFVPNKGRLHCDPTFELEE 1002
             LLRKLLTVNPEHR SSLQD+Q AP+LA VLWD LSEK+VEPGFVPNKGRLHCDPTFELEE
Sbjct: 329   LLRKLLTVNPEHRFSSLQDMQTAPSLAHVLWDDLSEKKVEPGFVPNKGRLHCDPTFELEE 388

Query: 1003  MILESRPLHKKKKRLAKNKSRDNSRDSSQSENDYLQDCLDAIQQDFVIFNREKLKRSQDL 1182
             MILESRPLHKKKKRLAKNKSRD+SRDSSQSENDYLQDCLDAIQQDFVIFNREKLKRSQ+L
Sbjct: 389   MILESRPLHKKKKRLAKNKSRDSSRDSSQSENDYLQDCLDAIQQDFVIFNREKLKRSQEL 448

Query: 1183  PREPLPAPESRDAAEPVED-EAERSALPMCGPICPSAGS 1296
             EP P PE+ D  +    D EAE +ALPMCG ICPS+GS
Sbjct: 449   MSEPPPGPETSDMTDSTADSEAEPTALPMCGSICPSSGS 487 (SEQ ID NO: 4)

>CRA|120000042903164 /altid=gi|13358640 /def=dbj|BAB33045.1|
    (AB056389) hypothetical protein [Macaca fascicularis]
    /org=Macaca fascicularis /taxon=9541 /dataset=nraa
    /length=368
            Length = 368

Score = 733 bits (1872), Expect = 0.0
 Identities = 358/369 (97%), Positives = 361/369 (97%)
 Frame = +1

Query: 193   MYAMKYMNKQQCIERDEVRNVFRELEILQEIEHVFLVNLWYSFQDEEDMFMVVDLLLGGD 372
             MYAMKYMNKQQCIERDEVRNVFREL ILQEIEHVFLVNLWYSFQDEEDMFMVVDLLLGGD
Sbjct: 1     MYAMKYMNKQQCIERDEVRNVFRELGILQEIEHVFLVNLWYSFQDEEDMFMVVDLLLGGD 60

Query: 373   LRYHLQQNVQFSEDTVRLYICEMALALDYLRGQHIIHRDVKPDNILLDERGHAHLTDFNI 552
             LRYHLQQNVQFSEDTVRLYICEMALALDYL GQHIIHRDVKPDNILLDERGHAHLTDFNI
Sbjct: 61    LRYHLQQNVQFSEDTVRLYICEMALALDYLCGQHIIHRDVKPDNILLDERGHAHLTDFNI 120

Query: 553   ATIIKDGERATALAGTKPYMAPEIFHSFVNGGTGYSFEVDWWSVGVMAYELLRGWRPYDI 732
             ATIIKDGERATALAGTKPYMAPEIFHSFVNGGTGYSFEVDWWS+GVMAYELLRGWRPYDI
Sbjct: 121   ATIIKDGERATALAGTKPYMAPEIFHSFVNGGTGYSFEVDWWSLGVMAYELLRGWRPYDI 180

Query: 733   HSSNAVESLVQLFSTVSVQYVPTWSKEMVALLRKLLTVNPEHRLSSLQDVQAAPALAGVL 912
             HSSNAVESLVQLFSTVSVQYVPTWS+EMVALLRKLLTVNPEHR SSLQDVQAAPALAGVL
Sbjct: 181   HSSNAVESLVQLFSTVSVQYVPTWSREMVALLRKLLTVNPEHRFSSLQDVQAAPALAGVL 240

Query: 913   WDHLSEKRVEPGFVPNKGRLHCDPTFELEEMILESRPLHKKKKRLAKNKSRDNSRDSSQS 1092
             W HLSEKRVEP FVPNKGRLHCDPTFELEEMILESRPLHKKKKRLAKNKSRDNSRDSSQS
Sbjct: 241   WGHLSEKRVEPDFVPNKGRLHCDPTFELEEMILESRPLHKKKKRLAKNKSRDNSRDSSQS 300

FIGURE 2B

```
Query: 1093 ENDYLQDCLDAIQQDFVIFNREKLKRSQDLPREPLPAPESRDAAEPVEDEAERSALPMCG 1272
             ENDYLQDCLDAIQQDFVIFNREKLKRSQDLP EPLPAPE RDAAEPVEDE E+SALPMCG
Sbjct:  301  ENDYLQDCLDAIQQDFVIFNREKLKRSQDLPSEPLPAPEPRDAAEPVEDE-EQSALPMCG 359

Query: 1273 PICPSAGSG 1299
             PICPSAGSG
Sbjct:  360  PICPSAGSG 368 (SEQ ID NO: 5)

Hmmer search results (Pfam):
Scores for sequence family classification (score includes all domains):
Model     Description                                      Score    E-value  N
-------   -----------                                      -----    -------  ---
PF00069   Eukaryotic protein kinase domain                 197.7    1.8e-55  1
CE00359   E00359 bone_morphogenetic_protein_receptor         9.8      0.044  1
CE00022   CE00022 MAGUK_subfamily_d                          9.2      0.013  1
CE00031   CE00031 VEGFR                                      1.6      1.3    1
CE00292   CE00292 PTK_membrane_span                        -92.7      0.0016 1
CE00291   CE00291 PTK_fgf_receptor                        -116.1      0.041  1
CE00287   CE00287 PTK_Eph_orphan_receptor                 -125.0      2.8    1
CE00286   E00286 PTK_EGF_receptor                         -131.8      0.0056 1
CE00290   CE00290 PTK_Trk_family                          -206.7      0.58   1
CE00016   CE00016 GSK_glycogen_synthase_kinase             -248.2      0.0061 1

Parsed for domains:
Model     Domain  seq-f seq-t    hmm-f hmm-t      score    E-value
-------   ------  ----- -----    ----- -----      -----    -------
CE00022    1/1      86   107 ..    133   154 ..      9.2     0.013
CE00359    1/1      95   144 ..    272   326 ..      9.8     0.044
CE00031    1/1      79   171 ..   1051  1141 ..      1.6     1.3
CE00286    1/1       3   212 ..      1   263 []   -131.8     0.0056
CE00287    1/1       7   212 ..      1   260 []   -125.0     2.8
CE00290    1/1       4   215 ..      1   282 []   -206.7     0.58
PF00069    1/1       2   228 ..     26   271 ..    197.7     1.8e-55
CE00292    1/1       5   233 ..      1   288 []    -92.7     0.0016
CE00291    1/1       1   233 [.      1   285 []   -116.1     0.041
CE00016    1/1       1   303 [.      1   433 []   -248.2     0.0061
```

FIGURE 2C

```
   1 GATGGAGCCC AGGCCACATG CTTGGGAAAG CGGGTGGTCC TGGGTGAGCC
  51 TGTCTGGCAG GAGGGTGAGG TCCTGTCTGG AGTAGACACC CGGTCTGTGT
 101 CCGCCGCACA TGTGACAGGG CCCAGAGGGC ACGGGAAGCC CAGGTGCCCT
 151 GTCCCCTGGT GAGTGGGCTG TGGGGGTTGA GCACCCCAAG GGAAGGCGTG
 201 TTCTTCCAGA GATTCCCCCG TAAGAGCTGA GCTGCATCGT GAGCAGGAGG
 251 GGCAGAGGGA GCCTGGAGAG GGTTGGGTCG CCTGGGCAGG CAGCTTTCTG
 301 GGGTGGTGCA CAAGCGACAC AAAGCCTGAG GCTTGGGACC GGCTGAAGAC
 351 GGCCTTGGGC TGCGGGTGCT GGCGCCGCTC CAGGCAGAGG TGGGCTCTGC
 401 AGCCCCCCCC CCCCCGCCAG CTTCCCCCCC AGCAGCAAGA GCCCTGGCCC
 451 CAGCCAGTGG CCCCAAGCCA GGCTCCTGAG GGGCAGAGGG TGAGGGCCGG
 501 ATTTTCCACC ATATTTGTCT CACAGCCTGT CTGGTCCCAG CCCCAGGGCA
 551 ACAAACAGCC TTTCTGGAGC AGTTTCCAGA CCTGCAGTGG CCGCCTTGAG
 601 CCTGCAGTGA CCGTCTGCAG GAGGCCGCGG GTGCTGGGGC TGGCGCAGGA
 651 AAGCACCGTT GCTTCTGCGC CTGTGCAGAG TGAGGCTGGG GCTTCCATCC
 701 CGGGCACGGG ACTCCTCGGC CTCCTGCGGC CGTGTGCATG GGAGGAAGGC
 751 CGTGCTGCCG AGCCACGCGA CTCTGCCCCG TTGGCAGTGG GAAGCGGCAG
 801 GAGGGGGTCC TGCCAGGGGC AGCCAGGGGC TGCTGCAGCT TACGCTCACT
 851 GTCATTCTGA AACCCTCAAC TGGCTTTCAA AATAACAATT TAAAAAATGG
 901 TCATAGGAAA TGCAGGAAGT TCAGGAGAAA TCCCGCCCCG CCCCGCCCTC
 951 CCAAGGCGGC CTCGTTCAAG CTTAGTCTCC GTCTGTTCTC GGGCTGCCTG
1001 CAGCTGCCCC CGCTCCTCAG CAGGTGTGGC CGCGTGTTCA GGAGCCCCCA
1051 TCAGCACACG CGCCTCTGGG CAGCCCCCAA CACAAGGCTC TTCCTGTCCC
1101 TTCAGGCTCA GCTTTCCCCT CCCACCGGGC AGGGAGGTGC TGAGGCCACG
1151 CCTGTTGTCA GCTTCCTGGA GAGGCCATAC TTAGAGCCCA TGGTGCCAGG
1201 CCAAGCCACT GTCTCCCGCA CCACAGTGCT GCAAGCCGGAT CCACCCAGGC
1251 CACCGCTTGG CACCATCAGA CATGCTTTCT TAGTTTGGGC CAGCCCGGTG
1301 CTCTGTGCAC AGTGTGACTC CCAGTGGCCC CTTGCGGGAG GGAGGGTCAC
1351 CGCTTTGCTT CACAAAAGGA CTGAGTCTCA GGGAGGGGTC TCCAGTAAGG
1401 GCCCCGGAGC CAGGATGTGA CTGAGACAGG TGCCTCCAGG GCCACACACT
1451 AACCAGTACA GGAACCTCTG GGGGCAGAAT CATGGCCTCC AAAACACCCA
1501 CATCCAAATC CCAGAACAAA CATGTTACCA TTCGTGGCAG AGAGGAATGA
1551 AGATTGCAGA TTGAATTAAG GTTGTTAATC ATCTGACTTA ATTTTTTTAG
1601 AGACAGGGTC TCGCCCTGTC ACCCAGGCTG AGTTCAGTGG TACAGTCGTG
1651 GCTCACTGCA GCCTCAACCT CTCAGGCTCA AGCAATCCTC CCTTCTCAGT
1701 CTCCTGAGTA GCTGGGACTA CGGGTGTGTG CCACCACGCT TTCCGGGCAT
1751 GCAGCCAGGA GCCCAGGGCC ATCTGTGGCC CACCTTGAGA TCCAGAATCA
1801 TCCATTTCCT CCAGGCCCCC TGCTGGGCTC CAACTCCTTG AGGACCAGAG
1851 AGCAGAGGTT GTGGAAGGCC TTGGAAACGG GTCTGGATTA CCTGTCCTGG
1901 GAAGGTCTCT CCCAACCTGA GTGTCAGACA GGGGTTAGCT CTGCTGCTCA
1951 CAATTTTGTG CCTTAATTCC TGGCTTCCCT TTGGGGATCT TCATCCTCAA
2001 TTCTGATTGA CATCCTTGGC CACAAGGGAC CCCCCTGCTC ATTGATGCTT
2051 CTCACCCGTC ACCTCACTCT CATCCTCACT GCTAAGCAAT TAGCCGTGTG
2101 TTTGCGGCAT CAGTGTTGAC ACCGATGATC CATGCTCAGA GGGTACAGGC
2151 CTGAAGAGCT ATGTGGGGAC TGGCGCCCCG GAGGGGGTCC CGCTGTGGTG
2201 GCAGCGGTGG CCCCCAAGCC CCACGCTCAC TCTGTGTGTC TCCTTGCAGG
2251 ACAGGGTGAG GGGCCTTGGC CTCACGGTGT TGAGACGGGA GTCGGTCTCT
2301 GGAGTGTGGA GTGATGTGCG TCCAGGGTGA AGCTGCACGC ATGGTTGATG
2351 AGGCTTCCTG AGCGCAGGGC TCTGTGCTCA GTGGGTTTTC GCATTCATTC
2401 CCCAGTACCC CTCCGGGCTG CTTGCTGCTC CAAGCCCTGG AAAAGGATGT
2451 TGGGGTTTAG GAAGGCAAAA CTCCATGCCC AGGTCGTGGC TGGTGAGGGG
2501 CGCTCCCCGC ACAACCAGCC ACTGCTTGGC TCCAACTCAC GCCTGGATGC
2551 TGTTAGGCTG GACCCTGTCT GTTTGCAGAT AGCGCCTGTT GACAGATGTG
2601 TCCTGCTGCA GACTTGAAAC GCAGGACTGA GTCTCAGGGA GGGGTCTTCA
2651 CTAACAGCCA TGGAGCCAGG ATGTCACTGA GACAGGTGCC GCCAGGGCCA
2701 CACACTAACC AGTACAGGAA CCTCTGGGGG GCAGAATCAC GGCCTCCAAA
2751 ACACCCACAT CTTAATCCCC AGAGCAAATA TGTTACCATA TGTGGCAGAG
2801 AGGAATGCAC CTGCCGCGTC TAGGAGGCAG AGGGGCTGCG GCGCGTCCCC
2851 AGGTGTCCCC TTGTGTCCTG ACGATGCGTC CCCAGGCATC CCCATGCATT
2901 TCCAGGTGTC CCCACGTGTC CCCAGGCGTC CTCAGGCGTC CTGCCGAACA
2951 GCCCTGTGCC CTCCAGGTGT GCATTGTGCA GAAGCGGGAC ACGGAGAAGA
3001 TGTACGCCAT GAAGTACATG AACAAGCAGC AGTGCATCGA CGCGCGACGAG
3051 GTCCGCAACG TCTTCCGGGA GCTGGAGATC CTGCAGGAGA TCGAGCACGT
3101 CTTCCTGGTG AACCTCTGGT GAGCCTGCCA TGGCCTCGCT GCAGAAAGAC
3151 TTACCGTCCT GAAGCCGGGA AGGCACTGGC TATCCTCTCC TGCCCTTGGT
3201 GCTCCTTGGC CCTCGTGCCT CGGAGATGCC TCTGCCACCC ACAGGCCCTC
3251 TCTAGCCCTC CTCATCTATC CCCCTTCCTG TGCCCCAGGC CTGGCAGTGG
3301 CCCAGGTGGC CATGACATGC TGGGGTTGGT TAATGCAGTG TCTCTTCTGA
3351 GCCTGCCGGA AGACCAGGGC TTCCCTACAA TGGAGATGTG CTCCCATGGA
3401 GTCTCTGGCA CTAGTCAGAG AGGGAGAGAG TTTAGGGACT GAAAAACTCA
3451 CCACTGTCAT CACCATCACC ATCACCACCA TCATCGCCAT CACCACCACC
3501 ATCACCACTG CAACCATCAT CACTCTCATC ACCATCATCA CTATAATCAA
3551 CACAATCACT ATTGTCACCA CCATTACCAC CACCACCACG ACCACAATCA
3601 CTGTTATCAC CATCACCACC ACCCTCAGTC CTCACTACCG TCATCCTCAC
3651 CATCACCGTC ACCACCACCA CCATCACTGC CATCGTCAAC ACCATGGATG
```

FIGURE 3A

```
3701 CTGGTTGTTA AATGCCAGCT CTTTGCCCAA CACTGTCAAG AGTGGTACCT
3751 ACACGGCCTC ATTTTCTGTA ACAACCCTCC GAGGCAAATG TCTGTATCCC
3801 CATTTTACCG AAGAGGAGGC CGGGCAGCCT GAAGCACCCG GAGCTGGCAC
3851 TGTAGCTCTG CTCTGCATTT GCCACTCCCA GGTGCCTCTG GCCCCAGCTG
3901 GGCCACCTCC AGCACAGGGT GGTGTGTCTT TCCTCAGGAT CTGGGCTCAG
3951 AGCTGCTCTG GGCTGGGGTG CAATCAGTGC CTTGGGCAGG CCCCTCCTCC
4001 TGGGAATGCC TGGTGGCTGA TGCTGGGGTG GGGCTGTGGT CCTTAGGGGG
4051 AGTGTGTCAG CTGTGGGAGC AGCCATGACT GGCTCCCCAG CTGTGCGCAC
4101 AACAGGCCTT CCATCGGTGC CCACAGGTAC TCCTTCCAGG ACGAGGAGGA
4151 CATGTTCATG GTCGTGGACC TGCTACTGGG CGGGGACCTG CGCTACCACC
4201 TGCAGCAGAA CGTGCAGTTC TCCGAGGACA CGGTGAGGCT GTACATCTGC
4251 GAGATGGCAC TGGCTCTGGA CTACCTGCGC GGCCAGCACA TCATCCACAG
4301 GTGTGTGCGT GGCAGACGGC GCAGGTACCT GCTGAGGTGG GCGGGGCTGA
4351 AGCAGCCTTA GGTCAGGCTG CCGGCACGGC GGCCGTACTC CCTCAGAGCG
4401 GGTCTAGCTC CTCTGCCCCA CCCTTGCCTG AGTGCCTGCC CCCAGCTGTG
4451 GCACCTGTGC CGACCAGGTC AGCCCCATAG CTGTGTGCCT GGTGTCCATC
4501 TGGGGGGACC TCGTCCCAGC AGCCCCAGCT GAGACTGGGC ACAGTGGGCT
4551 GTTAGCCCTG GTGGACAGAC CACCAGGCTG GGTCACAGCA GGTGGCCTTC
4601 ACCTGGTCCA TTTAACTGAA GACTCCTGTT TGCCCATCCA CCACATCCCA
4651 GGGAATCCAA ACTAATTTTA ACATTAGCTT AAAGCAGATG AAATTAGGAA
4701 GCAGAGCTGG TGTGATGGCT CTGAAAATAA AATTTAAAAA AAGAAAATAG
4751 GAAGCAGATT ATGAAGGAAG TGAAATTGGG AAGCAGAAAT TAGGCTGAAA
4801 TTCCGCAGCA ATGGAACAAA ATGAAAATAT CTGTGAGGTA TATTTTAAAG
4851 TCGAATGGAC TGGTGTTTGC ATTTCTGCTC TTGGGGACTC GGATGTCTGA
4901 TTATGACCTA GGCACCAGTC ACTGAGCACT GGCTGTGTAC CTGGAAAAGT
4951 TGGGACAAAG CAAGAGCCGA GGTGGCTTGG TCTCCTAGAG GCCGAGTCTT
5001 GGAGGGGGAG GGCCAGCAATT GCTCTCGTCC TCTGGGGCTC
5051 CAGGCCCCCT CCCAGCATCT GGTGCCAGGT GTGTGCTGCT GCCCAGATGC
5101 CACAGGGAAC GAAGTGGCTG ACTTCATCGC CTCTGCCCCC ACGCAGGGGT
5151 GTGAGGTCCT AGCATCATCC AAGGACCAAG TCAAGCTCCC AGGCCTCTGC
5201 CTCGAGTGGG TTGGTGGGAT GTCCTGGGGA CTCCAGGGAT TGTGACAGAG
5251 ATTCCAGGGC AGAAACAGGG CAGATTCCCA ACTCACCTTC CCACTTTCTG
5301 CTCTTTCTAG AGATGTCAAG CCTGACAACA TTCTCCTGGA TGAGAGAGGT
5351 GTGTGGGGTT GGGTGTGGGC AGCCCAGGTG GGTGGTGGCA GGGATGGGCC
5401 TGTCAGGGGA GGAGGATCCT GCACGCAAGG ATGCATCTCT GGTCCTGGGA
5451 CAGCCACACC TGACCCCTCT CTGCACAGGA CATGCACACC TGACCGACTT
5501 CAACATTGCC ACCATCATCA AGGACGGGGA GCGGGCGACG GCATTAGCAG
5551 GCACCAAGCC GTACATGGGT GAGCCCGAGC TGGGGTTCCA GATGGGAGCT
5601 GGCTTCCTCC AGGTGGGAAG GACAAGACCT CGGTGGCTTC TCTGTCCCAC
5651 CCTGGAGGCA GCCTGGTCTC GGGATGTGGC CTCAAGGTGC CGGCCCTGTG
5701 CCCACGGGTC CGGGCTGTGA CCCCGTGGCA GCTGTTTTTC CTTCTTTCTG
5751 TCGGAAAGCT CCGGAGATCT TCCACTCTTT TGTCAACGGC GGGACCGGCT
5801 ACTCCTTCGA GGTGGACTGG TGGTCGGTGG GGGTGATGGC CTATGAGCTG
5851 CTGCGAGGAT GGGTATGGAC CCCCTGCAGC CCCCGGGCTT GGCTGCCAGG
5901 CCCCTGCTCT CTGCCCCCAC CAGTGCTGGG GAGGGGGTGG CTGACCCAGT
5951 GCCCAGGTGC GCAGGGATGT CTCCACTGTG TCTGAGGAGT CACGCTTTTA
6001 TCGAAGTGTG TAGTTGGTGA TGGAATGCCT GAGCAGGAGG AGGAAGGACA
6051 GACTCACTGT GGTTTCCCGG GGCCGCTGCT GGTGCCTGCA GGCCAGCCTC
6101 TGTGGGGGTG GACAAGGCTG AGAACTGGCC AGCAGGGGTG CTGCCTCGGA
6151 ACTTTCCACA AAAAGTTTCT TTTGGGGCCC TGTGCTCTTA CCCTTGTTGC
6201 CACGGCGAGG CCAGTCCTGG AGACCGGGAG GCTGGGGGTC CTCTTGTGGA
6251 CCGTACCCCT CAGCCCTGCA CAGGACCCCA CCTCTGAGGA AGCCAGCTCC
6301 CTCCTGGCCC TCTGGGGCTG ATCTACCTGG ACCCAGGCCC CCTGGGATCC
6351 CAGCCAGATG GGCGCAGCAG CCAGGGCCCA GGACCCAGGC GTAAGCTTTA
6401 TCTCACCCAG GCTCCTCCGC GGCAGGTGGA GGCCAGGCTG TGCTCAGAGC
6451 TGTGCCTGCA CTTGGGGTGG GGGAGGGGG TCCTCTCAGG GCGATGGCAC
6501 CTGTGTCTGG CATTGTTCTG GGTGTCCTGG GGGCCAGGAG GACCTGCCCA
6551 GCACTGCCTC CCTGTCTCCA GAGGCCCTAT GACATCCACT CCAGCAACGC
6601 CGTGGAGTCC CTGGTGCAGC CGTGAGCGTC CAGTATGTCC
6651 CCACGTGGTC CAAGGAGATG GTGGCCTTGC TGCGGAAGGT GAGCCCCCAT
6701 CCCTGAGCCT CCTCACCCTC CGAGCACCCA CCTCCCTCCC TCACTTACCT
6751 GCGGCTCGGG ACACCCCCTC CAGTGCACAG TTAGTGCCGC TTCCTGGCAG
6801 CACAGATCC CTTCACTGCA ACCTGTGGGG GCCTCCGCAG ATGGCAGCCC
6851 CAAGCCCCAG GAAGCGAGCT GGTGGCAGGG TCTGTGGCCC TCTCATGGCG
6901 AGCCCTACCA GGTCACTGGT GTCCGGTGA TCCCCTGAGC TGCGTCTCCA
6951 GGCACCCTCA CAGCAGGCTT GTGCGCCCGC CCTGCCGGTC ACCACAGAGG
7001 AGCCCTGAGC CACGTCCCCT TGTCCCACGT ATTGGAAGGA GGGTGTCGGG
7051 TGGGTGGGTT CAAGCCCATG CTATCTCCGG GACCCTTTGC CCCATGCCT
7101 CCTGGGGAAG GTGGGCAGCC ACTGCCCACT GCAAACACCT CTCAGGGGAC
7151 ATCAGCCTGG CAGGACACG GCAGGGGTG TGGCCATCAG TAGTGCCTCC
7201 CATTTGTGAT CTGGTGCTAG GCTGGGGCTG TGCCTTGACT GGGCTGCACA
7251 GCTCCCTGTT CCGAGCCTCG CATTAACACC ATAGGGGGTT CGGAGTCAGA
7301 GCCAGGCCCA GGCAGGACAG GGAGGGGAGT GAGTGTGCCA CACGGGCCCG
7351 GCTGCCTCCC GGCCCCCGTG TCTCAGGCAG GTGGGGCCTC CTGCCCTGGA
```

FIGURE 3B

```
 7401 ATTGTAGCCA AGCAGCCTAA AGCCTTGGGG AGGCCTTGCC TGCCGGGGCC
 7451 TCTCCCCAGC CCCGAGAGTC TCTTAACTCT GCTGTAGCCC CATGAAGCTC
 7501 AGTCACACCT GCCCAGGTGG CTCACAAGGT GGCACTGGGC TAGAGAGGGC
 7551 CTGCGTGGGG ACTGGGGATG ACCCACACGC CCAAGCCCAG GTCTGGGAAA
 7601 CCTCGCACGG GGTCTGGGTC TGCGGCATTT TCCCTGGAAA GGCGGGAGGT
 7651 GCCAGCGCTG GGATGTTGCT TCCCAGGCCA TGCATGGCTG CCCCGGGCTC
 7701 ATCTGGCCTG TGGAGGTCCC ATGATTCGGT GAAGGAAGTG GCTCTGGGAT
 7751 AGTTACTGTG AGGCCAGCCA TGTGCCGAGT GTTAGCCGCT AGCCGGGCCT
 7801 CGGCTGCCAC CTCCTGGCAA ATCCCAGCAG AGCCTTCCCT GCAGATCCCT
 7851 CTGCTGTCCT CTGGCCGCAG GGGTTTAGGT AGCAGCACTG AGAACAGGCG
 7901 TCCCTTGGGC CACATGCTGA GCCAGCCACG GTGCTTTGCC TGATGTCGGC
 7951 CGTCGGCACC ACCCTTCCTC GCGTGGCCCT GAGGTTCCTG AATTCTGAAC
 8001 CTGAGGCTTG GTGGGACCCT CCTCAAGGTG CCCTGGCCTG GGGGTGGCGG
 8051 GCTATTCCGT GCTGGTGGGC TGTGGGCCCT GGACCCTCTG ACTCATGCCT
 8101 GGTTGCAGCT CCTCACTGTG AACCCCGAGC ACCGGCTCTC CAGCCTCCAG
 8151 GACGTGCAGG CAGCCCCGGC GCTGGCCGGC GTGCTGTGGG ACCACCTGAG
 8201 CGAGAAGAGG GTGGAGCCGG GCTTCGTGCC CAACGTAAGC CTGTGGGCGG
 8251 CTCAGGTGGG GGGCCCTGGG GATGGATGTG GCGTCCTCCA CGGGCCGGGG
 8301 CTCAGCACCC ATCCCTCTGT AGAAAGGCCG TCTGCACTGC GACCCCACCT
 8351 TTGAGCTGGA GGAGATGATC CTGGAGTCCA GGCCCCTGCA CAAGAAGAAG
 8401 AAGCGCCTGG CCAAGAACAA GTCCCGGGAC AACAGCAGGG ACAGCTCCCA
 8451 GTCCGTGAGT GCCAGGGCAG GCTCAGGGCG CGGCGGCGGG CTGGGCTTGG
 8501 GGCTCCTCTC TACCACCGAG CAAGGTGTGT GGGGACCCCT GACAGTGCAC
 8551 ACGTCTCGGA AGTCCAGCAG ACCGTTTCCT GAAGTCCTGA GAAGGCCAGA
 8601 GACCTCCCTT CTGCCTTTCC CAGCCCCCAC CTCGCTCCTT ATGAAGCAGG
 8651 TGGGCAGGGA CAACCAGGGC TGGGGTTATG AGTGCACGGG GATGGCCATG
 8701 TGAAGCCTTC GTGCTTGCCC AGGTGTGCTG GTGTTGGTTG TGTGTGCGGG
 8751 GACGGCTATG TGAAGCCCTC ACACTCGCCC AGGTGCGTCG GCATCAGGTA
 8801 TGTGTGCCGG GACAGCCATG TGAAGCCCTC ACACTCACCC AGGTGCGTCG
 8851 GCATCAGTTG TGTGTGTGGG GACGGCCATG TGAAGCCCTC ACACTCGCCC
 8901 AGGTGTGCTG GCTTTGGTTG TGTGTGCAGG GATGGCCACA TGAAGCCCTC
 8951 ACACTCGCCC AGGTGCGTCA GCATCAGGTG TGTGTGCGGG GACGGCCATG
 9001 TGAAGCCCTC ACACTCGCCC AGGTGCGTTG ATGTTGTGTG TGCAGGGATG
 9051 GCCATGTGAA GCCCTCACAC TCACCCAGGT GCGTTGATGT CAGTTGTGTG
 9101 TGCAGGGACA GCCATGTGAA GCCCTCAGAC TAGCCCAGGT GTGTCGGTGT
 9151 CAGTTGTGTG TGTGGGGATG GCCACGTGAA GCCCTCACAC TTGCCCAGGT
 9201 GCGTTGATAT TAGTTGTGTG TGCAGGGATG GCCACGTGAA GCCCTCACAC
 9251 TCACCCAGGT GCGTTGATGT CAGTTGTGTG TGTGCGCAGG GATGGCCACA
 9301 TGAAGCCCTC AGACTCGCCC AGGTGTGCTG GCTTTGGTTG TGTGTGCAGG
 9351 GACGGCCATG TGAAGCCCTC ACACTCGCCC AGGTGCGTCA GCATCAGTTG
 9401 TGTGTGTGGG GACGGCCATG TGAAGCCCTC ACACTCACCC AGGTGTGTCG
 9451 ACATCAGTTG TGTGTGGGGG GACGGCCATC TGAAGCCCTC ACACTCACCC
 9501 AGGTGTGTCG GTGTCAGTTG TGTGTGCGGG GATGGCCACG TGAAGCCCTC
 9551 ACACTTGCCC AGGTGCGTTG ATATTAGTTG TGTGTGCAGG GATGGCCACG
 9601 TGAAGCCCTC ACACTCACCC AGGTGCGTTG ATGTCAGTTG TGAGTGTGTG
 9651 CAGGGATGGC CACGTGAAGC CCTCAGACTA GCCCAGGTGT GCTGGCTTTG
 9701 GTTGTGTGTG CAGGGACGGC CATGTGAAGC CCTCACACTC GCCCAGGTGC
 9751 GTCAGCATCA GTTGTGTGTG TGGGGACGGC CATGTGAAGC CCTCACACTC
 9801 GCCCAGGTGC GTCAGCATCA GTTGTGTGTG TGGGGATGGC CACGTGAAGC
 9851 CCTCAGACTA GCCCAGGTGC GTCGGCATCA GGTGTGTGTG CCGGGACAGC
 9901 CACGTGAAGC CCTCACACTC GCCCAGGTGT GTTGTGTGTG
 9951 CGGGGACGGC CACGTGAAGC CCTCATGCTC ACTCAGGCAT GCTGGTATTC
10001 TGGGGCTGCC AGGACAGGTG ACCACGAATC AGGTGGTTGA AGAACAGCAA
10051 TGCGTCTCTC TGAGAGGATC TGAGTCGTAA TGAAATGGTC TCCTTCACAG
10101 CCGGCTGTGC GTGAACTACT CTGTCTCCTG CAGCTCCCCT GTCTTGATAA
10151 TTGGCTGTCT AGGCAGCGGG TAAGGTGAAC CCCTTGGGCA GTTATGTGAT
10201 GATCTCAGTT TCTGTAAACC GGAAGTCCAG GCATGGTGCA GCTCTGTTCC
10251 CTGCTTCGGG GTCTCACCAG AATGTGAGCT AACATTGAGG TCGTGGCCTT
10301 GTCAGGTGCA GCTCTGTTTC CTGCTTCTGG GTCTCCCCAG AGTGTGAGCT
10351 AATATTGTCT GAGGTCGTGG TCTCATCAGG GATTTGACAG GTGTGTGGT
10401 TGAAATGTTT CCCTTAAAAC TCGTGTTGGA ATTTGCTTCC TATTGTGATG
10451 GTGGTAGAGA TGGGACTTTT GGGGCTGAT GGGGCCACGT AGGTTCTTCC
10501 AGCATGGATG GGGTTAATGC TGTTGTAGAA GGGTGACTTT AGTCCTCTTT
10551 TGAGTCTTTG ATCCTCTGCT ATGTGAGGAC GTGGTGTTCC CAATGTGGAC
10601 GTGGTTCGTG TTCCATGTGA ATGTGATATT CACAATAGAG CATCAACAGG
10651 CTCCCTTTTA ATCAGCAGAT TTAAAAAGAA ATGTGTTGTC TCATGGCTTG
10701 GAGGCCTGAG TCCAAAGTTA AGATGTCAGC AAAGCCGTGC CCCCTCTGAA
10751 GGCTCTCCGG GGAGGAAAAC CAGTCCTTGC CCCTCTACCC TCCGGTAGAG
10801 GCTGCCTTGG CCTAGACGCA TCCCCCCAGC CCCTGCTTCG CTGCCGCGTG
10851 GGGTCGGCCT GTGTGTGCGT CTCCATCTCC TCCCCTCTTC TCATAAGGAC
10901 ACCAGGCATT GGATTTAGGG CCCACCCTGA TCCAGTATGG CCCCATCTTA
10951 TCTTGATGAT ATCTGCAAAG ACCTCACTTC CAAATGAGGT CACATTCACA
11001 GGTACCCAGG ATTAGAATTT GAGTGTGTCA TTTTTGGGGA CACAGTTTGG
11051 CCCATACCAC CAGGATGTGG CTGATATTCA CCAAGGAGTA GCTATGGTTG
```

FIGURE 3C

```
11101 TGTGTTGATG TCAGGGTGAC GGTGATGACC CTGGGTCCCT CGGTGGTCCC
11151 CTTGCCCCTG AGTCTGCCTG AGCCTGTGGT GGATGTCCTG GGAAACTCTT
11201 GTGCCTCAGC CCCCGTGCAG CCTCCTCAGA CCTGGTGGGC CCTGTGTTGC
11251 TCCTGGGCAG AAGACGGGTG TCAGTCCCCT CCTCACCATG ATGTGGGGGG
11301 CAGGGGTGGG GTCATGCCCT GGGTGCCCTG ATTTTGGGGG GAACACGGCC
11351 CCCCAGTGGG TCAGGCTCCC ATCCTCGCCC CTCCTCCAGG ACGGCTGCCG
11401 GCAGCCCTGG GTGTCCTCAG GCAGAATTGC TGGTGGAGAG CTGCTGTCTG
11451 CCAGGTGGCC ACTGTGAGGC ACTGCTGAGA GCCACAGGAT GGTTGGAAGG
11501 TTCTCGGGGT TGGGGGTTCT TTGGCATTGC CCCCATTGGA TGTTTAAGTT
11551 TTCCCTACCA GAGCATGTCC AGAGCCAGGG CTCTGGGGTG TAGAAACAGG
11601 CCCAGGATGA GTTAGGAACC CTCATGGGAG ACTCAGGGAT GGACAGTGTG
11651 CAGAGCCCAG CTGGCCATGC TGAGTTCCCA GGAGGCTCTG GCTGGGAACA
11701 GGTAAGGCCA GGCACCTGTG AGCGGGAGGA GCTCGGCTTT GTCTTGGGTT
11751 GGTTGTGTGG AGATGTTTTG GCTTGAGGGT AGGAGGTGTT CTGAAAGGAA
11801 AGCATCACTC CAAAAAAAAA GTCCCACTGT TAACCTTGAG GCTGAGAGAG
11851 GTTTTTGGAA ACAGCTTTAT TTTGATATAA TTCACATTCC ATGCAATATA
11901 CAGTGCATCA ATGTAAAGCA TATAATTCCA TGGTTTTTAA TATAGTCACA
11951 GGGCTGTGCA TTCTCCACCA CAATCTGATT TTAGAACCTT TTCATGTAAT
12001 GTAAGAGAAA GACCCCACCT ATTAGCAGTC ATGCCCCATT CCCCTCTTCT
12051 CCCCTCCCCT GGCAGCCACG AAGCTACTTT CCGTCTCTGT AGGGTTGCCT
12101 GTTGTGGGCG TTTCATGGAA GTGGAGTTAC ACACTATGTG GTCTTTGCAG
12151 CTGGCTTCTT TCACTTCGCA GGATGCTTTT GAGGCCCGTC CACGTTGTAG
12201 CCTGTCAGTG CTTCATTCCT GTTGATGGCT GAGTAATATT CCACATATGT
12251 ATCACCTTTC CTTTATCCAG TCATCAGTTG ATGAGTATTT GTTCTTTCCA
12301 CTTGTTAACA TTTTTCATTA TCATGAATAA TGCTGCTGTG AACATTCACA
12351 TACAAGTCTT TGTGTGGATA TGTACTTTTA TTTTTGGGGG GCACATACCT
12401 AGGCATGAAC CCGCTGGGTC ATATGTGACT CTGTGCTTCA TGTTTGGAGG
12451 AAACACCTAC CCTTTTCTAC AGCAGGTGTG CCATTTTATG CCCCTACCAG
12501 CAGTGTGTGA GGGTTCTAAT TTCTCCATAT ATTTACCAAG TCCTGTTATT
12551 GTCTGGTTTA TTTTTTTAAA AATCATAGTT ATCTTAGTGT GCAGTGATTG
12601 TGTGGTTATG GTTTGCATTT CTCTGATGAT ATTGAACATC TTTTGAGGTG
12651 TTTTATCAGG CATTGTGTCT AGAGAAATGT CTATCCAAAT GTTTTAAAAT
12701 TTTTATTGTC TTTTTTTTAG TCTACTCTGA CAATATATTT TAATTGGCAT
12751 ATTTATTTTA CTTTATTTTT TTTTAGAGAC AGGGTCTTGC TTTATTACCA
12801 AAACTGGAGT GCAGTGGTGC AATGAAGGCT CACTTCAGCC TTGACTTCCT
12851 GGGCTCAAGT GATCCTCCCT GCCCCAGCTG CCAGAATGGC TGGAACTGTG
12901 GGTGTGCACC ACCACACCTG GCTCATTTGA AAAAAATTTT GTTGTAGAGA
12951 CAGGGTCTCA CTATGTTGTC CAGGTTGGTC TCAAACTCTT GGAGTCCTCC
13001 CACCTCAGCC TCCCAAAATG CTGGGATTAC AGATGTGAGC CACTGTGCCT
13051 GACCTAATTG GTGTATTTTA GACCATTCAC ATTTAAAGCG ACCAGGGAGG
13101 CTGAGGCAAG AGGACTGCTT GAGTCCAGGA GTTTGAGACC AGCCTGGGCA
13151 ACAAGGTGAG ACCCATCTGT ATTAGTCTAT TTTCACACTG CTAATAAAGG
13201 CATACCTGAG TCTGGGTAAT TTATACAGGA AAAAGGTTTA ATGGATTTAC
13251 AGTTCCACAT GGCTGGGGAG GCCTCACAGT CGTGGAAGGC AAGGAGGAGA
13301 AAGTCACATC TTACATGGAT GGCGGCAGGC AAAGAGAGAG CTTGTTCAGG
13351 GAAACTTTTG TTTTTAAAAC CATCGGATCT CATGAGACTC ATTCACTATC
13401 ATGACAACAG CACAGGAAAG ACCCGCCCCC ATAATTCAAT CACCTCCCAC
13451 CAGGTTCCTC CCACAACATG TGGGAATTGT GGGAGTCACA ATTCAAGCTG
13501 AGATTGGGAT GGGGACAGAG CCAAACCATA TCATTCTGCC CCAGCCCCTC
13551 CAAAATCTCA TGTCCTCACA TTTCAGAACC AATCATGCCT TCCCAACAGT
13601 CCCCCATAGT CTTATTTTGG CATTAACTCA AAAGTCCACA GTCCAATGTC
13651 TCATCTGAGA CAAGGTAAGT CCCTTCTGCC TATGAGTCTG TAAAATCAAA
13701 AGCAAGTGAC TTCCTAGATA CAATAGGGGT ACAGGCATTG GGTAAATTCA
13751 GCCATTCCAA ATGGGAGAAA TTGGCCAAAA CAAAGGGGCT ACAGGCCCCA
13801 TGCAAGTCTG AAATCCAAGCA GGCCTGTCAA ATCTTAAAGC TTCAAAATGA
13851 ACATCTTTGA CTCTATCTCT CACATCCAGG TCATGCTGAT GCAAGAGTTG
13901 GGTTCCCATG GTCTTAGGCA GCTCTGCCCT TGTGGCTCTG CAGAGTACAG
13951 CCTTCCTCCC GGCTGCTTTC GTGGGCTGGC ATTGAGTGTC TGTGGCTTTT
14001 CCAGGTGCAT GGTGCAAGCT GTTGGTGGAT ATACCATTCT GGGGTGTAGA
14051 GGATGGTGGC CCTCTTCTCA GAGCTCCACT AGGCAGTGCC CCAGTGGGGA
14101 CTTTGTATAG GGGCACCAAC CCCACATTTC CCTTCTGCAT TGCCCTAGCA
14151 GAGGTTCTCC ATGAGGGCCC CACCCCTGCA ACAAACTTCT GCCTGGACAT
14201 CCAGGTGTTT CCATACATCC TCTGAAATGC AGGCAGAGGC TCCCAAACCT
14251 CAATTCTTGA CTTCTGTGCA CCTGCGGGCT CAACACCACA TGGAAGCTGC
14301 CACAGCTTTG GGCTTGTACC CTCTGAAGCC ACAGCCTGAG CTGTACCTTG
14351 GCCCCTTTCA GTCATGGCTG GAGCAGCTGG GATGCAGTGC AGCAAGTCCC
14401 TAGACTGCAC ACAGCAGAGG GACCCTGGAC CTCGCCCATG AAACCATTTT
14451 TTCCTCCTAG GCCTCTGAGT CTGTGATGGT AGGGGCTGCC GCAAAGGTCT
14501 GTGGCATGCC CTGGAGACAT TTTCCCCATT GTCTTGGTGA TTAATATTCA
14551 GTTCCTTGTT GCTTATGCAA ATTTCTCCTC AGAAAATGGG GTTTTCTTTT
14601 TTTTCTCTCT TTTTTTTTTT TTTTTGAGAC AGTCTTGCTC TGTCACCCAG
14651 GCTGGAGTGC AGTGGTGCAA TGGCGGCTCA TTGCCACTGC AACCTCCGCT
14701 TCCTAAGTTC AAGTGATTCT CCTGTCTCAG CCTCCCAAGT AGCTGGGATT
14751 ACAGGCACGC ACCACCACAC CCAGCTAATT TTTGTATTTT TAGTAGAGAA
```

FIGURE 3D

```
14801 GGGTTTCACC ATGTTGGCCA GGCTGGTCTT GAACTCCTGA CCTCAGGTGA
14851 TCTGCCTGCC TTAACCTCCC AAAGTGCTAG GATTACAGGC GTGAGCCACC
14901 GTGCCCAGCC AGGAGTTTCT TTTCTATTGC ATTGTCAGGT TGCAAATTTT
14951 TTGAACTTTT ATGCTGTTTC CTTTTTAAAA TGGAATGCCT TTAACAGCAC
15001 CCAAGTCACC TCTTGAATGC TTTGCTGCTT AGAAATTTCT TCTGCCACAT
15051 ACCCTAAATC ATCTCTCAAA TTCAGAGTTC CACAAATCTC TAGGGCAGGG
15101 GCAAAATGCT GCCAGTCTCT TTGCTTAAAG CATAACAAGA GCCACCTTTG
15151 CTGTAGTTCC CAACAAGTTC CTCATCTCCA TCTGAGACCA ACTCAGCCTG
15201 GACTTCATTG TCCATATCAT TATCAGCATT TTGGTCAAAG CCATTCAACA
15251 AGTCTCTAGG AAGTTCCAAA CTTTCCCACA TTTTCCTGTC TTCTTCTGAG
15301 CCCTCCAGAT GGTTCCAGCC TCTGCCTATT ACCCAGTTCT AAAAAGTTGC
15351 TTCCACATTT TCAGGTATCA TTTCAGCAGC GCCCTACTTT ACTGGTACCA
15401 ATTTACTGTA TTAGTCTGTT CTCACGCTGC TAATAAAGAC ATATCCGAGA
15451 CTGGGAAATT TATACAGGAA AAAGGTTTAA TGGACTTACA GTTCCACATG
15501 GCTGGGGAGG CCTCACAATC ATGGCGGAAG GCAAGGAGGA GCAAGTCACA
15551 TCTTACATGG ATGGCAGAGA GAGCTTGTGC AGGGAAACTT TTGTTTTTAA
15601 AACCATCAGA TCTCATGAGA CTCATTCACT ATCATGACAA CAGCACAGGA
15651 AAGACCCGCC CCCATAATTC AATCACCTCC CACTGGGTTC CTCCCATGAC
15701 ACACGGGAAT TGTGGGAGTC ACAATTCAAG CTGAGATTGG GGTGGGGAGA
15751 CAGCCAAACC TTATCACCAG CTCTATAAAA GACAAAAAAA TTAGGCAGGC
15801 ATAACAGTGC ATGCCTGTAG TTCCAGTGAT GTGAGAGGAT TGCTTGAGTC
15851 CAGGAGTTTG AGACCAGGCT GGGCAACATG GCGAGACCCT GTCTCTACAA
15901 AAAAAAATTA TCTGGGTGTG GTGGGATACA CCTGTGATAC CAGCTACGCA
15951 GGAGGCTGAG GCAGTAGGAT TGCTTGAGCC CAGGAGTTCA AGGCTGCAGT
16001 AAGCTATGAT CATGCCCCTG CACTCCAGTC TGGGTAACAG AGAGACACGC
16051 TGTCTTGTAA ATAAATAAGT GGTCATTTAT ATAGTTCAAT ATGATATCTA
16101 CCTTATTTGT AACTGTAGTC TATTTATTGG TCTTCCTTTT TCCCTATTTT
16151 TCTGCCTTTT CTGGTTTTAA TTAAGCATTT TATATTATTC TAGTTTATCT
16201 CCTCTCCTGG CCTGTTAATT ATACTTCTTT TTGAAATATT TTTAGTGGTT
16251 GGCCTGGACA TTGCAGTATA CCTTTACCAT ACAGTCTACC TTCACCTGAC
16301 ACTCTGCCCC CTCATGTGCA GTGGGATGCC TTGTGACGGC ACCTCTCGTG
16351 CAATCCTCCT GTTCCTGATG ACATTGCTGT CATTCATTTC ATTTATCTGT
16401 ATGCTATAAT TGCTCATTAC ATTGTTACTA CTGTTATTTT AAACAGTTAT
16451 CTTTTGGATC AATTAAGAAA AATTAAAAAT TTCATTTTAC CTCTATTCAT
16501 TCCTCCTCTA AAGTGCTTCC TTTCTTTATG CAGACCCAAG TTGCTGACCT
16551 AAATCATTTT CCTTTCCCCT GAGGAACTTC GTTTAACATG TCTTATAGGA
16601 CAGGTCCAAC AGAGATGAAT TCCTTCCCTT TTTGTTTGTC CAAAAAAGTC
16651 TTTACTTTCA CCTTTAAAGA ATAATTTCAC TGGATATAGA ATTCTAGATT
16701 GGTAGGTTTT TTACTTTCAA CACTTTAAAT ATTTCACTCC GCTCTCTTCT
16751 TGCTTATGTG ATTTCTAACA GGCAGTCTGC TCTAATTCTT TTTCTGTAAG
16801 TAGAATTCCT CGCCACCCCC CACCCCCAGC TCATTTCAAG ATTTTCTCTG
16851 TCTTTGGTTT TCTGCAATTT GAATAATGAT ATGCCTAGGT ACAGATTTTT
16901 TTTTAATATT CATTCTGCTT GGTGTTCTCT GAGCTTCTTA GATCTGTGGT
16951 TTGGTGTCTG TCATTAATTT CAGAAAATTC CCAGTCATTA TTATTTCAAA
17001 TATTCTGTTC TCTTTCTCTT CTCCTGCTGG AAATCCAATT ATGTGTGTGT
17051 GGTGCCGTTT GAAATTGTCC CACAGCTCTT GGATATTCTG TTCATTTTTT
17101 TCACTCTTTT TTTTTTCTCT TTGCATTTTA GTTCGAGAAG TTTCTGTTGA
17151 CATTTCTTCA AGCTCATAGA TCCTTCCTCA TCTGGATCCA GTCTACTGAG
17201 GAACCATCAA AGGCATCCTC ATTTCTGTTA CAGTGTTTTC TACTTCCAGC
17251 ATTTCCTTTT GATCCCTCCT TGGAGTTTCC ATCTCTCTAC TTACATTGCC
17301 CTTCTGTTCC CCATCTGTTC TTGCCTGCTT TTCCCCTGGA GCCCTTGCCA
17351 TATTAATCAC AGTTATTTCA AATTTCCTGT TTGATAATTC CAACATGGGT
17401 GCCATATCTG GATCTGTTCT AATGTGTGCA TTGTCTCTTC ACACTCTATT
17451 TTTTTCCTTA AGACCTTGTA GTCTGCCTTG TAATGTTTGT TGAAAGCTGG
17501 ACGTGATGTA TCTGGTAATA AGAGCTGAAG TAGATGGGCC TTTAGTGTGA
17551 GGTTTATGTA ATCTGGCCAG GTTTGGGGCA GGGTTTAAAG TCTGCTGTAG
17601 CTGTGGGTAC CAGAGGCTTC ACATTTGTTT TCATTTCCCG GGTTGCCCTT
17651 GGGCTTGCCT AAATCCTCCT CCTCAGAGAG AGTCTGCGTC TTGTGGCCCT
17701 CTCTGCTGGA ATCCCTGTCA CACTGCGGAG GCCCTGTGGG TGTGTTGGGA
17751 AGATGGTGGG GAGGGAACTG TTCCACAGTC TGTGACCAAA TCTCAGTCTT
17801 GGGGGCCTGT GCCCCTTCAC AGTTGTTGAT CTGCTTTTCC CCTCCCCTTA
17851 GGTGAGACAG GCTAAAGCGG GGTACAGGCT GAAAACAGT CCTCCCCCAA
17901 GTGAGATAAG CCTTTCCTTT GGAGAGCAAA TTCCATTTGC TGTGGAGAAT
17951 GCTCTGGGTG TATTTCACAG TGGTGACTGT CCCCATCCCA TGCCAGAGCC
18001 AGGAAGGGAT CATCCTTGGC TTCATTAAGA CCTGGCAGGG TTCCTGGAGG
18051 GGAAACCCAC AAAACGTTGG GGGCCTCATA AGACCGCAGC CGCAGGAGTT
18101 CTGCACACGG CCCCGGCCGC TCCCCAGAGC TGCCCAGGAG GTGTTCCCGC
18151 ACACCATCAG TTCTGCTCCA GGCCAGCAGG TCTCAGCTGT GACTTTGCTC
18201 ACCTGTCTCT CCAGACTTGG GGGTCGCCGC AGCGCTTTGA CCTCAGCTCT
18251 CTGATGGGTC CAGGAAAAGT AATTGATTTT CATTAGTTCA GCATTTTTCC
18301 TGTCGCAGGG ATGGGAGTGA GGCCTTCCAC GTTGTTTGCC GCAGAGCAGA
18351 AGCCAGAAGT CCTTGCTCGT CTCTGTGTTT CTTCGTCGGA GTCATGTCTT
18401 TTATTTCCTG AACGCAGGTG TGTGGTCAGA CAGGAGATTG GCAGGTATTT
18451 CCTCCTGTTC CATGGGCTAT CTTTTCTCTT TCTTGAGGGC ATCATTTGCA
```

FIGURE 3E

```
18501 GCAGGGAAGT CTTGGACCTT GACGTTGTCC GATGTGGCTG TTTCCTCCTT
18551 GGCTGCTCTG CTTTGTCTAA GGATCCATCA CCTCAGCTGA GGCCACAGGG
18601 ATTTACTCCC ACACTTTCTT CTAAGTCTTG TATAGTTTCA GCTCTTGCGT
18651 TTAGCTGTGT GATTCATTTT GGGTTAATTT TTATGAACAA TGTCAGGTGA
18701 GGGTCCAGCT TCATTCTCTC ATCGGTGGAT ATCTGACTGT CCTAGCACCA
18751 TTTGCTGAAG AGAGGATTCT TTCCCCATTG AATTGCTTTT GACATCATAC
18801 CTTGTTTTTT GACTTGCCGT TTTATCCCAT TGGTCCAGAC GTCTGCCCTG
18851 CGCCGGGACT GCACCATCTT GATAACTGTA GCTTTGTAGC AAGCTTTCAA
18901 ATCAGGATCT GTGAATCCCC CAGTTTTGTT CTTTTTGGAC ATTATTTGAC
18951 TATTCTGGGT CCCTGGCATT TCCACTGAAT GCTGAGGGGT CTGACAGTTG
19001 CATCTGAGCT GCCAAGCAGG TTTGTGGCGG TGCTAGGGAC TGAAGCCTGC
19051 TCCATTTCCC AGGCCCCTCC TCGCTGTGGG TGACATCTGG GGTCCGAGGC
19101 TGTGTCTCAG CATGTGTGAA GGTGCCACGG GTGCCCTGAG ATGGGGATTC
19151 CTGGTCCAGT TACTCAGAAA GTGCATCCAG GAGAGACCCC CGCCCTTCTC
19201 GGGATGGGAG ATGCCAGCAG AGCTTGGCTT TCAAGCAGAA ATCTGGAAAC
19251 CCTGTGGGGA GTGGCTTCGG ACTTCAGGGG ACCTGGAGCG TCACTTGTGG
19301 TTCAAGAGGT CCCTGCCCTG AGGGAGCTGG GCTCTCAAAC ACCCACACCA
19351 GTCAGTCATG GGCGAAGGGC CCCTCTGTGG CCTTCTGACT GTGTGTGTGC
19401 TGGCAAAGGG TTCCAGCCAC CCAAGGAGGA GGCAGGGGCT GTCAGAGGAA
19451 GAGCAGGGCA GATCCAGCCC AGGCACAGAC CCTGCCATGG GGTATGCTG
19501 GCGGCGCTAC ACACACCTTG GGAAGGGAGT CCCTGTGGAA AGGGGTCGTG
19551 GTCACACATC TAGGTGACAC AGCCCGGCTT GGGCGCTGCT CAGAGCCACC
19601 CCTTCCAGAT GGTTCTGGAG CAGCTCCTCA GGCTTCTGGT GGCCTCTCTG
19651 CCTAGGAAAA CATGGCTGTG GACGTTGCAG GATGACCAAC AGCCCCTGCC
19701 ACTGGGCTGC ACACAGGGCC ACGACGGGCG CTCATGTTCT ACATCACTGG
19751 CGCCCACCCC AGCCCCTCCC ACCTTGTGTC GCTGTGAATC GCAGGATCCC
19801 AGCGGCTCAG TCGGACCCTC ATTCCTGAGT AGTCTGAGCC TTAGGTCACC
19851 GTCACCTTCT CAGGCCGGCC CGAGTTTGCA GACTTGTCTG TCTATATCAG
19901 GGTTAGACCA GAGATGCTCT AGACACAGCA GATCACCCAG CCTGTCCTCT
19951 TCTTGATGAC TAAGGACAGG TCCCCTGCCA GGATCGTGAC TCCTTTAGGG
20001 GAGGCCACAG TGACAGGGCA AAGCCTGGAG GGAGAGAGCC ACATGGAGAG
20051 GAGAGGGCTG CCCGCAGAGA GCGTGGGAGT CTGCCGGCTT CTTCTCGAGT
20101 CCTTGGCAAG GTGCTGGCCG CTCACACCGT GTACGTGTGG GGAACGCCCA
20151 GACCAGGGT GACACCACCA GGAGGAGCGG GCGGGACAGT CCCCACTCAG
20201 GGCTAGGAAG AGAGAGTCCA CATTCCCGCT GCCAGGGTGA AACCCTCACA
20251 CCACCACAGA TCCAGGAGAG ACACGGAGGG CACTGCCTCG GGGTGGGGAA
20301 CGTGAGCTGC TCCCCAAACC CAAGAAATGT GTTGAGCCCT ATGCTTCCTT
20351 CCTCGTGGGA AGAGGCGCAA GGTGAGACCG CTTGTCCTTT ATCTTGGCGG
20401 GCACGTCCGA GTGTGACGCA CGTCAGCAAA TCCCTGAACC GTTCATCGGA
20451 GAACAGCCTT CTGCATCTCC CACACTCTGT TCGTGGGTTT ACAGGGTGTC
20501 CAGAGTACTT GCCACTTGGC AATCAGCATT AATAGGATCC ACAGGGCCAG
20551 GCATGGTGGC TCACGCCTGT AATCTCAGCA CTTTGGGAGG CCGAAGCAGG
20601 CGGAGCACCT GAGGTCAGGA GTTCAAGACT GGCGTGGCCA ACATGGTGAA
20651 ACCCGTCTC TACAAAAATT AGCTGGGTAT GGTGGTGGGC ACCTGTAATC
20701 CCAGCTACTT GGGAGGCTGA GGCAGCAGAA TCACTTGAAC CTGGGAGGCG
20751 GAGTTGGCAG TGAGCCAAGA TCACGCCACT GCACTCTAGT CTGGGTGACA
20801 GAGCGAGACC AAAAATAGGA TCCATGGATA GCAGGCAAGA GTGTCCAGGT
20851 GTTCGAGGCA CAGACGACAC TGTGACAGGG AAGAGTCCCC TTAGCCCTGG
20901 CTGGGGCCGT GAAAGCATGC TGTTGTCCGT CTCGGGTGAA CGCAGACTGT
20951 TGTCACGCAT TGCATAACGA TGCTTCCGTC ACTGGCCAAT CGCATGGGGG
21001 GGTGGTCCCG TAAGATGGTA ACACTGGGTT TTGCTGTACG TTTTGTATGT
21051 CTAGATAGGG TTGAGCGTTC TGGTGTGTAC CCACTCACAC GTCCCCTCCG
21101 ACCTTCAGAG CCCAGCTCCC TCCCTCCCAG GGCCTTGGCT GTGACGTGGG
21151 TGACTTCCTA TGGATCTGAG GTTCTGTGGT CCTCACAAGT GGGCATCCTC
21201 TGGCCTCAGC TGCAGGAGGT GGGGGCCCTT TTAATGCCAC CCGAGGCCTG
21251 CGACTCCCTG CACTTTTCAC TGTGACTTGG CTCATCTGGG TCTGTCATTT
21301 GCTCACGCGT TGGTAGTGAC CAACGTCACC ATCCAAGTTC ACGGTCACCA
21351 TAATGATGCT TTCCCCACAC CATGCCAGCG CTGAGCGGCC AGCACCCCCT
21401 CCACCCCACC CACGCCCTCC CCCGACCCCT GCGTCCTGGG AAGTGGTCCT
21451 GCTGCCTGAA GGAAGTAGTC CTGCCTGCCC ATCACACACC AGTAAGGGTG
21501 GGTCCTGCCA GGGGCAGCCT CCGTCCACAA GCTTGCCCTG AGGACCTGCT
21551 TCTAAGACAG CCCTGGTTCC AGGATTCTCT GGGCAGGGCC CCAGAAGCAG
21601 GCCTGGGACA GGTGTGTGTG TGCTGTGATG AGGGGCTGGG AGAACCCGGT
21651 ATGAGACGGG AAAGCCCGG CAAGGAGGTG GTTTCCAGCA AAGTCCCGCA
21701 GAGAACAGCT TCTGCCTGGT CCTGCAGGCC CCACGGAGCA AGTCCAAGCC
21751 ATCCACCCAG AGGCAAGGGA GCTGGGCCTT GGCATCCTCG GGCTTGGGTG
21801 AGTCACCCGC AGAGATGCGA GCTCCCGGG CAGTCTGGCT GCTGGAGGGC
21851 CGGGGCACTT CAAATAGCCC AGAGGCCTGC ATCCAAAGCC ACAGGTGGAG
21901 GCCCGATGGG GATGCCCAGA CACTCACTTG AGGGGACATG GGCGGAACCT
21951 GGACAGCGTC CCCCACGCTC ACGTGTGCCT TTCCATCCAC AGGAGAATGA
22001 CTATCTTCAA GACTGCCTCG ATGCCATCCA GCAAGACTTC GTGATTTTTA
22051 ACAGAGAAAA GTGAGTGTGT TGGGGGTGGG TGGGCGTGGT GGCAGAGAGG
22101 AGGAAAATGG GGCTAAGGTT AAGGTTTTCT TGGCCACGTG AGCGGGCACC
22151 TGTGGGCCTG GGGTGCGTGG CCCTGCTCTC TTTGGGGACT CTGAGCAGCA
```

FIGURE 3F

```
22201 GCTATGGAGG GGAGCGGCGG GAGGCCCCTG CCAGGCTCTG GCATGTTTGT
22251 GCTCCACGCG GGGCCCGTGG CTGGAATCTT CTGGGGAGAG ACACATCATT
22301 TGCCCAGATG AGGGGTGGTG ACTTCCTAGG AGGCCCCATC AGAGCCACGT
22351 CAACTCCCCC ACCCAGGCAC GCCCTCAGTC TCTCAGCAGA CCTTTCCTGA
22401 ATGTCAGGCC CCAGGGGACA GAAAGGGCAC AGATGACTGG CAGCAGGCAA
22451 GGCAGGCCAG AAATAGCAGC AGCTGCCACG GTGGGGCCCA AGGGAGGATG
22501 GATGCTCCCT CTGCCCGCAC GGGGCAAGGA GGGCCTCCTG GAGGAGGTGG
22551 GTCTGAGCTC TTATGGACAG GACGTGCAGG GCAGCACGTG CAGACGGCTG
22601 AGGGCACTGA CTGGCACCCT GGGGATCAGA CGACCGGGTG AAGAATGAGG
22651 CTTAGCCGAG CCTCATTCCC AAGTCACTGA CCTATGGCAC CTGCACAGTC
22701 AGGCCTTTCG GCTTCTGGCT GGAAACATGC CGAGCCTCGC CAGCATGCTC
22751 ACGTGCCCCC ACCCGTCCCC AGGCTCCCTG CCAGTGTGTC GGGAGCATGG
22801 CCTCTCCAGC AGACACCGAG CCTGTGGCCC ACGTTTGGGC ATCCACGCCA
22851 TGGCCTATCC CATGAGCCCG TGGGACCGT GAGGCCAGGG
22901 AGGTGGGGGC ATAACGCCCT CCATGTGTTC CTGCCACCCC AGGCTGAAGA
22951 GGAGCCAGGA CCTCCCGAGG GAGCCTCTCC CCGCCCCTGA GTCCAGGGAT
23001 GCTGCGGAGC CTGTGGAGGA CGAGGCGGAA CGCTCCGCCC TGCCCATGTG
23051 CGGCCCCATT TGCCCCTCGG CCGGGAGCGG CTAGGCCGGG ACGCCCGTGG
23101 TCCTCACCCC TTGAGCTGCT TTGGAGACTC GGCTGCCAGA GGGAGGGCCA
23151 TGGGCCGAGG CCTGGCATTC ACGTTCCCAC CCAGCCTGGC TGGCGGTGCC
23201 CACAGTGCCC CGGACACATT TCACACCTCA GGCTCGTGGT GGTGCAGGGG
23251 ACAAGAGGCT GTGGGTGCAG GGGACACCTG TGGAGGGCAT TTCCCGTGGG
23301 CCCCCGAGAC CCGCTCTAGAT GGAGGAAGCG CTGCTGGGCG CCCTCTTACC
23351 GCTCACGGGG AGCTGGGGCC ATGGATGGGA CAGGAGTCTT TGTCCCTGCT
23401 CAGCCCGGAG GCTGTGCACG GCCCTCGTCA CAAGGTGACC CTTGCAGCAC
23451 AGGCCGCGGG TGCCCCAGGC TCGGCTCAGT TCTTGGAGGT CAAGGGCATG
23501 GGTTGGGGTA GTGGGTGGGG AGGTGAATGT TTTCTAGAGA TTCAAACTGC
23551 TCCAGCAATT TCTGTATAGT TTTCACCTCT GAGAATTACA ATGTGAGAAC
23601 CGCTCGATGT TGCATGTTCT GCGTACGTCC TGTGTCTGCC TGGCCGTCAG
23651 GCCGGTGCCT GCCGTTTCTG GTTGGCCTGG ACTTGGGGCA GCCAGTGGGG
23701 TGGGCAGCTC CTCAGGGCAG AGCTCCGGA CCATGGCTTT GGGGTGGGTG
23751 CCTGTCTCCG TGGCCCTGGA GCCGTAAGGC TGTGGAAGGC AGAGACGGTC
23801 CTGGAGGCAG AGGAGCCCAG GACAGCACCG TGCACCGTGG AGCCGCCGCA
23851 GTGCCGGGCA GTGCTTGGCC CTCCATAAAG GGACGTATCC CTCTCACTGT
23901 GGCTGGGTGG TTCTGTGGTT GGAACTGTAA CTAACTGGGT AAACGGCCTG
23951 TGTGCTTCTC TCTGGTCTCG CTGGAGGAGG ACGGGCTCAG CCCGTCAGCC
24001 CAGCGCTCCA GACAGGCCTG TGCTGGTTTC CTCTGAGGAA ATGGGTGTGG
24051 CGGGTCTGTG CCCCTTCCCA GGACAGCGGC CATAGTGGAC ATGTGCCTAG
24101 ACCTGTGTCC ATGAGCCCCA CTGCACCCCT GGCAAACAGG GCCCTCCCGT
24151 CCTTGGCTGG GCTGCAGATT GGAGATGACA ACGGCCAAAG AACATTTGGG
24201 GAAGAACCGG CCATGCCACG AGCAGAGTCA GAAGTCCGAG GGGATAGAAT
24251 GCAGCTTCCC CTGCCCCAAC CACCCCTGTC CTCTGAATCA TGGCCAGAAAC
24301 TAGCCTTCCA GCCCTCAGCA GCTCACATGG GGGACACGGC ACCCAAATCA
24351 CCACCAGGAA GGGTGGCCCG GTCTCTGCGA GGGCCCAGAG GCGCCGTGTA
24401 CTCGGTGGAA GTCTGGCGAT GTCAGAGACA GGCTCGGGGC AAGGACAGGT
24451 GTGGGGGTTT GAATAAGTGC ATTTGGGGAA CATGGCAGGG TGGTGCACCT
24501 TGTCCTTCTT CGAGACACTG GTGAGGTGTG GGTGCTGTCT GGTTCCCTTG
24551 ATCGCCCCCC ACACTGGGGC AGAGTGGGAG ATGCTGGTGT GGGGGACATC
24601 AGCTCCCACA TCTGGGCCAG AGGGAGCCCC GGGAAGGAAA TGCTGAGGGC
24651 CCAGGGCCTT CGCCTGGGAT CTGCACAGCT TTATAAGCAG CCCAGGGTGA
24701 GAGATGGGCC TGTCTGTGT TCCCAGAGAC CACGGCAGGA AATTCTCTGT
24751 CACCATCGGT GCATGGGCAG GGGCCAGAGA ACCGGTGGCA CAAGGTGTCC
24801 CTGGCTCTCT GCTCAACAAA CAGCGAGTGC CCAGTGACTG CGACCAGGCC
24851 CCGCTCTTGG GATGAGGACA ACCGTCTGGG AACGTCCACG CACCCTTTAT
24901 GAGACACAGC ACGCGCCAGC ACCGCAGTCA CACACCGGGG GCTCGGGTCA
24951 GCCTCATAGC TGCCCGGCCT TGAGTGCTGG GCCTGCGTCT GTGAGCAGCG
25001 CCCACCTGGG TGGCGGTGGT GTGTGCTTCA CTTCCACACA CTCCCGTGCA
25051 TGCTCCCCGG CCTTCTGGGG TGGCTCGGGC TGTCCGGTGA GAATGTAGGC
25101 GGGGGGGGGG GGGGGCCTCT GTCCCGCCCT GGATGTTGGC TGCCCTCTGC
25151 CCCGCCTCTG ATGTTGGCTG CCCTGCCGGC CATCTTCCCT GTGAGAGGGT
25201 GCGCTCCTCC CTGCCATTGA GGGGAGAAGA GCTGCGGCTG CAGGAGTCGT
25251 CGGACCAGCC CACAGCCAGC CAGGCCCCGC CTGTGCAGAG ACGGCGTGGG
25301 GGAGAGGAGA CGGGGCCTTC CTTCCATGCA CAGGCGGCTT CAAACCCAGA
25351 CGTCTTTAAT GGGCCTGATT CACATCAGAG GCAGGATGAC TGCCTGTCCA
25401 GGCGGTGGGT GGCATGCACA GGTTCCTGGC TACAGTGTCC TCAGTGTACA
25451 AAGCTGCTAC TAAGAAGCCT ACGGAAATAC ACAATCTGTA ATAAGAGGAC
25501 AGTGTCTTCC TAAAGGATCG CAAAACTTCC CTGGATGAGG GCTACATGGA
25551 AGCTTAGGTG TGGGCCTTGG GGTGCGTAAA AGGGACCCTC CACGGGCGGG
25601 GCT
(SEQ ID NO: 3)
FEATURES:
Start:    3000
Exon:     3000-3118
```

FIGURE 3G

```
Intron:    3119-4126
Exon:      4127-4300
Intron:    4301-5310
Exon:      5311-5348
Intron:    5349-5478
Exon:      5479-5568
Intron:    5569-5758
Exon:      5759-5862
Intron:    5863-6571
Exon:      6572-6688
Intron:    6689-8108
Exon:      8109-8234
Intron:    8235-8322
Exon:      8323-8454
Intron:    8455-21992
Exon:      21993-22060
Intron:    22061-22942
Exon:      22943-23081
Stop:      23082
```

SNPs:

| DNA Position | Major | Minor | Domain | Protein Position | Major | Minor |
|---|---|---|---|---|---|---|
| 1931 | G | A | Beyond ORF(5') | | | |
| 4232 | G | A | Exon | 75 | T | T |
| 4309 | G | T | Intron | | | |
| 4622 | G | A | Intron | | | |
| 4708 | T | C | Intron | | | |
| 5787 | C | T | Exon | 150 | N | N |
| 5884 | C | T | Intron | | | |
| 8481 | C | T | Intron | | | |
| 8754 | G | A | Intron | | | |
| 8847 | G | A | Intron | | | |
| 11114 | G | A | Intron | | | |
| 19741 | A | G | Intron | | | |
| 20908 | C | T | Intron | | | |
| 22728 | T | C | Intron | | | |
| 23406 | C | T | Beyond ORF(3') | | | |
| 24078 | G | A | Beyond ORF(3') | | | |
| 24777 | G | A | Beyond ORF(3') | | | |

Context:

| DNA Position | |
|---|---|
| 1931 | AGTTCAGTGGTACAGTCGTGGCTCACTGCAGCCTCAACCTCTCAGGCTCAAGCAATCCTC<br>CCTTCTCAGTCTCCTGAGTAGCTGGGACTACGGGTGTGTGCCACCACGCTTTCCGGGCAT<br>GCAGCCAGGAGCCCAGGGCCATCTGTGGCCCACCTTGAGATCCAGAATCATCCATTTCCT<br>CCAGGCCCCCTGCTGGGCTCCAACTCCTTGAGGACCAGAGAGCAGAGGTTGTGGAAGGCC<br>TTGGAAACGGGTCTGGATTACCTGTCCTGGGAAGGTCTCTCCCAACCTGAGTGTCAGACA<br>[G,A]<br>GGGTTAGCTCTGCTGCTCACAATTTTGTGCCTTAATTCCTGGCTTCCCTTTGGGGATCTT<br>CATCCTCAATTCTGATTGACATCCTTGGCCACAAGGGACCCCCCTGCTCATTGATGCTTC<br>TCACCCGTCACCTCACTCTCATCCTCACTGCTAAGCAATTAGCCGTGTGTTTGCGGCATC<br>AGTGTTGACACCGATGATCCATGCTCAGAGGGTACAGGCCTGAAGAGCTATGTGGGGACT<br>GGCGCCCCGGAGGGGGTCCCGCTGTGGTGGCAGCGGTGGCCCCCAAGCCCCACGCTCACT |
| 4232 | CCTCAGGATCTGGGCTCAGAGCTGCTCTGGGCTGGGGTGCAATCAGTGCCTTGGGCAGGC<br>CCCTCCTCCTGGGAATGCCTGGTGGCTGATGCTGGGGTGGGGCTGTGGTCCTTAGGGGGA<br>GTGTGTCAGCTGTGGGAGCAGCCATGACTGGCTCCCCAGCTGTGCGCACAACAGGCCTTC<br>CATCGGTGCCCACAGGTACTCCTTCCAGGACGAGGAGGACATGTTCATGGTCGTGGACCT<br>GCTACTGGGCGGGGACCTGCGCTACCACCTGCAGCAGAACGTGCAGTTCTCCGAGGACAC<br>[G,A]<br>GTGAGGCTGTACATCTGCGAGATGGCACTGGCTCTGGACTACCTGCGCGGCCAGCACATC<br>ATCCACAGGTGTGTGCGTGGCAGACGGCGCAGGTACCTGCTGAGGTGGGCGGGGCTGAAG<br>CAGCCTTAGGTCAGGCTGCCGGCACGGCGGCCGTACTCCCTCAGAGCGGGTCTAGCTCCT<br>CTGCCCCACCCTTGCCTGAGTGCCTGCCCCCAGCTGTGGCACCTGTGCCGACCAGGTCAG<br>CCCCATAGCTGTGTGCCTGGTGTCCATCTGGGGGGACCTCGTCCCAGCAGCCCCAGCTGA |

FIGURE 3H

| | |
|---|---|
| 4309 | CCTGGTGGCTGATGCTGGGGTGGGGCTGTGGTCCTTAGGGGGAGTGTGTCAGCTGTGGGA<br>GCAGCCATGACTGGCTCCCCAGCTGTGCGCACAACAGGCCTTCCATCGGTGCCCACAGGT<br>ACTCCTTCCAGGACGAGGAGGACATGTTCATGGTCGTGGACCTGCTACTGGGCGGGGACC<br>TGCGCTACCACCTGCAGCAGAACGTGCAGTTCTCCGAGGACACGGTGAGGCTGTACATCT<br>GCGAGATGGCACTGGCTCTGGACTACCTGCGCGGCCAGCACATCATCCACAGGTGTGTGC<br>[G,T]<br>TGGCAGACGGCGCAGGTACCTGCTGAGGTGGGCGGGGCTGAAGCAGCCTTAGGTCAGGCT<br>GCCGGCACGGCGGCCGTACTCCCTCAGAGCGGGTCTAGCTCCTCTGCCCCACCCTTGCCT<br>GAGTGCCTGCCCCCAGCTGTGGCACCTGTGCCGACCAGGTCAGCCCCATAGCTGTGTGCC<br>TGGTGTCCATCTGGGGGGACCTCGTCCCAGCAGCCCCAGCTGAGACTGGGCACAGTGGGC<br>TGTTAGCCCTGGTGGACAGACCACCAGGCTGGGTCACAGCAGGTGGCCTTCACCTGGTCC |
| 4622 | CAGGTACCTGCTGAGGTGGGCGGGGCTGAAGCAGCCTTAGGTCAGGCTGCCGGCACGGCG<br>GCCGTACTCCCTCAGAGCGGGTCTAGCTCCTCTGCCCCACCCTTGCCTGAGTGCCTGCCC<br>CCAGCTGTGGCACCTGTGCCGACCAGGTCAGCCCCATAGCTGTGTGCCTGGTGTCCATCT<br>GGGGGGACCTCGTCCCAGCAGCCCCAGCTGAGACTGGGCACAGTGGGCTGTTAGCCCTGG<br>TGGACAGACCACCAGGCTGGGTCACAGCAGGTGGCCTTCACCTGGTCCATTTAACTGAAG<br>[G,A]<br>CTCCTGTTTGCCCATCCACCACATCCCAGGGAATCCAAACTAATTTTTAACATTAGCTTAA<br>AGCAGATGAAATTAGGAAGCAGAGCTGGTGTGATGGCTCTGAAAATAAAATTTAAAAAAA<br>GAAAATAGGAAGCAGATTATGAAGGAAGTGAAATTGGGAAGCAGAAATTAGGCTGAAATT<br>CCGCAGCAATGGAACAAAATGAAAATATCTGTGAGGTATATTTTAAAGTCGAATGGACTG<br>GTGTTTGCATTTCTGCTCTTGGGGACTCGGATGTCTGATTATGACCTAGGCACCAGTCAC |
| 4708 | CTCCTCTGCCCCACCCTTGCCTGAGTGCCTGCCCCCAGCTGTGGCACCTGTGCCGACCAG<br>GTCAGCCCCATAGCTGTGTGCCTGGTGTCCATCTGGGGGGACCTCGTCCCAGCAGCCCCA<br>GCTGAGACTGGGCACAGTGGGCTGTTAGCCCTGGTGGACAGACCACCAGGCTGGGTCACA<br>GCAGGTGGCCTTCACCTGGTCCATTTAACTGAAGACTCCTGTTTGCCCATCCACCACATC<br>CCAGGGAATCCAAACTAATTTTTAACATTAGCTTAAAGCAGATGAAATTAGGAAGCAGAGC<br>[T,C]<br>GGTGTGATGGCTCTGAAAATAAAATTTAAAAAAAAGAAAATAGGAAGCAGATTATGAAGGA<br>AGTGAAATTGGGAAGCAGAAATTAGGCTGAAATTCCGCAGCAATGGAACAAAATGAAAAT<br>ATCTGTGAGGTATATTTTAAAGTCGAATGGACTGGTGTTTGCATTTCTGCTCTTGGGGAC<br>TCGGATGTCTGATTATGACCTAGGCACCAGTCACTGAGCACTGGCTGTGTACCTGGAAAA<br>GTTGGGACAAAGCAAGAGCCGAGGTGGCTTGGTCTCCTAGAGGCCGAGTCTTGGAGGGGG |
| 5787 | CACCTGACCGACTTCAACATTGCCACCATCATCAAGGACGGGGAGCGGGCGACGGCATTA<br>GCAGGCACCAAGCCGTACATGGGTGAGCCCGAGCTGGGGTTCCAGATGGGAGCTGGCTTC<br>CTCCAGGTGGGAAGGACAAGACCTCGGTGGCTTCTCTGTCCCACCCTGGAGGCAGCCTGG<br>TCTCGGGATGTGGCCTCAAGGTGCCGGCCCTGTGCCCACGGGTCCGGGCTGTGACCCCGT<br>GGCAGCTGTTTTTCCTTCTTTCTGTCGGAAAGCTCCGGAGATCTTCCACTCTTTTGTCAA<br>[C,T]<br>GGCGGGACCGGCTACTCCTTCGAGGTGGACTGGTGGTCGGTGGGGGTGATGGCCTATGAG<br>CTGCTGCGAGGATGGGTATGGACCCCCTGCAGCCCCGGGCTTGGCTGCCAGGCCCCTGC<br>TCTCTGCCCCCACCAGTGCTGGGGAGGGGGTGGCTGCCCCAGTGCCCAGGTGCGCAGGGA<br>TGTCTCCACTGTGTCTGAGGAGTCACGCTTTTATCGAAGTGTGTAGTTGGTGATGGAATG<br>CCTGAGCAGGAGGAGGAAGGACAGACTCACTGTGGTTTCCCGGGGCCGCTGCTGGTGCCT |
| 5884 | GGTTCCAGATGGGAGCTGGCTTCCTCCAGGTGGGAAGGACAAGACCTCGGTGGCTTCTCT<br>GTCCCACCCTGGAGGCAGCCTGGTCTCGGGATGTGGCCTCAAGGTGCCGGCCCTGTGCCC<br>ACGGGTCCGGGCTGTGACCCCGTGGCAGCTGTTTTTCCTTCTTTCTGTCGGAAAGCTCCG<br>GAGATCTTCCACTCTTTTGTCAACGGCGGGACCGGCTACTCCTTCGAGGTGGACTGGTGG<br>TCGGTGGGGGTGATGGCCTATGAGCTGCTGCGAGGATGGGTATGGACCCCCTGCAGCCCC<br>[C,T]<br>GGGCTTGGCTGCCAGGCCCCTGCTCTCTGCCCCCACCAGTGCTGGGGAGGGGGTGGCTGC<br>CCCAGTGCCCAGGTGCGCAGGGATGTCTCCACTGTGTCTGAGGAGTCACGCTTTTATCGA<br>AGTGTGTAGTTGGTGATGGAATGCCTGAGCAGGAGGAGGAAGGACAGACTCACTGTGGTT<br>TCCCGGGGCCGCTGCTGGTGCCTGCAGGCCAGCCTCTGTGGGGGTGGACAAGGCTGAGAA<br>CTGGCCAGCAGGGGTGCTGCCTCGGAACTTTCCACAAAAAGTTTCTTTTGGGGCCCTGTG |
| 8481 | GTGCTGTGGGACCACCTGAGCGAGAAGAGGGTGGAGCCGGGCTTCGTGCCCAACGTAAGC<br>CTGTGGGCGGCTCAGGTGGGGGCCCTGGGGATGGATGTGGCGTCCTCCACGGGCCGGGG<br>CTCAGCACCCATCCCTCTGTAGAAAGGCCGTCTGCACTGCGACCCCACCTTTGAGCTGGA<br>GGAGATGATCCTGGAGTCCAGGCCCCTGCACAAGAAGAAGAAGCGCCTGGCCAAGAACAA<br>GTCCCGGGACAACAGCAGGGACAGCTCCCAGTCCGTGAGTGCCAGGGCAGGCTCAGGGCG<br>[C,T]<br>GGCGGCGGGCTGGGCTTGGGGCTCCTCTCTACCACCGAGCAAGGTGTGTGGGGACCCCTG<br>ACAGTGCACACGTCTCGGAAGTCCAGCAGACCGTTTCCTGAAGTCCTGAGAAGGCCAGAG<br>ACCTCCCTTCTGCCTTTCCCAGCCCCCACCTCGCTCCTTATGAAGCAGGTGGGCAGGGAC<br>AACCAGGGCTGGGGTTATGAGTGCACGGGGATGGCCATGTGAAGCCTTCGTGCTTGCCCA<br>GGTGTGCTGGTGTTGGTTGTGTGTGCGGGACGGCTATGTGAAGCCCTCACACTCGCCCA |
| 8754 | CGTGAGTGCCAGGGCAGGCTCAGGGCGCGGCGGCGGGCTGGGCTTGGGGCTCCTCTCTAC<br>CACCGAGCAAGGTGTGTGGGGACCCCTGACAGTGCACACGTCTCGGAAGTCCAGCAGACC |

FIGURE 3I

```
         GTTTCCTGAAGTCCTGAGAAGGCCAGAGACCTCCCTTCTGCCTTTCCCAGCCCCCACCTC
         GCTCCTTATGAAGCAGGTGGGCAGGGACAACCAGGGCTGGGGTTATGAGTGCACGGGGAT
         GGCCATGTGAAGCCTTCGTGCTTGCCCAGGTGTGCTGGTGTTGGTTGTGTGTGCGGGGAC
         [G,A]
         GCTATGTGAAGCCCTCACACTCGCCCAGGTGCGTCGGCATCAGGTATGTGTGCCGGGACA
         GCCATGTGAAGCCCTCACACTCACCCAGGTGCGTCGGCATCAGTTGTGTGTGTGGGGACG
         GCCATGTGAAGCCCTCACACTCGCCCAGGTGTGCTGGCTTTGGTTGTGTGTGCAGGGATG
         GCCACATGAAGCCCTCACACTCGCCCAGGTGCGTCAGCATCAGGTGTGTGTGCGGGGACG
         GCCATGTGAAGCCCTCACACTCGCCCAGGTGCGTTGATGTTGTGTGTGCAGGGATGGCCA

8847     GCACACGTCTCGGAAGTCCAGCAGACCGTTTCCTGAAGTCCTGAGAAGGCCAGAGACCTC
         CCTTCTGCCTTTCCCAGCCCCCACCTCGCTCCTTATGAAGCAGGTGGGCAGGGACAACCA
         GGGCTGGGGTTATGAGTGCACGGGGATGGCCATGTGAAGCCTTCGTGCTTGCCCAGGTGT
         GCTGGTGTTGGTTGTGTGTGCGGGGACGGCTATGTGAAGCCCTCACACTCGCCCAGGTGC
         GTCGGCATCAGGTATGTGTGCCGGGACAGCCATGTGAAGCCCTCACACTCACCCAGGTGC
         [G,A]
         TCGGCATCAGTTGTGTGTGTGGGGACGGCCATGTGAAGCCCTCACACTCGCCCAGGTGTG
         CTGGCTTTGGTTGTGTGTGCAGGGATGGCCACATGAAGCCCTCACACTCGCCCAGGTGCG
         TCAGCATCAGGTGTGTGTGCGGGGACGGCCATGTGAAGCCCTCACACTCGCCCAGGTGCG
         TTGATGTTGTGTGTGCAGGGATGGCCATGTGAAGCCCTCACACTCACCCAGGTGCGTTGA
         TGTCAGTTGTGTGTGCAGGGACAGCCATGTGAAGCCCTCAGACTAGCCCAGGTGTGTCGG

11114    AGACGCATCCCCCCAGCCCCTGCTTCGCTGCCGCGTGGGGTCGGCCTGTGTGTGCGTCTC
         CATCTCCTCCCCTCTTCTCATAAGGGACACCAGGCATTGGATTTAGGGCCCACCCTGATCC
         AGTATGGCCCCCATCTTATCTTGATGATATCTGCAAAGACCTCACTTCCAAATGAGGTCAC
         ATTCACAGGTACCCAGGATTAGAATTTGAGTGTGTCATTTTTGGGGACACAGTTTGGCCC
         ATACCACCAGGATGTGGCTGATATTCACCAAGGAGTAGCTATGGTTGTGTGTTGATGTCA
         [G,A]
         GGTGACGGTGATGACCCTGGGTCCCTCGGTGGTCCCCTTGCCCCTGAGTCTGCCTGAGCC
         TGTGGTGGATGTCCTGGGAAACTCTTGTGCCTCAGCCCCCGTGCAGCCTCCTCAGACCTG
         GTGGGCCCTGTGTTGCTCCTGGGCAGAAGACGGGTGTCAGTCCCCTCCTCACCATGATGT
         GGGGGGCAGGGGTGGGGTCATGCCCTGGGTGCCCTGATTTTGGGGGGAACACGGCCCCCC
         AGTGGGTCAGGCTCCCATCCTCGCCCCTCCTCCAGGACGGCTGCCGGCAGCCCTGGGTGT

19741    GTCAGAGGAAGAGCAGGGCAGATCCAGGCCAGGCACAGACCCTGCCATGGGGTACTGCTG
         GCGGCGCTACACACACCTTGGGAAGGGAGTCCCTGTGGAAAGGGGTCGTGGTCACACATC
         TAGGTGACACAGCCCGGCTTGGGCGCTGCTCAGAGCCACCCCTTCCAGATGGTTCTGGAG
         CAGCTCCTCAGGCTTCTGGTGGCCTCTCTGCCTAGGAAAACATGGCTGTGGACGTTGCAG
         GATGACCAACAGCCCCTGCCACTGGGCTGCACACAGGGCCACGACGGGCGCTCATGTTCT
         [A,G]
         CATCACTGGCGCCCACCCCAGCCCCTCCCACCTTGTGTCGCTGTGAATCGCAGGATCCCA
         GCGGCTCAGTCGGACCCTCATTCCTGAGTAGTCTGAGCCTTAGGTCACCGTCACCTTCTC
         AGGCCGGCCCGAGTTTGCAGACTTGTCTGTCTATATCAGGGTTAGACCAGAGAGTGCTGA
         GACACAGCAGATCACCCAGCCTGTCCTCTTCTTGATGACTAAGGACAGGTCCCCTGCCAG
         GATCGTGACTCCTTTAGGGGAGGCCACAGTGACAGGGCAAAGCCTGGAGGGAGAGAGCCA

20908    CCTGAGGTCAGGAGTTCAAGACTGGCGTGGCCAACATGGTGAAACCCCGTCTCTACAAAA
         ATTAGCTGGGTATGGTGGTGGGCACCTGTAATCCCAGCTACTTGGGAGGCTGAGGCAGCA
         GAATCACTTGAACCTGGGAGGCGGAGTTGGCAGTGAGCCAAGATCACGCCACTGCACTCT
         AGTCTGGGTGACAGAGCGAGACCAAAAATAGGATCCATGGATAGCAGGCAAGAGTGTCCA
         GGTGTTCGAGGCACAGACGACACTGTGACAGGGAAGAGTCCCCTTAGCCCTGGCTGGGGC
         [C,T]
         GTGAAAGCATGCTGTTGTCCGTCTCGGGTGAACGCAGACTGTTGTCACGCATTGCATAAC
         GATGCTTCCGTCACTGGCCAATCGCATGGGGGGTGGTCCCGTAAGATGGTAACACTGGG
         TTTTGCTGTACGTTTTGTATGTCTAGATAGGGTTGAGCGTTCTGGTGTGTACCCACTCAC
         ACGTCCCTCCGACCTTCAGAGCCCAGCTCCCTCCCCAGGGCCTTGGCTGTGACGTG
         GGTGACTTCCTATGGATCTGAGGTTCTGTGGTCCTCACAAGTGGGCATCCTCTGGCCTCA

22728    CACAGATGACTGGCAGCAGGCAAGGCAGGCCAGAAATAGCAGCAGCTGCCACGGTGGGGC
         CCAAGGGAGGATGGATGCTCCCCTCTGCCCGCACGGGGCAAGGAGGGCCTCCTGGAGGAGG
         TGGGTCTGAGCTCTTATGGACAGGACGTGCAGGGCAGCACGTGCAGACGGCTGAGGGCAC
         TGACTGGCACCCTGGGGATCAGACGACCGGGTGAAGAATGAGGCTTAGCCGAGCCTCATT
         CCCAAGTCACTGACCTATGGCACCTGCACAGTCAGGCCTTTCGGCTTCTGGCTGGAAACA
         [T,C]
         GCCGAGCCTCGCCAGCATGCTCACGTGCCCCCACCCGTCCCCAGGCTCCCTGCCAGTGTG
         TCGGGAGCATGGCCTCTCCAGCAGACACCGAGCCTGTGGCCCACGTTTGGGCATCCACGC
         CATGGCCTATCCCATGAGCCCGTGGGCAGGTCATGGGACCGTGAGGCCAGGGAGGTGGGG
         GCATAACGCCCTCCATGTGTTCCTGCCACCCCAGGCTGAAGAGGAGCCAGGACCTCCCGA
         GGGAGCCTCTCCCCGCCCCTGAGTCCAGGGATGCTGCGGAGCCTGTGGAGGACGAGGCGG

23406    ACCCCTTGAGCTGCTTTGGAGACTCGGCTGCCAGAGGGAGGGCCATGGGCCGAGGCCTGG
         CATTCACGTTCCCACCCAGCCTGGCTGGCGGTGCCCACAGTGCCCCGGACACATTTCACA
         CCTCAGGCTCGTGGTGGTGCAGGGGACAAGAGGCTGTGGGTGCAGGGGACACCTGTGGAG
         GGCATTTCCCGTGGGCCCCCGAGACCCGCCTAGATGGAGGAAGCGCTGCTGGGCGCCCTC
```

FIGURE 3J

```
         TTACCGCTCACGGGGAGCTGGGGCCATGGATGGGACAGGAGTCTTTGTCCCTGCTCAGCC
         [C,T]
         GGAGGCTGTGCACGGCCCTCGTCACAAGGTGACCCTTGCAGCACAGGCCGCGGGTGCCCC
         AGGCTCGGCTCAGTTCTTGGAGGTCAAGGGCATGGGTTGGGGTAGTGGGTGGGGAGGTGA
         ATGTTTTCTAGAGATTCAAACTGCTCCAGCAATTTCTGTATAGTTTTCACCTCTGAGAAT
         TACAATGTGAGAACCGCTCGATGTTGCATGTTCTGCGTACGTCCTGTGTCTGCCTGGCCG
         TCAGGCCGGTGCCTGCCGTTTCTGGTTGGCCTGGACTTGGGGCAGCCAGTGGGGTGGGCA
24078    GGCTGTGGAAGGCAGAGACGGTCCTGGAGGCAGAGGAGCCCAGGACAGCACCGTGCACCG
         TGGAGCCGCCGCAGTGCCGGGCAGTGCTTGGCCCTCCATAAAGGGACGTATCCCTCTCAC
         TGTGGCTGGGTGGTTCTGTGGTTGGAACTGTAACTAACTGGGTAAACGGCCTGTGTGCTT
         CTCTCTGGTCTCGCTGGAGGAGGACGGGCTCAGCCCGTCAGCCCAGCGCTCCAGACAGGC
         CTGTGCTGGTTTCCTCTGAGGAAATGGGTGTGGCGGGTCTGTGCCCCTTCCCAGGACAGC
         [G,A]
         GCCATAGTGGACATGTGCCTAGACCTGTGTCCATGAGCCCCACTGCACCCCTGGCAAACA
         GGGCCCTCCCGTCCTTGGCTGGGCTGCGAGATGGAGATGACAACGGCCAAAGAACATTTG
         GGGAAGAACCGGCCATGCCACGAGCAGAGTCAGAAGTCCGAGGGGATAGAATGCAGCTTC
         CCGTCCCCCACCCACCCCTGTCCTCTGAATCATGGCAGAAACTAGCCTTCCAGCCCTCAG
         CAGCTCACATGGGGGACACGGCACCCAAATCACCACCAGGAAGGGTGGCCCGGTCTCTGC
24777    GGAACATGGCAGGGTGGTGCACCTTGTCCTTCTTCGAGACACTGGTGAGGTGTGGGTGCT
         GTCTGGTTCCCTTGATCGCCCCCCACACTGGGGCAGAGTGGGAGATGCTGGTGTGGGGGA
         CATCAGCTCCCACATCTGGGCCAGAGGGAGCCCCGGGAAGGAAATGCTGAGGGCCCAGGG
         CCTTCGCCTGGGATCTGCACAGCTTTATAAGCAGCCCAGGGTGAGAGATGGGCCTGTCTG
         TGGTTCCCAGAGACCACGGCAGGAAATTCTCTGTCACCATCGGTGCATGGGCAGGGGCCA
         [G,A]
         AGAACCGGTGGCACAAGGTGTCCCTGGCTCTCTGCTCAACAAACAGCGAGTGCCCAGTGA
         CTGCGACCAGGCCCCGCTCTTGGGATGAGGACAACCGTCTGGGAACGTCCACGCACCCTT
         TATGAGACACAGCACGCGCCAGCACCGCAGTCACACACCGGGGGCTCGGGTCAGCCTCAT
         AGCTGCCCGGCCTTGAGTGCTGGGCCTGCGTCTGTGAGCAGCGCCCACCTGGGTGGCGGT
         GGTGTGTGCTTCACTTCCACACACTCCCGTGCATGCTCCCCGGCCTTCTGGGGTGGCTCG

Chromosome mapping:
Chromosome 10
```

FIGURE 3K

SEQUENCE LISTING

<160> NUMBER OF SEQ ID NOS: 5

<210> SEQ ID NO 1
<211> LENGTH: 1864
<212> TYPE: DNA
<213> ORGANISM: Human

<400> SEQUENCE: 1

```
cgagtgcgct gctgagtcct gtagataaag ccgccaaccc cggggactgg tgtctcctga      60
gtgaccgtgc agccgtgggc gccatagaaa gcagagaagg cagtgaactt cgaccacttc     120
cagatccttc gggccattgg gaagggcagc tttggcaagg tgtgcattgt gcagaagcgg     180
gacacggaga agatgtacgc catgaagtac atgaacaagc agcagtgcat cgagcgcgac     240
gaggtccgca acgtcttccg ggagctggag atcctgcagg agatcgagca cgtcttcctg     300
gtgaacctct ggtactcctt ccaggacgag gaggacatgt tcatggtcgt ggacctgcta     360
ctgggcgggg acctgcgcta ccacctgcag cagaacgtgc agttctccga ggacacggtg     420
aggctgtaca tctgcgagat ggcactggct ctggactacc tgcgcggcca gcacatcatc     480
cacagagatg tcaagcctga caacattctc ctggatgaga gaggacatgc acacctgacc     540
gacttcaaca ttgccaccat catcaaggac ggggagcggg cgacggcatt agcaggcacc     600
aagccgtaca tggctccgga gatcttccac tcttttgtca acggcgggac cggctactcc     660
ttcgaggtgg actggtggtc ggtgggggtg atggcctatg agctgctgcg aggatggagg     720
ccctatgaca tccactccag caacgccgtg gagtccctgg tgcagctgtt cagcaccgtg     780
agcgtccagt atgtccccac gtggtccaag gagatggtgg ccttgctgcg gaagctcctc     840
actgtgaacc ccgagcaccg gctctccagc ctccaggacg tgcaggcagc cccggcgctg     900
gccggcgtgc tgtgggacca cctgagcgag aagagggtgg agccgggctt cgtgcccaac     960
```

-continued

```
aaaggccgtc tgcactgcga ccccaccttt gagctggagg agatgatcct ggagtccagg    1020
cccctgcaca agaagaagaa gcgcctggcc aagaacaagt cccgggacaa cagcagggac    1080
agctcccagt ccgagaatga ctatcttcaa gactgcctcg atgccatcca gcaagacttc    1140 gtgatttta acagagaaaa gctgaagagg agccaggacc tcccgaggga gcctctcccc     1200
gcccctgagt ccaggatgc tgcggagcct gtggaggacg aggcggaacg ctccgccctg     1260 ccatgtgcg gccccatttg ccctcggcc gggagcggct aggccgggac gcccgtggtc      1320 ctcaccccctt gagctgcttt ggagactcgg ctgccagagg gagggccatg ggccgaggcc   1380
tggcattcac gttcccaccc agcctggctg gcggtgccca cagtgccccg acacatttc     1440 acacctcagg ctcgtggtgg tgcaggggac aagaggctgt gggtgcaggg gacacctgtg    1500
gagggcattt cccgtgggcc cccgagaccc gcctagatgg aggaagcgct gctgggcgcc    1560
ctcttaccgc tcacggggag ctgggccat ggatgggaca ggagtctttg tcctgctca     1620 gcccggaggc tgtgcacggc cctcgtcaca aggtgaccct tgcagcacag gccgcgggtg    1680
ccccaggctc ggctcagttc ttggaggtca agggcatggg ttggggtagt gggtggggag    1740
gtgaatgttt tctagagatt caaactgctc cagcaatttc tgtatagttt tcacctctga    1800
gaattacaat gtgagaaccg cacaaaaaaa aaaaaaaaaa aaaaaaaaaa aaaaaaaaaa    1860
aaaa                                                                1864
```

<210> SEQ ID NO 2
<211> LENGTH: 369
<212> TYPE: PRT
<213> ORGANISM: Human

<400> SEQUENCE: 2

```
Met Tyr Ala Met Lys Tyr Met Asn Lys Gln Gln Cys Ile Glu Arg Asp
 1               5                  10                  15

Glu Val Arg Asn Val Phe Arg Glu Leu Glu Ile Leu Gln Glu Ile Glu
                20                  25                  30

His Val Phe Leu Val Asn Leu Trp Tyr Ser Phe Gln Asp Glu Glu Asp
            35                  40                  45

Met Phe Met Val Asp Leu Leu Leu Gly Gly Asp Leu Arg Tyr His
        50                  55                  60

Leu Gln Gln Asn Val Gln Phe Ser Glu Asp Thr Val Arg Leu Tyr Ile
 65                  70                  75                  80

Cys Glu Met Ala Leu Ala Leu Asp Tyr Leu Arg Gly Gln His Ile Ile
                85                  90                  95

His Arg Asp Val Lys Pro Asp Asn Ile Leu Leu Asp Glu Arg Gly His
                100                 105                 110

Ala His Leu Thr Asp Phe Asn Ile Ala Thr Ile Ile Lys Asp Gly Glu
            115                 120                 125

Arg Ala Thr Ala Leu Ala Gly Thr Lys Pro Tyr Met Ala Pro Glu Ile
        130                 135                 140

Phe His Ser Phe Val Asn Gly Gly Thr Gly Tyr Ser Phe Glu Val Asp
145                 150                 155                 160

Trp Trp Ser Val Gly Val Met Ala Tyr Glu Leu Leu Arg Gly Trp Arg
                165                 170                 175

Pro Tyr Asp Ile His Ser Ser Asn Ala Val Glu Ser Leu Val Gln Leu
            180                 185                 190

Phe Ser Thr Val Ser Val Gln Tyr Val Pro Thr Trp Ser Lys Glu Met
        195                 200                 205
```

-continued

| | | | | | | | | | | | | |
|---|---|---|---|---|---|---|---|---|---|---|---|---|
|Val|Ala|Leu|Leu|Arg|Lys|Leu|Leu|Thr|Val|Asn|Pro|Glu|His|Arg|Leu|
| |210| | | | |215| | | | |220| | | | |

Ser Ser Leu Gln Asp Val Gln Ala Ala Pro Ala Leu Ala Gly Val Leu
225                 230                 235                 240

Trp Asp His Leu Ser Glu Lys Arg Val Glu Pro Gly Phe Val Pro Asn
            245                 250                 255

Lys Gly Arg Leu His Cys Asp Pro Thr Phe Glu Leu Glu Glu Met Ile
            260                 265                 270

Leu Glu Ser Arg Pro Leu His Lys Lys Lys Arg Leu Ala Lys Asn
            275                 280                 285

Lys Ser Arg Asp Asn Ser Arg Asp Ser Ser Gln Ser Glu Asn Asp Tyr
290                 295                 300

Leu Gln Asp Cys Leu Asp Ala Ile Gln Gln Asp Phe Val Ile Phe Asn
305                 310                 315                 320

Arg Glu Lys Leu Lys Arg Ser Gln Asp Leu Pro Arg Glu Pro Leu Pro
            325                 330                 335

Ala Pro Glu Ser Arg Asp Ala Ala Glu Pro Val Glu Asp Glu Ala Glu
            340                 345                 350

Arg Ser Ala Leu Pro Met Cys Gly Pro Ile Cys Pro Ser Ala Gly Ser
            355                 360                 365

Gly

<210> SEQ ID NO 3
<211> LENGTH: 25603
<212> TYPE: DNA
<213> ORGANISM: Human

<400> SEQUENCE: 3

```
gatggagccc aggccacatg cttgggaaag cgggtggtcc tgggtgagcc tgtctggcag     60
gagggtgagg tcctgtctgg agtagacacc cggtctgtgt ccgccgcaca tgtgacaggg    120
cccagagggc acgggaagcc caggtgccct gtcccctggt gagtgggctg tggggggttga   180
gcacccccaag ggaaggcgtg ttcttccaga gattcccccg taagagctga gctgcatcgt   240
gagcaggagg ggcagaggga gcctggagag ggttgggtcg cctgggcagg cagctttctg   300
ggtggtgca caagcgacag aaagcctgag gcttgggacc ggctgaagac ggccttgggc    360
tgcgggtgct ggcgccgctc caggcagagg tgggctctgc agcccccccc ccccgccag    420
cttccccccc agcagcaaga gccctggccc cagccagtgg cccaagcca ggctcctgag    480
gggcagaggg tgaggccgg attttccacc atatttgtct cacagcctgt ctggtcccag    540
ccccagggca caaacagcc tttctggagc agttccaga cctgcagtgg ccgccttgag    600
cctgcagtga ccgtctgcag gaggccgcgg gtgctggggc tggcgcagga agcaccgtt    660
gcttctgcgc ctgtgcagag tgaggctggg gcttccatcc cgggcacggg actcctcggc   720
ctcctgcggc cgtgtgcatg ggaggaaggc cgtgctgccg agccacgcga ctctgccccg   780
ttggcagtgg gaagcggcag gagggggtcc tgccaggggc agcagggagc tgctgcagct   840
tacgctcact gtcattctga aaccctcaac tggctttcaa ataacaatt taaaaatgg    900
tcataggaaa tgcaggaagt tcaggagaaa tcccgcccccg ccccgccctc ccaaggcggc   960
ctcgttcaag cttagtctcc gtctgttctc gggctgcctg cagctgcccc cgctcctcag  1020
caggtgtggc cgcgtgttca ggagcccccaa tcagcacacg cgcctctggg cagccccaa  1080
cacaaggctc ttcctgtccc ttcaggctca gctttcccct cccaccgggc agggaggtgc  1140
```

-continued

| | | |
|---|---|---|
| tgaggccacg cctgttgtca gcttcctgga gaggccatac ttagagccca tggtgccagg | 1200 |
| ccaagccact gtctcccgca ccacagtgct gcagccggat ccacccaggc caccgcttgg | 1260 |
| caccatcaga catgctttct tagtttgggc cagcccggtg ctctgtgcac agtgtgactc | 1320 |
| ccagtggccc cttgcgggag ggagggtcac cgctttgctt cacaaaagga ctgagtctca | 1380 |
| gggaggggtc tccagtaagg gccccggagc caggatgtga ctgagacagg tgcctccagg | 1440 |
| gccacacact aaccagtaca ggaacctctg ggggcagaat catggcctcc aaaacaccca | 1500 |
| catccaaatc ccagaacaaa catgttacca ttcgtggcag agaggaatga agattgcaga | 1560 |
| ttgaattaag gttgttaatc atctgactta attttttag agacagggtc tcgccctgtc | 1620 |
| acccaggctg agttcagtgg tacagtcgtg gctcactgca gcctcaacct ctcaggctca | 1680 |
| agcaatcctc ccttctcagt ctcctgagta gctgggacta cgggtgtgtg ccaccacgct | 1740 |
| ttccgggcat gcagccagga gcccagggcc atctgtggcc caccttgaga tccagaatca | 1800 |
| tccatttcct ccaggccccc tgctgggctc caactccttg aggaccagag agcagaggtt | 1860 |
| gtggaaggcc ttggaaacgg gtctggatta cctgtcctgg gaaggtctct cccaacctga | 1920 |
| gtgtcagaca ggggttagct ctgctgctca caattttgtg ccttaattcc tggcttccct | 1980 |
| ttggggatct tcatcctcaa ttctgattga catccttggc cacaagggac cccctgctc | 2040 |
| attgatgctt ctcacccgtc acctcactct catcctcact gctaagcaat tagccgtgtg | 2100 |
| tttgcggcat cagtgttgac accgatgatc catgctcaga gggtacaggc ctgaagagct | 2160 |
| atgtggggac tggcgccccg gagggggtcc cgctgtggtg gcagcggtgg cccccaagcc | 2220 |
| ccacgctcac tctgtgtgtc tccttgcagg acagggtgag gggccttggc ctcacggtgt | 2280 |
| tgagacggga gtcggtctct ggagtgtgga gtgatgtgcg tccagggtga agctgcagcc | 2340 |
| atggttgatg aggcttcctg agcgcagggc tctgtgctca gtgggttttc gcattcattc | 2400 |
| cccagtaccc ctccgggctg cttgctgctc caagccctgg aaaaggatgt tggggtttag | 2460 |
| gaaggcaaaa ctccatgccc aggtcgtggc tggtgagggg cgctccccgc acaaccagcc | 2520 |
| actgcttggc tccaactcac gcctggatgc tgttaggctg gaccctgtct gtttgcagat | 2580 |
| agcgcctgtt gacagatgtg tcctgctgca gacttgaaac gcaggactga gtctcaggga | 2640 |
| ggggtcttca ctaacagcca tggagccagg atgtcactga gacaggtgcc gccagggcca | 2700 |
| cacactaacc agtacaggaa cctctggggg gcagaatcac ggcctccaaa cacccacat | 2760 |
| cttaatcccc agagcaaata tgttaccata tgtggcagag aggaatgcac ctgccgcgtc | 2820 |
| taggaggcag aggggctgcg gcgcgtcccc aggtgtcccc ttgtgtcctg acgatgcgtc | 2880 |
| cccaggcatc cccatgcatt tccaggtgtc cccacgtgtc cccaggcgtc ctcaggcgtc | 2940 |
| ctgccgaaca gccctgtgcc ctccaggtgt gcattgtgca gaagcgggac acggagaaga | 3000 |
| tgtacgccat gaagtacatg aacaagcagc agtgcatcga gcgcgacgag gtccgcaacg | 3060 |
| tcttccggga gctggagatc ctgcaggaga tcgagcacgt cttcctggtg aacctctggt | 3120 |
| gagcctgcca tggcctcgct gcagaaagac ttaccgtcct gaagccggga aggcactggc | 3180 |
| tatcctctcc tgcccttggt gctccttggc cctcgtgcct cggagatgcc tctgccaccc | 3240 |
| acaggccctc tctagccctc ctcatctatc ccccttcctg tgcccaggc ctggcagtgg | 3300 |
| cccaggtggc catgacatgc tggggttggt taatgcagtg tctcttctga gcctgccgga | 3360 |
| agaccagggc ttccctacaa tggagatgtg ctcccatgga gtctctggca ctagtcagag | 3420 |
| agggagagag tttagggact gaaaaactca ccactgtcat caccatcacc atcaccacca | 3480 |
| tcatcgccat caccaccacc atcaccactg caaccatcat cactctcatc accatcatca | 3540 |

```
ctataatcaa cacaatcact attgtcacca ccattaccac caccaccacg accacaatca   3600
ctgttatcac catcaccacc accctcagtc ctcactaccg tcatcctcac catcaccgtc   3660
accaccacca ccatcactgc catcgtcaac accatggatg ctggttgtta aatgccagct   3720
ctttgcccaa cactgtcaag agtggtacct acacggcctc attttctgta acaaccctcc   3780
gaggcaaatg tctgtatccc cattttaccg aagaggaggc cgggcagcct gaagcacccg   3840
gagctggcac tgtagctctg ctctgcattt gccactccca ggtgcctctg gccccagctg   3900
ggccacctcc agcacaggt ggtgtgtctt tcctcaggat ctgggctcag agctgctctg   3960
ggctggggtg caatcagtgc cttgggcagg cccctcctcc tgggaatgcc tggtggctga   4020
tgctggggtg gggctgtggt ccttaggggg agtgtgtcag ctgtgggagc agccatgact   4080
ggctccccag ctgtgcgcac aacaggcctt ccatcggtgc ccacaggtac tccttccagg   4140
acgaggagga catgttcatg gtcgtggacc tgctactggg cggggacctg cgctaccacc   4200
tgcagcagaa cgtgcagttc tccgaggaca cggtgaggct gtacatctgc gagatggcac   4260
tggctctgga ctacctgcgc ggccagcaca tcatccacag gtgtgtgcgt ggcagacggc   4320
gcaggtacct gctgaggtgg gcggggctga agcagcctta ggtcaggctg ccggcacggc   4380
ggccgtactc cctcagagcg ggtctagctc ctctgcccca cccttgcctg agtgcctgcc   4440
cccagctgtg gcacctgtgc cgaccaggtc agccccatag ctgtgtgcct ggtgtccatc   4500 tgggggggacc tcgtcccagc agcccagct gagactgggc acagtgggct gttagccctg   4560
gtggacagac caccaggctg ggtcacagca ggtggccttc acctggtcca tttaactgaa   4620
gactcctgtt tgcccatcca ccacatccca gggaatccaa actaattta acattagctt   4680 aaagcagatg aaattaggaa gcagagctgg tgtgatggct ctgaaaataa aatttaaaaa   4740
aagaaaatag gaagcagatt atgaaggaag tgaaattggg aagcagaaat taggctgaaa   4800
ttccgcagca atggaacaaa atgaaaatat ctgtgaggta tattttaaag tcgaatggac   4860
tggtgtttgc atttctgctc ttggggactc ggatgtctga ttatgaccta ggcaccagtc   4920
actgagcact ggctgtgtac ctggaaaagt tgggacaaag caagagccga ggtggcttgg   4980
tctcctagag gccgagtctt ggaggggag gcagaccct gccagcaatt gctctcgtcc   5040 tctgggctc caggccccct cccagcatct ggtgccaggt gtgtgctgct gcccagatgc   5100
cacagggaac gaagtggctg acttcatcgc ctctgccccc acgcagggt gtgaggtcct   5160 agcatcatcc aaggaccaag tcaagctccc aggcctctgc ctcgagtggg ttggtgggat   5220
gtcctgggga ctccagggat tgtgacagag attccagggc agaaacaggg cagattccca   5280
actcaccttc ccactttctg ctctttctag agatgtcaag cctgacaaca ttctcctgga   5340
tgagagaggt gtgtggggtt gggtgtgggc agcccaggtg ggtggtggca gggatgggcc   5400
tgtcagggga ggaggatcct gcacgcaagg atgcatctct ggtcctggga cagccacacc   5460
tgacccctct ctgcacagga catgcacacc tgaccgactt caacattgcc accatcatca   5520
aggacgggga gcgggcgacg gcattagcag gcaccaagcc gtacatgggt gagcccgagc   5580
tggggttcca gatgggagct ggcttcctcc aggtgggaag gacaagacct cggtggcttc   5640
tctgtcccac cctggaggca gcctggtctc ggatgtggc ctcaaggtgc cggccctgtg   5700
cccacgggtc cgggctgtga ccccgtggca gctgttttc cttctttctg tcggaaagct   5760
ccggagatct tccactcttt tgtcaacggc gggaccggc actccttcga ggtggactgg   5820
tggtcggtgg gggtgatggc ctatgagctg ctgcgaggat gggtatggac cccctgcagc   5880
```

-continued

| | | | | |
|---|---|---|---|---|
| cccgggctt | ggctgccagg | ccctgctct | ctgccccac | cagtgctggg | gaggggtgg | 5940 |
| ctgccccagt | gcccaggtgc | gcaggatgt | ctccactgtg | tctgaggagt | cacgctttta | 6000 |
| tcgaagtgtg | tagttggtga | tggaatgcct | gagcaggagg | aggaaggaca | gactcactgt | 6060 |
| ggtttcccgg | ggccgctgct | ggtgcctgca | ggccagcctc | tgtggggtg | gacaaggctg | 6120 |
| agaactggcc | agcaggggtg | ctgcctcgga | actttccaca | aaaagtttct | tttgggggccc | 6180 |
| tgtgctctta | cccttgtggc | cacggcgagg | ccagtcctgg | agaccgggag | gctgggggtc | 6240 |
| ctcttgtgga | ccgtacccct | cagccctgca | caggacccca | cctctgagga | agccagctcc | 6300 |
| ctcctggccc | tctggggctg | atctacctgg | acccaggccc | cctgggatcc | cagccagatg | 6360 |
| ggcgcagcag | ccaggcgca | ggacccagcc | gtaagcttta | tctcacccag | gctcctccgc | 6420 |
| ggcaggtgga | ggccaggctg | tgctcagagc | tgtgcctgca | cttgggtgg | ggggagggg | 6480 |
| tcctctcagg | gcgatggcac | ctgtgtctgg | cattgttctg | ggtgtcctgg | gggccaggag | 6540 |
| gacctgccca | gcactgcctc | cctgtctcca | gaggccctat | gacatccact | ccagcaacgc | 6600 |
| cgtggagtcc | ctggtgcagc | tgttcagcac | cgtgagcgtc | cagtatgtcc | ccacgtggtc | 6660 |
| caaggagatg | gtggccttgc | tgcggaaggt | gagcccccat | ccctgagcct | cctcaccctc | 6720 |
| cgagcaccca | cctccctccc | tcacttacct | gcggctcggg | acaccccctc | cagtgcacag | 6780 |
| ttagtgccgc | ttcctggcag | gcacagatcc | cttcactgca | acctgtgggg | gcctccgcag | 6840 |
| atggcagccc | caagcccag | gaagcgagct | ggtggcaggc | tctgtggccc | tctcatggcg | 6900 |
| agccctacca | ggtcactggt | gtcctggtga | tccctgagc | tgcgtctcca | ggcaccctca | 6960 |
| cagcaggctt | gtgcgcccgc | cctgccggtc | accacagagg | agccctgagc | cacgtcccct | 7020 |
| tgtcccacgt | attggaagga | gggtgtcggg | tgggtgggtt | caagcccatg | ctatctccgg | 7080 |
| gaccctttgc | cccagtgcct | cctggggaag | gtgggcagcc | actgcccact | gcaaacacct | 7140 |
| ctcaggggac | atcagcctgg | caggacacg | gcagggtg | tggccatcag | tagtgcctcc | 7200 |
| catttgtgat | ctggtgctag | gctggggctg | tgccttgact | gggctgcaca | gctccctgtt | 7260 |
| ccgagcctcg | cattaacacc | ataggggtt | cggagtcaga | gccaggccca | ggcaggacag | 7320 |
| ggagggagt | gagtgtgcca | cacgggcccg | gctgcctccc | ggccccgtg | tctcaggcag | 7380 |
| gtggggcctc | ctgccctgga | attgtagcca | agcagcctaa | agccttgggg | aggccttgcc | 7440 |
| tgccggggcc | tctccccagc | cccgagagtc | tcttaactct | gctgtagccc | catgaagctc | 7500 |
| agtcacacct | gccaggtgg | ctcacaaggt | ggcactgggc | tagagagggc | ctgcgtgggg | 7560 |
| actggggatg | acccacacgc | ccaagcccag | gtctgggaaa | cctcgcacgg | ggtctgggtc | 7620 |
| tgcggcattt | tccctggaaa | ggcggagagg | gccagcgctg | ggatgttgct | tcccaggcca | 7680 |
| tgcatggctg | ccccgggctc | atctggcctg | tggaggtccc | atgattcggt | gaaggaagtg | 7740 |
| gctctgggat | agttactgtg | aggccagcca | tgtgccgagt | gttagccgct | agccgggcct | 7800 |
| cggctgccac | ctcctggcaa | atcccagcag | agccttccct | gcagatccct | ctgctgtcct | 7860 |
| ctggcgccag | gggtttaggt | agcagcactg | agaacaggcg | tcccttgggc | acatgctga | 7920 |
| gccagccacg | gtgctttgcc | tgatgtcggc | cgtcggcacc | accttcctc | gcgtggccct | 7980 |
| gaggttcctg | aattctgaac | ctgaggcttg | gtgggaccct | cctcaaggtg | ccctggcctg | 8040 |
| ggggtggcgg | gctattccgt | gctggtgggc | tgtgggccct | ggaccctctg | actcatgcct | 8100 |
| ggttgcagct | cctcactgtg | aaccccgagc | accggctctc | cagcctccag | gacgtgcagg | 8160 |
| cagccccggc | gctggccggc | gtgctgtggg | accacctgag | cgagaagagg | gtggagccgg | 8220 |
| gcttcgtgcc | caacgtaagc | ctgtgggcgg | ctcaggtggg | gggccctggg | gatggatgtg | 8280 |

```
gcgtcctcca cgggccgggg ctcagcaccc atccctctgt agaaaggccg tctgcactgc      8340
gaccccacct ttgagctgga ggagatgatc ctggagtcca ggcccctgca caagaagaag      8400
aagcgcctgg ccaagaacaa gtcccgggac aacagcaggg acagctccca gtccgtgagt      8460 gccaggcag gctcagggcg cggcggcggg ctgggcttgg ggctcctctc taccaccgag       8520
caaggtgtgt ggggacccct gacagtgcac acgtctcgga agtccagcag accgtttcct      8580
gaagtcctga gaaggccaga gacctcccct ctgcctttcc cagcccccac ctcgctcctt      8640
atgaagcagg tgggcaggga caaccagggc tggggttatg agtgcacggg gatggccatg      8700
tgaagccttc gtgcttgccc aggtgtgctg gtgttggttg tgtgtgcggg acggctatg      8760 tgaagccctc acactcgccc aggtgcgtcg gcatcaggta tgtgtgccgg acagccatg      8820 tgaagccctc acactcaccc aggtgcgtcg gcatcagttg tgtgtgtggg acggccatg      8880 tgaagccctc acactcgccc aggtgtgctg gctttggttg tgtgtgcagg gatggccaca     8940
tgaagccctc acactcgccc aggtgcgtca gcatcaggtg tgtgtgcggg acggccatg      9000 tgaagccctc acactcgccc aggtgcgttg atgttgtgtg tgcagggatg ccatgtgaa      9060 gccctcacac tcacccaggt gcgttgatgt cagttgtgtg tgcagggaca gccatgtgaa     9120
gccctcagac tagcccaggt gtgtcggtgt cagttgtgtg tgtggggatg ccacgtgaa      9180 gccctcacac ttgcccaggt gcgttgatat tagttgtgtg tgcagggatg ccacgtgaa      9240 gccctcacac tcacccaggt gcgttgatgt cagttgtgag tgtgcgcagg gatggccaca     9300
tgaagccctc agactcgccc aggtgtgctg gctttggttg tgtgcagg acggccatg        9360 tgaagccctc acactcgccc aggtgcgtca gcatcagttg tgtgtgtggg acggccatg      9420 tgaagccctc acactcaccc aggtgtgtcg acatcagttg tgtgtggggg acggccatc      9480 tgaagccctc acactcaccc aggtgtgtcg gtgtcagttg tgtgtgcggg gatggccacg     9540
tgaagccctc acacttgccc aggtgcgttg atattagttg tgtgtgcagg gatggccacg     9600
tgaagccctc acactcaccc aggtgcgttg atgtcagttg tgagtgtgtg cagggatggc     9660
cacgtgaagc cctcagacta gcccaggtgt gctggctttg gttgtgtgtg cagggacggc     9720
catgtgaagc cctcacactc gcccaggtgc gtcagcatca gttgtgtgtg tggggacggc     9780
catgtgaagc cctcacactc gcccaggtgc gtcagcatca gttgtgtgtg tggggatggc     9840
cacgtgaagc cctcagacta gcccaggtgc gtcggcatca ggtgtgtgtg ccgggacagc     9900
cacgtgaagc cctcacactc gcccaggtgt gccggctttg gttgtgtgtg cggggacggc     9960
cacgtgaagc cctcatgctc actcaggcat gctggtattc tggggctgcc aggacaggtg    10020
accacgaatc aggtggttga agaacagcaa tgcgtctctc tgagaggatc tgagtcgtaa    10080
tgaaatggtc tccttcacag ccggctgtgc gtgaactact ctgtctcctg cagctcccct    10140
gtcttgataa ttggctgtct aggcagcggg taaggtgaac cccttgggca gttatgtgat    10200
gatctcagtt tctgtaaacc ggaagtccag gcatggtgca gctctgttcc ctgcttcggg    10260
gtctcaccag aatgtgagct aacattgagg tcgtggcctt gtcaggtgca gctctgtttc    10320
ctgcttctgg gtctccccag agtgtgagct aatattgtct gaggtcgtgg tctcatcagg    10380
gatttgacag gtgctgtggt tgaaatgttt cccttaaaac tcgtgttgga atttgcttcc    10440
tattgtgatg gtggtagaga tgggactttt gggggctgat ggggccacgt aggttcttcc    10500
agcatggatg gggttaatgc tgttgtagaa gggtgacttt agtcctcttt tgagtctttg    10560
atcctctgct atgtgaggac gtggtgttcc caatgtggac gtggttcgtg ttccatgtga    10620
```

| | | | | |
|---|---|---|---|---|
| atgtgatatt | cacaatagag | catcaacagg | ctccctttta | atcagcagat | ttaaaaagaa | 10680 |
| atgtgttgtc | tcatggcttg | gaggcctgag | tccaaagtta | agatgtcagc | aaagccgtgc | 10740 |
| cccctctgaa | ggctctccgg | ggaggaaaac | cagtccttgc | ccctctaccc | tccggtagag | 10800 |
| gctgccttgg | cctagacgca | tccccccagc | ccctgcttcg | ctgccgcgtg | gggtcggcct | 10860 |
| gtgtgtgcgt | ctccatctcc | tcccctcttc | tcataaggac | accaggcatt | ggatttaggg | 10920 |
| cccaccctga | tccagtatgg | ccccatctta | tcttgatgat | atctgcaaag | acctcacttc | 10980 |
| caaatgaggt | cacattcaca | ggtacccagg | attagaattt | gagtgtgtca | ttttgggga | 11040 |
| cacagtttgg | cccataccac | caggatgtgg | ctgatattca | ccaaggagta | gctatggttg | 11100 |
| tgtgttgatg | tcagggtgac | ggtgatgacc | ctgggtccct | cggtggtccc | cttgcccctg | 11160 |
| agtctgcctg | agcctgtggt | ggatgtcctg | ggaaactctt | gtgcctcagc | cccgtgcag | 11220 |
| cctcctcaga | cctggtgggc | cctgtgttgc | tcctgggcag | aagacgggtg | tcagtcccct | 11280 |
| cctcaccatg | atgtgggggg | caggggtggg | gtcatgccct | gggtgccctg | attttggggg | 11340 |
| gaacacggcc | ccccagtggg | tcaggctccc | atcctcgccc | ctcctccagg | acggctgccg | 11400 |
| gcagccctgg | gtgtcctcag | gcagaattgc | tggtggagag | ctgctgtctg | ccaggtggcc | 11460 |
| actgtgaggc | actgctgaga | gccacaggat | ggttggaagg | ttctcggggt | tggggttct | 11520 |
| ttggcattgc | ccccattgga | tgtttaagtt | ttccctacca | gagcatgtcc | agagccaggg | 11580 |
| ctctggggtg | tagaaacagg | cccaggatga | gttaggaacc | ctcatgggag | actcagggat | 11640 |
| ggacagtgtg | cagagcccag | ctggccatgc | tgagttccca | ggaggctctg | gctgggaaca | 11700 |
| ggtaaggcca | ggcacctgtg | agcgggagga | gctcggcttt | gtcttgggtt | ggttgtgtgg | 11760 |
| agatgttttg | gcttgagggt | aggaggtgtt | ctgaaaggaa | agcatcactc | caaaaaaaaa | 11820 |
| gtcccactgt | taaccttgag | gctgagagag | gttttttggaa | acagctttat | tttgatataa | 11880 |
| ttcacattcc | atgcaatata | cagtgcatcc | atgtaaagca | tataattcca | tggttttaa | 11940 |
| tatagtcaca | gggctgtgca | ttctccacca | caatctgatt | ttagaacctt | ttcatgtaat | 12000 |
| gtaagagaaa | gaccccacct | attagcagtc | atgcccccatt | cccctcttct | cccctcccct | 12060 |
| ggcagccacg | aagctacttt | ccgtctctgt | agggttgcct | gttgtgggcg | tttcatggaa | 12120 |
| gtggagttac | acactatgtg | gtctttgcag | ctggcttctt | tcacttcgca | ggatgctttt | 12180 |
| gaggcccgtc | cacgttgtag | cctgtcagtg | cttcattcct | gttgatggct | gagtaatatt | 12240 |
| ccacatatgt | atcaccttc | ctttatccag | tcatcagttg | atgagtattt | gttctttcca | 12300 |
| cttgttaaca | ttttttcatta | tcatgaataa | tgctgctgtg | aacattcaca | tacaagtctt | 12360 |
| tgtgtggata | tgtactttta | ttttggggg | gcacatacct | aggcatgaac | ccgctgggtc | 12420 |
| atatgtgact | ctgtgcttca | tgtttggagg | aaacacctac | ccttttctac | agcaggtgtg | 12480 |
| ccattttatg | cccctaccag | cagtgtgtga | gggttctaat | ttctccatat | atttaccaag | 12540 |
| tcctgttatt | gtctggttta | ttttttttaaa | aatcatagtt | atcttagtgt | gcagtgattg | 12600 |
| tgtggttatg | gtttgcattt | ctctgatgat | attgaacatc | ttttgaggtg | ttttatcagg | 12660 |
| cattgtgtct | agagaaatgt | ctatccaaat | gttttaaaat | ttttattgtc | ttttttttag | 12720 |
| tctactctga | caatatattt | taattggcat | atttatttta | ctttattttt | ttttagagac | 12780 |
| agggtcttgc | tttattacca | aaactggagt | gcagtggtgc | aatgaaggct | cacttcagcc | 12840 |
| ttgacttcct | gggctcaagt | gatcctccct | gccccagctg | ccagaatggc | tggaactgtg | 12900 |
| ggtgtgcacc | accacacctg | gctcatttga | aaaaaatttt | gttgtagaga | cagggtctca | 12960 |
| ctatgttgtc | caggttggtc | tcaaactctt | ggagtcctcc | cacctcagcc | tcccaaaatg | 13020 |

```
ctgggattac agatgtgagc cactgtgcct gacctaattg gtgtatttta gaccattcac    13080
atttaaagcg accagggagg ctgaggcaag aggactgctt gagtccagga gtttgagacc    13140
agcctgggca acaaggtgag acccatctgt attagtctat tttcacactg ctaataaagg    13200
catacctgag tctgggtaat ttatacagga aaaggttta atggatttac agttccacat     13260
ggctggggag gcctcacagt cgtggaaggc aaggaggaga aagtcacatc ttacatggat    13320
ggcggcaggc aaagagagag cttgttcagg gaaacttttg ttttaaaac catcggatct     13380 catgagactc attcactatc atgacaacag cacaggaaag acccgccccc ataattcaat    13440
cacctcccac caggttcctc ccacaacatg tgggaattgt gggagtcaca attcaagctg    13500
agattgggat ggggacagag ccaaaccata tcattctgcc ccagcccctc caaaatctca    13560
tgtcctcaca tttcagaacc aatcatgcct tcccaacagt cccccatagt cttattttgg    13620
cattaactca aaagtccaca gtccaatgtc tcatctgaga caaggtaagt cccttctgcc    13680
tatgagtctg taaaatcaaa agcaagtgac ttcctagata caatagggt acaggcattg     13740 ggtaaattca gccattccaa atgggagaaa ttggccaaaa caaaggggct acaggcccca    13800
tgcaagtctg aaatccagca ggcctgtcaa atcttaaagc ttcaaaatga acatctttga    13860
ctctatctct cacatccagg tcatgctgat gcaagagttg ggttcccatg gtcttaggca    13920
gctctgccct tgtggctctg cagagtacag ccttcctccc ggctgctttc gtgggctggc    13980
attgagtgtc tgtggctttt ccaggtgcat ggtgcaagct gttggtggat ataccattct    14040
ggggtgtaga ggatggtggc cctcttctca gagctccact aggcagtgcc ccagtgggga    14100 cttttgtatag gggcaccaac cccacatttc ccttctgcat tgccctagca gaggttctcc    14160
atgagggccc caccctgca acaaacttct gcctggacat ccaggtgttt ccatacatcc     14220
tctgaaatgc aggcagaggc tcccaaacct caattcttga cttctgtgca cctgcgggct    14280
caacaccaca tggaagctgc cacagcttgg ggcttgtacc ctctgaagcc acagcctgag    14340
ctgtaccttg gccccttca gtcatggctg agcagctgg gatgcagtgc agcaagtccc       14400
tagactgcac acagcagagg gaccctggac ctcgcccatg aaaccatttt ttcctcctag    14460
gcctctgagt ctgtgatggt aggggctgcc gcaaaggtct gtggcatgcc ctggagacat    14520 tttcccatt gtcttggtga ttaatattca gttccttgtt gcttatgcaa atttctcctc     14580
agaaaatggg gttttctttt ttttctctct tttttttttt ttttgagac agtcttgctc     14640 tgtcacccag gctggagtgc agtggtgcaa tggcggctca ttgccactgc aacctccgct    14700
tcctaagttc aagtgattct cctgtctcag cctcccaagt agctgggatt acaggcacgc    14760
accaccacac ccagctaatt tttgtatttt tagtagagaa gggtttcacc atgttggcca    14820
ggctggtctt gaactcctga cctcaggtga tctgcctgcc ttaacctccc aaagtgctag    14880
gattacaggc gtgagccacc gtgcccagcc aggagtttct tttctattgc attgtcaggt    14940
tgcaaatttt ttgaactttt atgctgtttc cttttaaaa tggaatgcct ttaacagcac     15000
ccaagtcacc tcttgaatgc tttgctgctt agaaatttct tctgccacat accctaaatc    15060
atctctcaaa ttcagagttc cacaaatctc tagggcaggg gcaaaatgct gccagtctct    15120
ttgcttaaag cataacaaga gccacctttg ctgtagttcc caacaagttc ctcatctcca    15180
tctgagacca actcagcctg gacttcattg tccatatcat tatcagcatt ttggtcaaag    15240
ccattcaaca agtctctagg aagttccaaa ctttcccaca ttttcctgtc ttcttctgag    15300
ccctccagat ggttccagcc tctgcctatt acccagttct aaaaagttgc ttccacattt    15360
```

```
tcaggtatca tttcagcagc gccctacttt actggtacca atttactgta ttagtctgtt   15420
ctcacgctgc taataaagac atatccgaga ctgggaaatt tatacaggaa aaggtttaa    15480 tggacttaca gttccacatg gctggggagg cctcacaatc atggcggaag caaggagga    15540 gcaagtcaca tcttacatgg atggcagaga gagcttgtgc agggaaactt ttgttttaa    15600 aaccatcaga tctcatgaga ctcattcact atcatgacaa cagcacagga aagacccgcc   15660
cccataattc aatcacctcc cactgggttc ctcccatgac acacgggaat tgtgggagtc   15720
acaattcaag ctgagattgg ggtggggaga cagccaaacc ttatcaccag ctctataaaa   15780
gacaaaaaaa ttaggcaggc ataacagtgc atgcctgtag ttccagtgat gtgagaggat   15840
tgcttgagtc caggagtttg agaccaggct gggcaacatg gcgagaccct gtctctacaa   15900
aaaaaaatta tctgggtgtg gtgggataca cctgtgatac cagctacgca ggaggctgag   15960
gcagtaggat tgcttgagcc caggagttca aggctgcagt aagctatgat catgcccctg   16020
cactccagtc tgggtaacag agagacacgc tgtcttgtaa ataaataagt ggtcatttat   16080
atagttcaat atgatatcta ccttatttgt aactgtagtc tatttattgg tcttcctttt   16140
tccctatttt tctgccttt ctggttttaa ttaagcattt tatattattc tagtttatct    16200
cctctcctgg cctgttaatt atacttcttt tgaaatatt tttagtggtt ggcctggaca    16260
ttgcagtata cctttaccat acagtctacc ttcacctgac actctgcccc ctcatgtgca   16320
gtgggatgcc ttgtgacggc acctctcgtg caatcctcct gttcctgatg acattgctgt   16380
cattcatttc atttatctgt atgctataat tgctcattac attgttacta ctgttatttt   16440
aaacagttat ctttttggatc aattaagaaa aattaaaaat ttcattttac ctctattcat   16500
tcctcctcta aagtgcttcc tttctttatg cagacccaag ttgctgacct aaatcatttt   16560
cctttcccct gaggaacttc gtttaacatg tcttatagga caggtccaac agagatgaat   16620
tccttccctt tttgtttgtc caaaaaagtc tttactttca cctttaaaga ataatttcac   16680
tggatataga attctagatt ggtaggtttt ttactttcaa cactttaaat atttcactcc   16740
gctctcttct tgcttatgtg atttctaaca ggcagtctgc tctaattctt tttctgtaag   16800
tagaattcct cgccaccccc caccccagc tcatttcaag attttctctg tctttggttt    16860
tctgcaattt gaataatgat atgcctaggt acagattttt ttttaatatt cattctgctt   16920
ggtgttctct gagcttctta gatctgtggt ttggtgtctg tcattaattt cagaaaattc   16980
ccagtcatta ttatttcaaa tattctgttc tctttctctt ctcctgctgg aaatccaatt   17040
atgtgtgtgt ggtgccgttt gaaattgtcc cacagctctt ggatattctg ttcatttttt   17100
tcactctttt tttttttctct ttgcatttca gttcgagaag tttctgttga catttcttca   17160
agctcataga tccttcctca tctggatcca gtctactgag gaaccatcaa aggcatcctc   17220
atttctgtta cagtgttttc tacttccagc atttcctttt gatccctcct tggagtttcc   17280
atctctctac ttacattgcc cttctgttcc ccatctgttc ttgcctgctt ttcccctgga   17340
gcccttgcca tattaatcac agttatttca aatttcctgt ttgataattc caacatgggt   17400
gccatatctg gatctgttct aatgtgtgca ttgtctcttc acactctatt tttttcctta   17460
agaccttgta gtctgccttg taatgtttgt tgaaagctgg acgtgatgta tctggtaata   17520
agagctgaag tagatgggcc tttagtgtga ggtttatgta atctggccag gtttggggca   17580
gggtttaaag tctgctgtag ctgtgggtac cagaggcttc acatttgttt tcatttcccg   17640
ggttgccctt gggcttgcct aaatcctcct cctcagagag agtctgcgtc ttgtggccct   17700
ctctgctgga atccctgtca cactgcggag gccctgtggg tgtgttggga agatggtggg   17760
```

-continued

```
gagggaactg ttccacagtc tgtgaccaaa tctcagtctt gggggcctgt gcccttcac    17820 agttgttgat ctgcttttcc cctcccctta ggtgagacag gctaaagcgg ggtacaggct    17880
gaaaaacagt cctcccccaa gtgagataag cctttccttt ggagagcaaa ttccatttgc    17940
tgtggagaat gctctggtg tatttcacag tggtgactgt ccccatccca tgccagagcc     18000
aggaagggat catccttggc ttcattaaga cctggcaggg ttcctggagg ggaaacccac    18060
aaaacgttgg gggcctcata agaccgcagc cgcaggagtt ctgcacacgg ccccggccgc    18120
tccccagagc tgcccaggag gtgttcccgc acaccatcag ttctgctcca ggccagcagg    18180
tctcagctgt gactttgctc acctgtctct ccagacttgg gggtcgccgc agcgctttga    18240
cctcagctct ctgatgggtc caggaaaagt aattgatttt cattagttca gcattttcc    18300 tgtcgcaggg atgggagtga ggccttccac gttgtttgcc gcagagcaga agccagaagt    18360
ccttgctcgt ctctgtgttt cttcgtcgga gtcatgtctt ttatttcctg aacgcaggtg    18420
tgtggtcaga caggagattg gcaggtattt cctcctgttc catgggctat cttttctctt    18480
tcttgagggc atcatttgca gcaggaagt cttggacctt gacgttgtcc gatgtggctg     18540
tttcctcctt ggctgctctg ctttgtctaa ggatccatca cctcagctga ggccacaggg    18600
atttactccc acactttctt ctaagtcttg tatagtttca gctcttgcgt ttagctgtgt    18660
gattcatttt gggttaattt ttatgaacaa tgtcaggtga gggtccagct tcattctctc    18720
atcggtggat atctgactgt cctagcacca tttgctgaag agaggattct ttccccattg    18780
aattgctttt gacatcatac cttgtttttt gacttgccgt tttatcccat tggtccagac    18840
gtctgccctg cgccgggact gcaccatctt gataactgta gctttgtagc aagctttcaa    18900
atcaggatct gtgaatcccc cagttttgtt ctttttggac attatttgac tattctgggt    18960
ccctggcatt tccactgaat gctgaggggt ctgacagttg catctgagct gccaagcagg    19020
tttgtggcgg tgctagggac tgaagcctgc tccatttccc aggcccctcc tcgctgtggg    19080
tgacatctgg ggtccgaggc tgtgtctcag catgtgtgaa ggtgccacgg gtgccctgag    19140 atgggattc ctggtccagt tactcagaaa gtgcatccag gagagacccc cgcccttctc     19200
gggatgggag atgccagcag agcttggctt tcaagcagaa atctggaaac cctgtgggga    19260
gtggcttcgg acttcagggg acctggagcg tcacttgtgg ttcaagaggt ccctgccctg    19320
agggagctgg gctctcaaac acccacacca gtcagtcatg ggcgaagggc cctctgtgg    19380 ccttctgact gtgtgtgtgc tggcaaaggg ttccagccac ccaaggagga ggcaggggct    19440
gtcagaggaa gagcagggca gatccaggcc aggcacagac cctgccatgg ggtactgctg    19500
gcggcgctac acacaccttg ggaagggagt ccctgtggaa aggggtcgtg gtcacacatc    19560
taggtgacac agcccggctt gggcgctgct cagagccacc ccttccagat ggttctggag    19620
cagctcctca ggcttctggt ggcctctctg cctaggaaaa catggctgtg gacgttgcag    19680
gatgaccaac agcccctgcc actgggctgc acacagggcc acgacgggcg ctcatgttct    19740
acatcactgg cgcccacccc agcccctccc accttgtgtc gctgtgaatc gcaggatccc    19800
agcggctcag tcggaccctc attcctgagt agtctgagcc ttaggtcacc gtcaccttct    19860
caggccggcc cgagtttgca gacttgtctg tctatatcag ggttagacca gagagtgctg    19920
agacacagca gatcacccag cctgtcctct tcttgatgac taaggacagg tccctgcca    19980 ggatcgtgac tccttaggg gaggccacag tgacagggca aagcctggag ggagagagcc     20040
acatggagag gagagggctg cccgcagaga gcgtgggagt ctgccggctt cttctcgagt    20100
```

```
ccttggcaag gtgctggccg ctcacaccgt gtacgtgtgg ggaacgccca ggaccagggt   20160
gacaccacca ggaggagcgg gcgggacagt ccccactcag ggctaggaag agagagtcca   20220
cattcccgct gccagggtga aaccctcaca ccaccacaga tccaggagag acacggaggg   20280
cactgcctcg gggtggggaa cgtgagctgc tccccaaacc caagaaatgt gttgagccct   20340
atgcttcctt cctcgtggga agaggcgcaa ggtgagaccg cttgtccttt atcttggcgg   20400
gcacgtccga gtgtgacgca cgtcagcaaa tccctgaacc gttcatcgga gaacagcctt   20460
ctgcatctcc cacactctgt tcgtgggttt acagggtgtc cagagtactt gccacttggc   20520
aatcagcatt aataggatcc acagggccag gcatggtggc tcacgcctgt aatctcagca   20580
ctttgggagg ccgaagcagg cggagcacct gaggtcagga gttcaagact ggcgtggcca   20640
acatggtgaa accccgtctc tacaaaaatt agctgggtat ggtggtgggc acctgtaatc   20700
ccagctactt gggaggctga ggcagcagaa tcacttgaac ctgggaggcg gagttggcag   20760
tgagccaaga tcacgccact gcactctagt ctgggtgaca gagcgagacc aaaaatagga   20820
tccatggata gcaggcaaga gtgtccaggt gttcgaggca cagacgacac tgtgacaggg   20880
aagagtcccc ttagccctgg ctggggccgt gaaagcatgc tgttgtccgt ctcgggtgaa   20940
cgcagactgt tgtcacgcat tgcataacga tgcttccgtc actggccaat cgcatggggg   21000
ggtggtcccg taagatggta acactgggtt ttgctgtacg ttttgtatgt ctagataggg   21060
ttgagcgttc tggtgtgtac ccactcacac gtcccctccg accttcagag cccagctccc   21120
tccctcccag ggccttggct gtgacgtggg tgacttccta tggatctgag gttctgtggt   21180
cctcacaagt gggcatcctc tggcctcagc tgcaggaggt gggggcccctt ttaatgccac   21240 ccgaggcctg cgactccctg cacttttcac tgtgacttgg ctcatctggg tctgtcattt   21300
gctcacgcgt tggtagtgac caacgtcacc atccaagttc acggtcacca taatgatgct   21360
ttccccacac catgccagcg ctgagcggcc agcacccccct ccaccccacc cacgccctcc   21420
cccgacccct gcgtcctggg aagtggtcct gctgcctgaa ggaagtagtc ctgcctgccc   21480
atcacacacc agtaagggtg ggtcctgcca ggggcagcct ccgtccacaa gcttgccctg   21540
aggacctgct tctaagacag ccctggttcc aggattctct gggcagggcc ccagaagcag   21600
gcctgggaca ggtgtgtgtg tgctgtgatg aggggctggg agaacccggt atgagacggg   21660
aaaggcccgg caagggagtg gtttccagca aagtcccgca gagaacagct tctgcctggt   21720
cctgcaggcc ccacggagca agtccaagcc atccacccag aggcaaggga gctgggcctt   21780
ggcatcctcg ggcttgggtg agtcacccgc agagatgcga gctccccggg cagtctggct   21840
gctggagggc cggggcactt caaatagccc agaggccgtc atccaaagcc acaggtggag   21900
gcccgatggg gatgcccaga cactcacttg aggggacatg ggcggaacct ggacagcgtc   21960
ccccacgctc acgtgtgcct ttccatccac aggagaatga ctatcttcaa gactgcctcg   22020
atgccatcca gcaagacttc gtgattttta acagagaaaa gtgagtgtgt tggggtgggt   22080
tgggcgtggt ggcagagagg aggaaaatgg ggctaaggtt aaggttttct tggccacgtg   22140
agcgggcacc tgtgggcctg gggtgcgtgg ccctgctctc tttggggact ctgagcagca   22200
gctatggagg ggagcggcgg gaggcccctg ccaggctctg gcatgtttgt gctccacgcg   22260
gggcccgtgg ctggaatctt ctggggagag acacatcatt tgcccagatg aggggtggtg   22320
acttcctagg aggccccatc agagccacgt caactccccc acccaggcac gccctcagtc   22380
tctcagcaga ccttttcctga atgtcaggcc ccaggggaca gaaagggcac agatgactgg   22440
cagcaggcaa ggcaggccag aaatagcagc agctgccacg gtggggccca agggaggatg   22500
```

```
gatgctccct ctgcccgcac ggggcaagga gggcctcctg gaggaggtgg gtctgagctc    22560
ttatggacag gacgtgcagg gcagcacgtg cagacggctg agggcactga ctggcaccct    22620
ggggatcaga cgaccgggtg aagaatgagg cttagccgag cctcattccc aagtcactga    22680
cctatggcac ctgcacagtc aggcctttcg gcttctggct ggaaacatgc cgagcctcgc    22740
cagcatgctc acgtgccccc acccgtcccc aggctccctg ccagtgtgtc gggagcatgg    22800
cctctccagc agacaccgag cctgtggccc acgtttgggc atccacgcca tggcctatcc    22860
catgagcccg tgggcaggtc atgggaccgt gaggccagga aggtggggc ataacgccct    22920 ccatgtgttc ctgccacccc aggctgaaga ggagccagga cctcccgagg gagcctctcc    22980
ccgcccctga gtccagggat gctgcggagc ctgtggagga cgaggcggaa cgctccgccc    23040
tgcccatgtg cggccccatt tgcccctcgg ccgggagcgg ctaggccggg acgcccgtgg    23100
tcctcacccc ttgagctgct ttggagactc ggctgccaga gggagggcca tgggccgagg    23160
cctggcattc acgttcccac ccagcctggc tggcggtgcc cacagtgccc cggacacatt    23220
tcacacctca ggctcgtggt ggtgcagggg acaagaggct gtgggtgcag gggacacctg    23280
tggagggcat ttcccgtggg cccccgagac ccgcctagat ggaggaagcg ctgctgggcg    23340
ccctcttacc gctcacgggg agctgggggcc atggatggga caggagtctt tgtccctgct    23400
cagcccggag gctgtgcacg gccctcgtca aaggtgacc cttgcagcac aggccgcggg    23460
tgccccaggc tcggctcagt tcttggaggt caagggcatg ggttgggta gtgggtgggg    23520 aggtgaatgt tttctagaga ttcaaactgc tccagcaatt tctgtatagt tttcacctct    23580
gagaattaca atgtgagaac cgctcgatgt tgcatgttct gcgtacgtcc tgtgtctgcc    23640
tggccgtcag gccggtgcct gccgtttctg gttggcctgg acttggggca gccagtgggg    23700
tgggcagctc ctcagggcag agctcccgga ccatggcttt ggggtgggtg cctgtctccg    23760
tggccctgga gccgtaaggc tgtggaaggc agagacggtc ctggaggcag aggagcccag    23820
gacagcaccg tgcaccgtgg agccgccgca gtgccgggca gtgcttggcc ctccataaag    23880
ggacgtatcc ctctcactgt ggctgggtgg ttctgtggtt ggaactgtaa ctaactgggt    23940
aaacggcctg tgtgcttctc tctggtctcg ctggaggagg acgggctcag cccgtcagcc    24000
cagcgctcca gacaggcctg tgctggtttc ctctgaggaa atgggtgtgg cgggtctgtg    24060
ccccttccca ggacagcggc catagtggac atgtgcctag acctgtgtcc atgagcccca    24120
ctgcacccct ggcaaacagg gccctcccgt ccttggctgg gctgcgagat ggagatgaca    24180
acggccaaag aacatttggg gaagaaccgg ccatgccacg agcagagtca gaagtccgag    24240
gggatagaat gcagcttccc gtcccccacc caccctgtc ctctgaatca tggcagaaac    24300
tagccttcca gccctcagca gctcacatgg gggacacggc acccaaatca ccaccaggaa    24360
gggtggcccg gtctctgcga gggcccagag gcgccgtgta ctcggtggaa gtctggcgat    24420
gtcagagaca ggctcgggc aaggacaggt gtgggggttt gaataagtgc atttggggaa    24480
catggcaggt tggtgcacct tgtccttctt cgagacactg gtgaggtgtg ggtgctgtct    24540
ggttcccttg atcgcccccc acactgggc agagtgggag atgctggtgt gggggacatc    24600
agctcccaca tctgggccag agggagcccc ggggaaggaaa tgctgagggc ccaggacctt    24660
cgcctgggat ctgcacagct ttataagcag cccagggtga gagatgggcc tgtctgtggt    24720
tcccagagac cacggcagga aattctctgt caccatcggt gcatgggcag gggccagaga    24780
accggtggca caaggtgtcc ctggctctct gctcaacaaa cagcgagtgc ccagtgactg    24840
```

-continued

```
cgaccaggcc ccgctcttgg gatgaggaca accgtctggg aacgtccacg cacccttat    24900 gagacacagc acgcgccagc accgcagtca cacaccgggg gctcgggtca gcctcatagc    24960
tgcccggcct tgagtgctgg gcctgcgtct gtgagcagcg cccacctggg tggcggtggt    25020
gtgtgcttca cttccacaca ctcccgtgca tgctccccgg ccttctgggg tggctcgggc    25080
tgtccggtga gaatgtaggc gggggggggg ggggcctct gtcccgccct ggatgttggc    25140
tgccctctgc cccgccctgg atgttggctg ccctgccggc catcttccct gtgagagggt    25200
gcgctcctcc ctgccattga ggggagaaga gctgcggctg caggagtcgt cggaccagcc    25260
cacagccagc caggccccgc ctgtgcagag acggcgtggg ggagaggaga cggggccttc    25320
cttccatgca caggcggctt caaacccaga cgtctttaat gggcctgatt cacatcagag    25380
gcaggatgac tgcctgtcca ggcggtgggt ggcatgcaca ggttcctggc tacagtgtcc    25440
tcagtgtaca aagctgctac taagaagcct acgaaatac acaatctgta ataagaggac    25500
agtgtcttcc taaaggatcg caaaacttcc ctggatgagg gctacatgga agcttaggtg    25560
tgggccttgg ggtgcgtaaa agggaccctc cacgggcggg gct                      25603
```

```
<210> SEQ ID NO 4
<211> LENGTH: 399
<212> TYPE: PRT
<213> ORGANISM: Mus musculus

<400> SEQUENCE: 4

Val Asn Phe Asp His Phe Gln Ile Leu Arg Ala Ile Gly Lys Gly Ser
 1               5                  10                  15

Phe Gly Lys Val Cys Ile Val Gln Lys Arg Asp Thr Glu Lys Met Tyr
                20                  25                  30

Ala Met Lys Tyr Met Asn Lys Gln Gln Cys Ile Glu Arg Asp Glu Val
            35                  40                  45

Arg Asn Val Phe Arg Glu Leu Glu Ile Leu Gln Glu Ile Glu His Val
        50                  55                  60

Phe Leu Val Asn Leu Trp Tyr Ser Phe Gln Asp Glu Glu Asp Met Phe
    65                  70                  75                  80

Met Val Val Asp Leu Leu Leu Gly Gly Asp Leu Arg Tyr His Leu Gln
                85                  90                  95

Gln Asn Val Gln Phe Ser Glu Asp Thr Val Arg Leu Tyr Ile Cys Glu
                100                 105                 110

Met Ala Leu Ala Leu Asp Tyr Leu Arg Ser Gln His Ile Ile His Arg
            115                 120                 125

Asp Val Lys Pro Asp Asn Ile Leu Leu Asp Glu Gln Gly His Ala His
        130                 135                 140

Leu Thr Asp Phe Asn Ile Ala Thr Ile Ile Lys Asp Gly Glu Arg Ala
145                 150                 155                 160

Thr Ala Leu Ala Gly Thr Lys Pro Tyr Met Ala Pro Glu Ile Phe His
                165                 170                 175

Ser Phe Val Asn Gly Gly Thr Gly Tyr Ser Phe Glu Val Asp Trp Trp
                180                 185                 190

Ser Val Gly Val Met Ala Tyr Glu Leu Leu Arg Gly Trp Arg Pro Tyr
            195                 200                 205

Asp Ile His Ser Ser Asn Ala Val Glu Ser Leu Val Gln Leu Phe Ser
        210                 215                 220

Thr Val Ser Val Gln Tyr Val Pro Thr Trp Ser Lys Glu Met Val Ala
225                 230                 235                 240
```

```
Leu Leu Arg Lys Leu Leu Thr Val Asn Pro Glu His Arg Phe Ser Ser
            245                 250                 255

Leu Gln Asp Met Gln Thr Ala Pro Ser Leu Ala His Val Leu Trp Asp
            260                 265                 270

Asp Leu Ser Glu Lys Lys Val Glu Pro Gly Phe Val Pro Asn Lys Gly
            275                 280                 285

Arg Leu His Cys Asp Pro Thr Phe Glu Leu Glu Met Ile Leu Glu
            290                 295                 300

Ser Arg Pro Leu His Lys Lys Lys Arg Leu Ala Lys Asn Lys Ser
305                 310                 315                 320

Arg Asp Ser Ser Arg Asp Ser Ser Gln Ser Glu Asn Asp Tyr Leu Gln
            325                 330                 335

Asp Cys Leu Asp Ala Ile Gln Gln Asp Phe Val Ile Phe Asn Arg Glu
            340                 345                 350

Lys Leu Lys Arg Ser Gln Glu Leu Met Ser Glu Pro Pro Gly Pro
            355                 360                 365

Glu Thr Ser Asp Met Thr Asp Ser Thr Ala Asp Ser Glu Ala Glu Pro
            370                 375                 380

Thr Ala Leu Pro Met Cys Gly Ser Ile Cys Pro Ser Ser Gly Ser
385                 390                 395
```

<210> SEQ ID NO 5
<211> LENGTH: 368
<212> TYPE: PRT
<213> ORGANISM: Macaca fascicularis

<400> SEQUENCE: 5

```
Met Tyr Ala Met Lys Tyr Met Asn Lys Gln Gln Cys Ile Glu Arg Asp
  1               5                  10                  15

Glu Val Arg Asn Val Phe Arg Glu Leu Gly Ile Leu Gln Glu Ile Glu
             20                  25                  30

His Val Phe Leu Val Asn Leu Trp Tyr Ser Phe Gln Asp Glu Glu Asp
             35                  40                  45

Met Phe Met Val Val Asp Leu Leu Gly Gly Asp Leu Arg Tyr His
         50                  55                  60

Leu Gln Gln Asn Val Gln Phe Ser Glu Asp Thr Val Arg Leu Tyr Ile
65                  70                  75                  80

Cys Glu Met Ala Leu Ala Leu Asp Tyr Leu Cys Gly Gln His Ile Ile
             85                  90                  95

His Arg Asp Val Lys Pro Asp Asn Ile Leu Leu Asp Glu Arg Gly His
            100                 105                 110

Ala His Leu Thr Asp Phe Asn Ile Ala Thr Ile Ile Lys Asp Gly Glu
            115                 120                 125

Arg Ala Thr Ala Leu Ala Gly Thr Lys Pro Tyr Met Ala Pro Glu Ile
            130                 135                 140

Phe His Ser Phe Val Asn Gly Gly Thr Gly Tyr Ser Phe Glu Val Asp
145                 150                 155                 160

Trp Trp Ser Leu Gly Val Met Ala Tyr Glu Leu Leu Arg Gly Trp Arg
            165                 170                 175

Pro Tyr Asp Ile His Ser Ser Asn Ala Val Glu Ser Leu Val Gln Leu
            180                 185                 190

Phe Ser Thr Val Ser Val Gln Tyr Val Pro Thr Trp Ser Arg Glu Met
            195                 200                 205

Val Ala Leu Leu Arg Lys Leu Leu Thr Val Asn Pro Glu His Arg Phe
            210                 215                 220
```

```
Ser Ser Leu Gln Asp Val Gln Ala Ala Pro Ala Leu Ala Gly Val Leu
225                 230                 235                 240

Trp Gly His Leu Ser Glu Lys Arg Val Glu Pro Asp Phe Val Pro Asn
                245                 250                 255

Lys Gly Arg Leu His Cys Asp Pro Thr Phe Glu Leu Glu Glu Met Ile
                260                 265                 270

Leu Glu Ser Arg Pro Leu His Lys Lys Lys Arg Leu Ala Lys Asn
            275                 280                 285

Lys Ser Arg Asp Asn Ser Arg Asp Ser Ser Gln Ser Glu Asn Asp Tyr
            290                 295                 300

Leu Gln Asp Cys Leu Asp Ala Ile Gln Gln Asp Phe Val Ile Phe Asn
305                 310                 315                 320

Arg Glu Lys Leu Lys Arg Ser Gln Asp Leu Pro Ser Glu Pro Leu Pro
                325                 330                 335

Ala Pro Glu Pro Arg Asp Ala Ala Glu Pro Val Glu Asp Glu Glu Gln
                340                 345                 350

Ser Ala Leu Pro Met Cys Gly Pro Ile Cys Pro Ser Ala Gly Ser Gly
            355                 360                 365
```

ISOLATED HUMAN KINASE PROTEINS, NUCLEIC ACID MOLECULES ENCODING HUMAN KINASE PROTEINS, AND USES THEREOF

RELATED APPLICATIONS

The present application claims priority to provisional application U.S. Ser. No. 60/263,162, filed Jan. 23, 2001.

FIELD OF THE INVENTION

The present invention is in the field of kinase proteins that are related to the serine/threonine protein kinase subfamily, recombinant DNA molecules, and protein production. The present invention specifically provides novel peptides and proteins that effect protein phosphorylation and nucleic acid molecules encoding such peptide and protein molecules, all of which are useful in the development of human therapeutics and diagnostic compositions and methods.

BACKGROUND OF THE INVENTION

Protein Kinases

Kinases regulate many different cell proliferation, differentiation, and signaling processes by adding phosphate groups to proteins. Uncontrolled signaling has been implicated in a variety of disease conditions including inflammation, cancer, arteriosclerosis, and psoriasis. Reversible protein phosphorylation is the main strategy for controlling activities of eukaryotic cells. It is estimated that more than 1000 of the 10,000 proteins active in a typical mammalian cell are phosphorylated. The high energy phosphate, which drives activation, is generally transferred from adenosine triphosphate molecules (ATP) to a particular protein by protein kinases and removed from that protein by protein phosphatases. Phosphorylation occurs in response to extracellular signals (hormones, neurotransmitters, growth and differentiation factors, etc), cell cycle checkpoints, and environmental or nutritional stresses and is roughly analogous to turning on a molecular switch. When the switch goes on, the appropriate protein kinase activates a metabolic enzyme, regulatory protein, receptor, cytoskeletal protein, ion channel or pump, or transcription factor.

The kinases comprise the largest known protein group, a superfamily of enzymes with widely varied functions and specificities. They are usually named after their substrate, their regulatory molecules, or some aspect of a mutant phenotype. With regard to substrates, the protein kinases may be roughly divided into two groups; those that phosphorylate tyrosine residues (protein tyrosine kinases, PTK) and those that phosphorylate serine or threonine residues (serine/threonine kinases, STK). A few protein kinases have dual specificity and phosphorylate threonine and tyrosine residues. Almost all kinases contain a similar 250–300 amino acid catalytic domain. The N-terminal domain, which contains subdomains I–IV, generally folds into a two-lobed structure, which binds and orients the ATP (or GTP) donor molecule. The larger C terminal lobe, which contains subdomains VI A-XI, binds the protein substrate and carries out the transfer of the gamma phosphate from ATP to the hydroxyl group of a serine, threonine, or tyrosine residue. Subdomain V spans the two lobes.

The kinases may be categorized into families by the different amino acid sequences (generally between 5 and 100 residues) located on either side of, or inserted into loops of, the kinase domain. These added amino acid sequences allow the regulation of each kinase as it recognizes and interacts with its target protein. The primary structure of the kinase domains is conserved and can be further subdivided into 11 subdomains. Each of the 11 subdomains contains specific residues and motifs or patterns of amino acids that are characteristic of that subdomain and are highly conserved (Hardie, G. and Hanks, S. (1995) *The Protein Kinase Facts Books*, Vol I:7–20 Academic Press, San Diego, Calif.).

The second messenger dependent protein kinases primarily mediate the effects of second messengers such as cyclic AMP (cAMP), cyclic GMP, inositol triphosphate, phosphatidylinositol, 3,4,5-triphosphate, cyclic-ADPribose, arachidonic acid, diacylglycerol and calcium-calmodulin. The cyclic-AMP dependent protein kinases (PKA) are important members of the STK family. Cyclic-AMP is an intracellular mediator of hormone action in all prokaryotic and animal cells that have been studied. Such hormone-induced cellular responses include thyroid hormone secretion, cortisol secretion, progesterone secretion, glycogen breakdown, bone resorption, and regulation of heart rate and force of heart muscle contraction. PKA is found in all animal cells and is thought to account for the effects of cyclic-AMP in most of these cells. Altered PKA expression is implicated in a variety of disorders and diseases including cancer, thyroid disorders, diabetes, atherosclerosis, and cardiovascular disease (Isselbacher, K. J. et al. (1994) *Harrison's Principles of Internal Medicine*, McGraw-Hill, New York, N.Y., pp. 416–431, 1887).

Calcium-calmodulin (CaM) dependent protein kinases are also members of STK family. Calmodulin is a calcium receptor that mediates many calcium regulated processes by binding to target proteins in response to the binding of calcium. The principle target protein in these processes is CaM dependent protein kinases. CaM-kinases are involved in regulation of smooth muscle contraction (MLC kinase), glycogen breakdown (phosphorylase kinase), and neurotransmission (CaM kinase I and CaM kinase II). CaM kinase I phosphorylates a variety of substrates including the neurotransmitter related proteins synapsin I and II, the gene transcription regulator, CREB, and the cystic fibrosis conductance regulator protein, CFTR (Haribabu, B. et al. (1995) *EMBO Journal* 14:3679–86). CaM II kinase also phosphorylates synapsin at different sites, and controls the synthesis of catecholamines in the brain through phosphorylation and activation of tyrosine hydroxylase. Many of the CaM kinases are activated by phosphorylation in addition to binding to CaM. The kinase may autophosphorylate itself, or be phosphorylated by another kinase as part of a "kinase cascade".

Another ligand-activated protein kinase is 5'-AMP-activated protein kinase (AMPK) (Gao, G. et al. (1996) *J. Biol Chem.* 15:8675–81). Mammalian AMPK is a regulator of fatty acid and sterol synthesis through phosphorylation of the enzymes acetyl-CoA carboxylase and hydroxymethylglutaryl-CoA reductase and mediates responses of these pathways to cellular stresses such as heat shock and depletion of glucose and ATP. AMPK is a heterotrimeric complex comprised of a catalytic alpha subunit and two non-catalytic beta and gamma subunits that are believed to regulate the activity of the alpha subunit. Subunits of AMPK have a much wider distribution in non-lipogenic tissues such as brain, heart, spleen, and lung than expected. This distribution suggests that its role may extend beyond regulation of lipid metabolism alone.

The mitogen-activated protein kinases (MAP) are also members of the STK family. MAP kinases also regulate intracellular signaling pathways. They mediate signal transduction from the cell surface to the nucleus via phosphorylation cascades. Several subgroups have been identified, and each manifests different substrate specificities and responds to distinct extracellular stimuli (Egan, S. E. and Weinberg, R. A. (1993) *Nature* 365:781–783). MAP kinase signaling pathways are present in mammalian cells as well as in yeast. The extracellular stimuli that activate mammalian pathways include epidermal growth factor (EGF), ultraviolet light, hyperosmolar medium, heat shock, endotoxic lipopolysaccharide (LPS), and pro-inflammatory cytokines such as tumor necrosis factor (TNF) and interleukin-1 (IL-1).

PRK (proliferation-related kinase) is a serum/cytokine inducible STK that is involved in regulation of the cell cycle and cell proliferation in human megakaroytic cells (Li, B. et al. (1996) *J. Biol. Chem.* 271:19402–8). PRK is related to the polo (derived from humans polo gene) family of STKs implicated in cell division. PRK is downregulated in lung tumor tissue and may be a proto-oncogene whose deregulated expression in normal tissue leads to oncogenic transformation. Altered MAP kinase expression is implicated in a variety of disease conditions including cancer, inflammation, immune disorders, and disorders affecting growth and development.

The cyclin-dependent protein kinases (CDKs) are another group of STKs that control the progression of cells through the cell cycle. Cyclins are small regulatory proteins that act by binding to and activating CDKs that then trigger various phases of the cell cycle by phosphorylating and activating selected proteins involved in the mitotic process. CDKs are unique in that they require multiple inputs to become activated. In addition to the binding of cyclin, CDK activation requires the phosphorylation of a specific threonine residue and the dephosphorylation of a specific tyrosine residue.

Protein tyrosine kinases, PTKs, specifically phosphorylate tyrosine residues on their target proteins and may be divided into transmembrane, receptor PTKs and nontransmembrane, non-receptor PTKs. Transmembrane protein-tyrosine kinases are receptors for most growth factors. Binding of growth factor to the receptor activates the transfer of a phosphate group from ATP to selected tyrosine side chains of the receptor and other specific proteins. Growth factors (GF) associated with receptor PTKs include; epidermal GF, platelet-derived GF, fibroblast GF, hepatocyte GF, insulin and insulin-like GFs, nerve GF, vascular endothelial GF, and macrophage colony stimulating factor.

Non-receptor PTKs lack transmembrane regions and, instead, form complexes with the intracellular regions of cell surface receptors. Such receptors that function through non-receptor PTKs include those for cytokines, hormones (growth hormone and prolactin) and antigen-specific receptors on T and B lymphocytes.

Many of these PTKs were first identified as the products of mutant oncogenes in cancer cells where their activation was no longer subject to normal cellular controls. In fact, about one third of the known oncogenes encode PTKs, and it is well known that cellular transformation (oncogenesis) is often accompanied by increased tyrosine phosphorylation activity (Carbonneau H and Tonks NK (1992) *Annu. Rev. Cell. Biol.* 8:463–93). Regulation of PTK activity may therefore be an important strategy in controlling some types of cancer.

Serine/Threonine Protein Kinases, Ellis-van Creveld syndrome (EvC) and Weyers acrodental dysostosis The novel human protein, and encoding gene, provided by the present invention is related to the family of serine/threonine protein kinases. The gene provided by the present invention shows a particularly high degree of similarity to the EVC gene, which is associated with Ellis-van Creveld syndrome (EvC) and Weyers acrodental dysostosis (Ruiz-Perez et al., Nat Genet 2000 March;24(3):283–6). The EVC gene encodes a 992 amino acid protein that is mutated in EvC and Weyers acrodental dysostosis. EvC and Weyers acrodental dysostosis may both be allelic conditions (Ruiz-Perez et al., Nat Genet 2000 March; 24(3):283–6). EvC is an autosomal recessive skeletal dysplasia. Individuals with EvC generally have short limbs and short ribs, postaxial polydactyly, dysplastic nails and teeth, and, commonly, congenital cardiac defects. Weyers acrodental dysostosis is an autosomal dominant disorder characterized by features that are similar to, but milder than, EvC (Ruiz-Perez et al., Nat Genet 2000 March;24(3):283–6).

The EVC gene overlaps the collapsin response mediator protein-1 (CRMP1) gene in the 3' UTR region and a portion of the coding region (Ruiz-Perez et al., Nat Genet 2000 March;24(3):283–6), suggesting a functional correlation. For a further review of CRMP1, see Hamajima et al., Gene 180: 157–163, 1996.

For a further review of EvC and Weyers acrodental dysostosis, see Digilio et al., Hum. Genet. 96: 251–253, 1996; McKusick, Nature Genet. 24: 203–204, 2000; McKusick et al., Bull. Johns Hopkins Hosp. 115: 306–336, 1964; Spranger et al., Clin. Genet. 47: 217–220, 1995; Roubicek et al., Clin. Genet. 26: 587–590, 1984; and Howard et al., Am. J. Hum. Genet. 61: 1405–1412, 1997.

Kinase proteins, particularly members of the serine/threonine protein kinase subfamily, are a major target for drug action and development. Accordingly, it is valuable to the field of pharmaceutical development to identify and characterize previously unknown members of this subfamily of kinase proteins. The present invention advances the state of the art by providing previously unidentified human kinase proteins that have homology to members of the serine/threonine protein kinase subfamily.

SUMMARY OF THE INVENTION

The present invention is based in part on the identification of amino acid sequences of human kinase peptides and proteins that are related to the serine/threonine protein kinase subfamily, as well as allelic variants and other mammalian orthologs thereof. These unique peptide sequences, and nucleic acid sequences that encode these peptides, can be used as models for the development of human therapeutic targets, aid in the identification of therapeutic proteins, and serve as targets for the development of human therapeutic agents that modulate kinase activity in cells and tissues that express the kinase. Experimental data as provided in FIG. 1 indicates expression in humans in prostate, lung, and whole brain.

DESCRIPTION OF THE FIGURE SHEETS

FIGS. 1A & 1B provide the nucleotide sequence of a cDNA molecule or transcript sequence that encodes the kinase protein of the present invention. (SEQ ID NO:1) In addition, structure and functional information is provided, such as ATG start, stop and tissue distribution, where available, that allows one to readily determine specific uses of inventions based on this molecular sequence. Experimental data as provided in FIG. 1 indicates expression in humans in prostate, lung, and whole brain.

FIGS. 2A–2C provide the predicted amino acid sequence of the kinase of the present invention. (SEQ ID NO:2) In addition structure and functional information such as protein family, function, and modification sites is provided where available, allowing one to readily determine specific uses of inventions based on this molecular sequence.

FIGS. 3A–3K provide genomic sequences that span the gene encoding the kinase protein of the present invention. (SEQ ID NO:3) In addition structure and functional information, such as intron/exon structure, promoter location, etc., is provided where available, allowing one to readily determine specific uses of inventions based on this molecular sequence. As indicated by the data presented inAs illustrated in FIG. 3, SNPs were identified at 17 different nucleotide positions.

DETAILED DESCRIPTION OF THE INVENTION

General Description

The present invention is based on the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a kinase protein or part of a kinase protein and are related to the serine/threonine protein kinase subfamily. Utilizing these sequences, additional genomic sequences were assembled and transcript and/or cDNA sequences were isolated and characterized. Based on this analysis, the present invention provides amino acid sequences of human kinase peptides and proteins that are related to the serine/threonine protein kinase subfamily, nucleic acid sequences in the form of transcript sequences, cDNA sequences and/or genomic sequences that encode these kinase peptides and proteins, nucleic acid variation (allelic information), tissue distribution of expression, and information about the closest art known protein/peptide/domain that has structural or sequence homology to the kinase of the present invention.

In addition to being previously unknown, the peptides that are provided in the present invention are selected based on their ability to be used for the development of commercially important products and services. Specifically, the present peptides are selected based on homology and/or structural relatedness to known kinase proteins of the serine/threonine protein kinase subfamily and the expression pattern observed. Experimental data as provided in FIG. 1 indicates expression in humans in prostate, lung, and whole brain. The art has clearly established the commercial importance of members of this family of proteins and proteins that have expression patterns similar to that of the present gene. Some of the more specific features of the peptides of the present invention, and the uses thereof, are described herein, particularly in the Background of the Invention and in the annotation provided in the Figures, and/or are known within the art for each of the known serine/threonine protein family or subfamily of kinase proteins.

Specific Embodiments

Peptide Molecules

The present invention provides nucleic acid sequences that encode protein molecules that have been identified as being members of the kinase family of proteins and are related to the serine/threonine protein kinase subfamily (protein sequences are provided in FIG. 2, transcript/cDNA sequences are provided in FIG. 1 and genomic sequences are provided in FIG. 3). The peptide sequences provided in FIG. 2, as well as the obvious variants described herein, particularly allelic variants as identified herein and using the information in FIG. 3, will be referred herein as the kinase peptides of the present invention, kinase peptides, or peptides/proteins of the present invention.

The present invention provides isolated peptide and protein molecules that consist of, consist essentially of, or comprise the amino acid sequences of the kinase peptides disclosed in the FIG. 2, (encoded by the nucleic acid molecule shown in FIG. 1, transcript/cDNA or FIG. 3, genomic sequence), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components (the features of an isolated nucleic acid molecule is discussed below).

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the kinase peptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated kinase peptide can be purified from cells that naturally express it, purified from cells that have been altered to express it (recombinant), or synthesized using known protein synthesis methods. Experimental data as provided in FIG. 1 indicates expression in humans in prostate, lung, and whole brain. For example, a nucleic acid molecule encoding the kinase peptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). The amino acid sequence of such a protein is provided in FIG. 2. A protein consists of an amino acid sequence when the amino acid sequence is the final amino acid sequence of the protein.

The present invention further provides proteins that consist essentially of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the kinase peptides of the present invention are the naturally occurring mature proteins. A brief description of how various types of these proteins can be made/isolated is provided below.

The kinase peptides of the present invention can be attached to heterologous sequences to form chimeric or fusion proteins. Such chimeric and fusion proteins comprise a kinase peptide operatively linked to a heterologous protein having an amino acid sequence not substantially homologous to the kinase peptide. "Operatively linked" indicates that the kinase peptide and the heterologous protein are fused in-frame. The heterologous protein can be fused to the N-terminus or C-terminus of the kinase peptide.

In some uses, the fusion protein does not affect the activity of the kinase peptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant kinase peptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., *Current Protocols in Molecular Biology*, 1992). Moreover, many expression vectors are commercially available that already encode a fusion moiety (e.g., a GST protein). A kinase peptide-encoding nucleic acid can be cloned into such an expression vector such that the fusion moiety is linked in-frame to the kinase peptide.

As mentioned above, the present invention also provides and enables obvious variants of the amino acid sequence of the proteins of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art-known techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the kinase peptides of the present invention. The degree of homology/identity present will be based primarily on whether the peptide is a functional variant or non-functional variant, the amount of divergence present in the paralog family and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part 1, Griffin, A.M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., *Nucleic Acids Res.* 12(1):387 (1984)) (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Myers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (*J. Mol. Biol.* 215:403–10 (1990)). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (*Nucleic Acids Res.* 25(17):3389–3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the kinase peptides of the present invention as well as being encoded by the same genetic locus as the kinase peptide provided herein. As indicated by the data presented in FIG. 3, the map position was determined to be on chromosome 10 by ePCR.

Allelic variants of a kinase peptide can readily be identified as being a human protein having a high degree (significant) of sequence homology/identity to at least a portion of the kinase peptide as well as being encoded by the same genetic locus as the kinase peptide provided herein. Genetic locus can readily be determined based on the genomic information provided in FIG. 3, such as the genomic sequence mapped to the reference human. As indicated by the data presented in FIG. 3, the map position was determined to be on chromosome 10 by ePCR. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a kinase peptide encoding nucleic acid molecule under stringent conditions as more fully described below.

FIG. 3 provides information on SNPs that have been found in the gene encoding the kinase protein of the present invention. SNPs were identified at 17 different nucleotide positions. SNPs such as these, particularly SNPs outside the ORF and in the first intron, may affect control/regulatory elements.

Paralogs of a kinase peptide can readily be identified as having some degree of significant sequence homology/identity to at least a portion of the kinase peptide, as being encoded by a gene from humans, and as having similar activity or function. Two proteins will typically be considered paralogs when the amino acid sequences are typically at least about 60% or greater, and more typically at least about 70% or greater homology through a given region or domain. Such paralogs will be encoded by a nucleic acid sequence that will hybridize to a kinase peptide encoding nucleic acid molecule under moderate to stringent conditions as more fully described below.

Orthologs of a kinase peptide can readily be identified as having some degree of significant sequence homology/identity to at least a portion of the kinase peptide as well as being encoded by a gene from another organism. Preferred orthologs will be isolated from mammals, preferably primates, for the development of human therapeutic targets and agents. Such orthologs will be encoded by a nucleic acid sequence that will hybridize to a kinase peptide encoding nucleic acid molecule under moderate to stringent conditions, as more fully described below, depending on the degree of relatedness of the two organisms yielding the proteins.

Non-naturally occurring variants of the kinase peptides of the present invention can readily be generated using recombinant techniques. Such variants include, but are not limited to deletions, additions and substitutions in the amino acid sequence of the kinase peptide. For example, one class of substitutions are conserved amino acid substitution. Such substitutions are those that substitute a given amino acid in a kinase peptide by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., *Science* 247:1306–1310 (1990).

Variant kinase peptides can be fully functional or can lack function in one or more activities, e.g. ability to bind substrate, ability to phosphorylate substrate, ability to mediate signaling, etc. Fully functional variants typically contain only conservative variation or variation in non-critical residues or in non-critical regions. FIG. 2 provides the result of protein analysis and can be used to identify critical domains/regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science* 244:1081–1085 (1989)), particularly using the results provided in FIG. 2. The latter procedure introduces single alanine mutations at every residue in the molecule. The resulting mutant molecules are then tested for biological activity such as kinase activity or in assays such as an in vitro proliferative activity. Sites that are critical for binding partner/substrate binding can also be determined by structural analysis such as crystallization, nuclear magnetic resonance or photoaffinity labeling (Smith et al., *J. Mol. Biol.* 224:899–904 (1992); de Vos et al. *Science* 255:306–312 (1992)).

The present invention further provides fragments of the kinase peptides, in addition to proteins and peptides that comprise and consist of such fragments, particularly those comprising the residues identified in FIG. 2. The fragments to which the invention pertains, however, are not to be construed as encompassing fragments that may be disclosed publicly prior to the present invention.

As used herein, a fragment comprises at least 8, 10, 12, 14, 16, or more contiguous amino acid residues from a kinase peptide. Such fragments can be chosen based on the ability to retain one or more of the biological activities of the kinase peptide or could be chosen for the ability to perform a function, e.g. bind a substrate or act as an immunogen. Particularly important fragments are biologically active fragments, peptides that are, for example, about 8 or more amino acids in length. Such fragments will typically comprise a domain or motif of the kinase peptide, e.g., active site, a transmembrane domain or a substrate-binding domain. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE analysis). The results of one such analysis are provided in FIG. 2.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in kinase peptides are described in basic texts, detailed monographs, and the research literature, and they are well known to those of skill in the art (some of these features are identified in FIG. 2).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties,* 2nd Ed., T. E. Creighton, W. H. Freeman and Company, New York (1993). Many detailed reviews are available on this subject, such as by Wold, F., *Posttranslational Covalent Modification of Proteins*, B. C. Johnson, Ed., Academic Press, New York 1–12 (1983); Seifter et al. (*Meth. Enzymol.* 182: 626–646 (1990)) and Rattan et al. (*Ann. N.Y. Acad. Sci.* 663:48–62 (1992)).

Accordingly, the kinase peptides of the present invention also encompass derivatives or analogs in which a substituted amino acid residue is not one encoded by the genetic code, in which a substituent group is included, in which the mature kinase peptide is fused with another compound, such as a compound to increase the half-life of the kinase peptide (for example, polyethylene glycol), or in which the additional amino acids are fused to the mature kinase peptide, such as a leader or secretory sequence or a sequence for purification of the mature kinase peptide or a pro-protein sequence.

Protein/Peptide Uses

The proteins of the present invention can be used in substantial and specific assays related to the functional information provided in the Figures; to raise antibodies or to elicit another immune response; as a reagent (including the labeled reagent) in assays designed to quantitatively determine levels of the protein (or its binding partner or ligand) in biological fluids; and as markers for tissues in which the corresponding protein is preferentially expressed (either constitutively or at a particular stage of tissue differentiation or development or in a disease state). Where the protein binds or potentially binds to another protein or ligand (such as, for example, in a kinase-effector protein interaction or kinase-ligand interaction), the protein can be used to identify the binding partner/ligand so as to develop a system to identify inhibitors of the binding interaction. Any or all of these uses are capable of being developed into reagent grade or kit format for commercialization as commercial products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The potential uses of the peptides of the present invention are based primarily on the source of the protein as well as the class/action of the protein. For example, kinases isolated from humans and their human/mammalian orthologs serve as targets for identifying agents for use in mammalian therapeutic applications, e.g. a human drug, particularly in modulating a biological or pathological response in a cell or tissue that expresses the kinase. Experimental data as provided in FIG. 1 indicates that kinase proteins of the present invention are expressed in humans in prostate, lung, and whole brain, as indicated by virtual northern blot analysis. In addition, PCR-based tissue screening panel indicates expression in whole brain. A large percentage of pharmaceutical agents are being developed that modulate the activity of kinase proteins, particularly members of the serine/threonine protein subfamily (see Background of the Invention). The structural and functional information provided in the Background and Figures provide specific and substantial uses for the molecules of the present invention, particularly in combination with the expression information provided in FIG. 1. Experimental data as provided in FIG. 1 indicates expression in humans in prostate, lung, and whole brain. Such uses can readily be determined using the information provided herein, that which is known in the art, and routine experimentation.

The proteins of the present invention (including variants and fragments that may have been disclosed prior to the present invention) are useful for biological assays related to kinases that are related to members of the serine/threonine protein subfamily. Such assays involve any of the known kinase functions or activities or properties useful for diagnosis and treatment of kinase-related conditions that are specific for the subfamily of kinases that the one of the present invention belongs to, particularly in cells and tissues that express the kinase. Experimental data as provided in FIG. 1 indicates that kinase proteins of the present invention are expressed in humans in prostate, lung, and whole brain, as indicated by virtual northern blot analysis. In addition, PCR-based tissue screening panel indicates expression in whole brain.

The proteins of the present invention are also useful in drug screening assays, in cell-based or cell-free systems.

Cell-based systems can be native, i.e., cells that normally express the kinase, as a biopsy or expanded in cell culture. Experimental data as provided in FIG. 1 indicates expression in humans in prostate, lung, and whole brain. In an alternate embodiment, cell-based assays involve recombinant host cells expressing the kinase protein.

The polypeptides can be used to identify compounds that modulate kinase activity of the protein in its natural state or an altered form that causes a specific disease or pathology associated with the kinase. Both the kinases of the present invention and appropriate variants and fragments can be used in high-throughput screens to assay candidate compounds for the ability to bind to the kinase. These compounds can be further screened against a functional kinase to determine the effect of the compound on the kinase activity. Further, these compounds can be tested in animal or invertebrate systems to determine activity/effectiveness. Compounds can be identified that activate (agonist) or inactivate (antagonist) the kinase to a desired degree.

Further, the proteins of the present invention can be used to screen a compound for the ability to stimulate or inhibit interaction between the kinase protein and a molecule that normally interacts with the kinase protein, e.g. a substrate or a component of the signal pathway that the kinase protein normally interacts (for example, another kinase). Such assays typically include the steps of combining the kinase protein with a candidate compound under conditions that allow the kinase protein, or fragment, to interact with the target molecule, and to detect the formation of a complex between the protein and the target or to detect the biochemical consequence of the interaction with the kinase protein and the target, such as any of the associated effects of signal transduction such as protein phosphorylation, cAMP turnover, and adenylate cyclase activation, etc.

Candidate compounds include, for example, 1) peptides such as soluble peptides, including Ig-tailed fusion peptides and members of random peptide libraries (see, e.g., Lam et al., *Nature* 354:82–84 (1991); Houghten et al., *Nature* 354:84–86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al., *Cell* 72:767–778 (1993)); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries).

One candidate compound is a soluble fragment of the receptor that competes for substrate binding. Other candidate compounds include mutant kinases or appropriate fragments containing mutations that affect kinase function and thus compete for substrate. Accordingly, a fragment that competes for substrate, for example with a higher affinity, or a fragment that binds substrate but does not allow release, is encompassed by the invention.

The invention further includes other end point assays to identify compounds that modulate (stimulate or inhibit) kinase activity. The assays typically involve an assay of events in the signal transduction pathway that indicate kinase activity. Thus, the phosphorylation of a substrate, activation of a protein, a change in the expression of genes that are up- or down-regulated in response to the kinase protein dependent signal cascade can be assayed.

Any of the biological or biochemical functions mediated by the kinase can be used as an endpoint assay. These include all of the biochemical or biochemical/biological events described herein, in the references cited herein, incorporated by reference for these endpoint assay targets, and other functions known to those of ordinary skill in the art or that can be readily identified using the information provided in the Figures, particularly FIG. 2. Specifically, a biological function of a cell or tissues that expresses the kinase can be assayed. Experimental data as provided in FIG. 1 indicates that kinase proteins of the present invention are expressed in humans in prostate, lung, and whole brain, as indicated by virtual northern blot analysis. In addition, PCR-based tissue screening panel indicates expression in whole brain.

Binding and/or activating compounds can also be screened by using chimeric kinase proteins in which the amino terminal extracellular domain, or parts thereof, the entire transmembrane domain or subregions, such as any of the seven transmembrane segments or any of the intracellular or extracellular loops and the carboxy terminal intracellular domain, or parts thereof, can be replaced by heterologous domains or subregions. For example, a substrate-binding region can be used that interacts with a different substrate then that which is recognized by the native kinase. Accordingly, a different set of signal transduction components is available as an end-point assay for activation. This allows for assays to be performed in other than the specific host cell from which the kinase is derived.

The proteins of the present invention are also useful in competition binding assays in methods designed to discover compounds that interact with the kinase (e.g. binding partners and/or ligands). Thus, a compound is exposed to a kinase polypeptide under conditions that allow the compound to bind or to otherwise interact with the polypeptide. Soluble kinase polypeptide is also added to the mixture. If the test compound interacts with the soluble kinase polypeptide, it decreases the amount of complex formed or activity from the kinase target. This type of assay is particularly useful in cases in which compounds are sought that interact with specific regions of the kinase. Thus, the soluble polypeptide that competes with the target kinase region is designed to contain peptide sequences corresponding to the region of interest.

To perform cell free drug screening assays, it is sometimes desirable to immobilize either the kinase protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of kinase-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a kinase-binding protein and a candidate compound are incubated in the kinase protein-presenting wells and the amount of complex trapped in the well can be quantitated. Methods for detecting such complexes, in addition to those described above for the GST-immobilized complexes, include immunodetection of complexes using antibodies reactive with the kinase protein target molecule, or which are reactive with kinase protein and compete with the target molecule, as well as enzyme-linked assays which rely on detecting an enzymatic activity associated with the target molecule.

Agents that modulate one of the kinases of the present invention can be identified using one or more of the above assays, alone or in combination. It is generally preferable to use a cell-based or cell free system first and then confirm activity in an animal or other model system. Such model systems are well known in the art and can readily be employed in this context.

Modulators of kinase protein activity identified according to these drug screening assays can be used to treat a subject with a disorder mediated by the kinase pathway, by treating cells or tissues that express the kinase. Experimental data as provided in FIG. 1 indicates expression in humans in prostate, lung, and whole brain. These methods of treatment include the steps of administering a modulator of kinase activity in a pharmaceutical composition to a subject in need of such treatment, the modulator being identified as described herein.

In yet another aspect of the invention, the kinase proteins can be used as "bait proteins" in a two-hybrid assay or three-hybrid assay (see, e.g., U.S. Pat. No. 5,283,317; Zervos et al. (1993) Cell 72:223–232; Madura et al. (1993) J. Biol. Chem. 268:12046–12054; Bartel et al. (1993) Biotechniques 14:920–924; Iwabuchi et al. (1993) Oncogene 8:1693–1696; and Brent WO94/10300), to identify other proteins, which bind to or interact with the kinase and are involved in kinase activity. Such kinase-binding proteins are also likely to be involved in the propagation of signals by the kinase proteins or kinase targets as, for example, downstream elements of a kinase-mediated signaling pathway. Alternatively, such kinase-binding proteins are likely to be kinase inhibitors.

The two-hybrid system is based on the modular nature of most transcription factors, which consist of separable DNA-binding and activation domains. Briefly, the assay utilizes two different DNA constructs. In one construct, the gene that codes for a kinase protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a kinase-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the kinase protein.

This invention further pertains to novel agents identified by the above-described screening assays. Accordingly, it is within the scope of this invention to further use an agent identified as described herein in an appropriate animal model. For example, an agent identified as described herein (e.g., a kinase-modulating agent, an antisense kinase nucleic acid molecule, a kinase-specific antibody, or a kinase-binding partner) can be used in an animal or other model to determine the efficacy, toxicity, or side effects of treatment with such an agent. Alternatively, an agent identified as described herein can be used in an animal or other model to determine the mechanism of action of such an agent. Furthermore, this invention pertains to uses of novel agents identified by the above-described screening assays for treatments as described herein.

The kinase proteins of the present invention are also useful to provide a target for diagnosing a disease or predisposition to disease mediated by the peptide. Accordingly, the invention provides methods for detecting the presence, or levels of, the protein (or encoding mRNA) in a cell, tissue, or organism. Experimental data as provided in FIG. 1 indicates expression in humans in prostate, lung, and whole brain. The method involves contacting a biological sample with a compound capable of interacting with the kinase protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells and fluids present within a subject.

The peptides of the present invention also provide targets for diagnosing active protein activity, disease, or predisposition to disease, in a patient having a variant peptide, particularly activities and conditions that are known for other members of the family of proteins to which the present one belongs. Thus, the peptide can be isolated from a biological sample and assayed for the presence of a genetic mutation that results in aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered kinase activity in cell-based or cell-free assay, alteration in substrate or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations and immunofluorescence using a detection reagent, such as an antibody or protein binding agent. Alternatively, the peptide can be detected in vivo in a subject by introducing into the subject a labeled anti-peptide antibody or other types of detection agent. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (*Clin. Exp. Pharmacol. Physiol.* 23(10–11):983–985 (1996)), and Linder, M. W. (*Clin. Chem.* 43(2): 254–266 (1997)). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymtes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the kinase protein in which one or more of the kinase functions in one population is different from those in another population. The peptides thus allow a target to ascertain a genetic predisposition that can affect treatment modality. Thus, in a ligand-based treatment, polymorphism may give rise to amino terminal extracellular domains and/or other substrate-binding regions that are more or less active in substrate binding, and kinase activation. Accordingly, substrate dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Experimental data as provided in FIG. 1 indicates expression in humans in prostate, lung, and whole brain. Accordingly, methods for treatment include the use of the kinase protein or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or F(ab')$_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods and as presented in the Figures.

Antibodies are preferably prepared from regions or discrete fragments of the kinase proteins. Antibodies can be prepared from any region of the peptide as described herein. However, preferred regions will include those involved in function/activity and/or kinase/binding partner interaction. FIG. 2 can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIG. 2).

Detection on an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Experimental data as provided in FIG. 1 indicates that kinase proteins of the present invention are expressed in humans in prostate, lung, and whole brain, as indicated by virtual northern blot analysis. In addition, PCR-based tissue screening panel indicates expression in whole brain. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development or progression of a biological condition. Antibody detection of circulating fragments of the full length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. Experimental data as provided in FIG. 1 indicates expression in humans in prostate, lung, and whole brain. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. Experimental data as provided in FIG. 1 indicates expression in humans in prostate, lung, and whole brain. The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the protein or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Experimental data as provided in FIG. 1 indicates expression in humans in prostate, lung, and whole brain. Thus, where a specific protein has been correlated with expression in a specific tissue, antibodies that are specific for this protein can be used to identify a tissue type.

The antibodies are also useful for inhibiting protein function, for example, blocking the binding of the kinase peptide to a binding partner such as a substrate. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. See FIG. 2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use. Such a kit can be supplied to detect a single protein or epitope or can be configured to detect one of a multitude of epitopes, such as in an antibody detection array. Arrays are described in detail below for nuleic acid arrays and similar methods have been developed for antibody arrays.

Nucleic Acid Molecules

The present invention further provides isolated nucleic acid molecules that encode a kinase peptide or protein of the present invention (cDNA, transcript and genomic sequence). Such nucleic acid molecules will consist of, consist essentially of, or comprise a nucleotide sequence that encodes one of the kinase peptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5 KB, 4 KB, 3 KB, 2 KB, or 1 KB or less, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a transcript/cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists of a nucleotide sequence when the nucleotide sequence is the complete nucleotide sequence of the nucleic acid molecule.

The present invention further provides nucleic acid molecules that consist essentially of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprises several hundred or more additional nucleotides. A brief description of how various types of these nucleic acid molecules can be readily made/isolated is provided below.

In FIGS. 1 and 3, both coding and non-coding sequences are provided. Because of the source of the present invention, humans genomic sequence (FIG. 3) and cDNA/transcript sequences (FIG. 1), the nucleic acid molecules in the Figures will contain genomic intronic sequences, 5' and 3' non-coding sequences, gene regulatory regions and non-coding intergenic sequences. In general such sequence features are either noted in FIGS. 1 and 3 or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the kinase peptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the nucleic acid molecule may be fused to a marker sequence encoding, for example, a peptide that facilitates purification.

Isolated nucleic acid molecules can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (antisense strand).

The invention further provides nucleic acid molecules that encode fragments of the peptides of the present invention as well as nucleic acid molecules that encode obvious variants of the kinase proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants can contain nucleotide substitutions, deletions, inversions and insertions. Variation can occur in either or both the coding and non-coding regions. The variations can produce both conservative and non-conservative amino acid substitutions.

The present invention further provides non-coding fragments of the nucleic acid molecules provided in FIGS. 1 and 3. Preferred non-coding fragments include, but are not limited to, promoter sequences, enhancer sequences, gene modulating sequences and gene termination sequences. Such fragments are useful in controlling heterologous gene expression and in developing screens to identify gene-modulating agents. A promoter can readily be identified as being 5' to the ATG start site in the genomic sequence provided in FIG. 3.

A fragment comprises a contiguous nucleotide sequence greater than 12 or more nucleotides. Further, a fragment could at least 30, 40, 50, 100, 250 or 500 nucleotides in length. The length of the fragment will be based on its intended use. For example, the fragment can encode epitope bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% or more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence. Allelic variants can readily be determined by genetic locus of the encoding gene. As indicated by the data presented in FIG. 3, the map position was determined to be on chromosome 10 by ePCR.

FIG. 3 provides information on SNPs that have been found in the gene encoding the kinase protein of the present invention. SNPs were identified at 17 different nucleotide positions. SNPs such as these, particularly SNPs outside the ORF and in the first intron, may affect control/regulatory elements.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. One example of stringent hybridization conditions are hybridization in 6× sodium chloride/sodium citrate (SSC) at about 45C, followed by one or more washes in 0.2×SSC, 0.1% SDS at 50–65C. Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptide described in FIG. 2 and to isolate cDNA and genomic clones that correspond to variants (alleles, orthologs, etc.) producing the same or related peptides shown in FIG. 2. As indicated by the data presented inAs illustrated in FIG. 3, SNPs were identified at 17 different nucleotide positions.

The probe can correspond to any sequence along the entire length of the nucleic acid molecules provided in the Figures. Accordingly, it could be derived from 5' noncoding regions, the coding region, and 3' noncoding regions. However, as discussed, fragments are not to be construed as encompassing fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods. As indicated by the data presented in FIG. 3, the map position was determined to be on chromosome 10 by ePCR.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for making vectors that express part, or all, of the peptides.

The nucleic acid molecules are also useful for constructing host cells expressing a part, or all, of the nucleic acid molecules and peptides.

The nucleic acid molecules are also useful for constructing transgenic animals expressing all, or a part, of the nucleic acid molecules and peptides.

The nucleic acid molecules are also useful as hybridization probes for determining the presence, level, form and distribution of nucleic acid expression. Experimental data as provided in FIG. 1 indicates that kinase proteins of the present invention are expressed in humans in prostate, lung, and whole brain, as indicated by virtual northern blot analysis. In addition, PCR-based tissue screening panel indicates expression in whole brain. Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism.

These uses are relevant for diagnosis of disorders involving an increase or decrease in kinase protein expression relative to normal results.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express a kinase protein, such as by measuring a level of a kinase-encoding nucleic acid in a sample of cells from a subject e.g., mRNA or genomic DNA, or determining if a kinase gene has been mutated. Experimental data as provided in FIG. 1 indicates that kinase proteins of the present invention are expressed in humans in prostate, lung, and whole brain, as indicated by virtual northern blot analysis. In addition, PCR-based tissue screening panel indicates expression in whole brain.

Nucleic acid expression assays are useful for drug screening to identify compounds that modulate kinase nucleic acid expression.

The invention thus provides a method for identifying a compound that can be used to treat a disorder associated with nucleic acid expression of the kinase gene, particularly biological and pathological processes that are mediated by the kinase in cells and tissues that express it. Experimental data as provided in FIG. 1 indicates expression in humans in prostate, lung, and whole brain. The method typically includes assaying the ability of the compound to modulate the expression of the kinase nucleic acid and thus identifying a compound that can be used to treat a disorder characterized by undesired kinase nucleic acid expression. The assays can be performed in cell-based and cell-free systems. Cell-based assays include cells naturally expressing the kinase nucleic acid or recombinant cells genetically engineered to express specific nucleic acid sequences.

The assay for kinase nucleic acid expression can involve direct assay of nucleic acid levels, such as mRNA levels, or on collateral compounds involved in the signal pathway. Further, the expression of genes that are up- or down-regulated in response to the kinase protein signal pathway can also be assayed. In this embodiment the regulatory regions of these genes can be operably linked to a reporter gene such as luciferase.

Thus, modulators of kinase gene expression can be identified in a method wherein a cell is contacted with a candidate compound and the expression of mRNA determined. The level of expression of kinase mRNA in the presence of the candidate compound is compared to the level of expression of kinase mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate kinase nucleic acid expression in cells and tissues that express the kinase. Experimental data as provided in FIG. 1 indicates that kinase proteins of the present invention are expressed in humans in prostate, lung, and whole brain, as indicated by virtual northern blot analysis. In addition, PCR-based tissue screening panel indicates expression in whole brain. Modulation includes both up-regulation (i.e. activation or agonization) or down-regulation (suppression or antagonization) or nucleic acid expression.

Alternatively, a modulator for kinase nucleic acid expression can be a small molecule or drug identified using the screening assays described herein as long as the drug or small molecule inhibits the kinase nucleic acid expression in the cells and tissues that express the protein. Experimental data as provided in FIG. 1 indicates expression in humans in prostate, lung, and whole brain.

The nucleic acid molecules are also useful for monitoring the effectiveness of modulating compounds on the expression or activity of the kinase gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in kinase nucleic acid expression, and particularly in qualitative changes that lead to pathology. The nucleic acid molecules can be used to detect mutations in kinase genes and gene expression products such as mRNA. The nucleic acid molecules can be used as hybridization probes to detect naturally occurring genetic mutations in the kinase gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the kinase gene associated with a dysfunction provides a diagnostic tool for an active disease or susceptibility to disease when the disease results from overexpression, underexpression, or altered expression of a kinase protein.

Individuals carrying mutations in the kinase gene can be detected at the nucleic acid level by a variety of techniques. FIG. 3 provides information on SNPs that have been found in the gene encoding the kinase protein of the present invention. SNPs were identified at 17 different nucleotide positions. SNPs such as these, particularly SNPs outside the ORF and in the first intron, may affect control/regulatory elements. As indicated by the data presented in FIG. 3, the map position was determined to be on chromosome 10 by ePCR. Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., *Science* 241:1077–1080 (1988); and Nakazawa et al., *PNAS* 91:360–364 (1994)), the latter of which can be particularly useful for detecting point mutations in the gene (see Abravaya et al., *Nucleic Acids Res.* 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a kinase gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method. Furthermore, sequence differences between a mutant kinase gene and a wild-type gene can be determined by direct DNA sequencing. A variety of automated sequencing procedures can be utilized when performing the diagnostic assays (Naeve, C. W., (1995) *Biotechniques* 19:448), including sequencing by mass spectrometry (see, e.g., PCT International Publication No. WO 94/16101; Cohen et al., *Adv. Chromatogr.* 36:127–162 (1996); and Griffin et al., *Appl. Biochem. Biotechnol.* 38:147–159 (1993)).

Other methods for detecting mutations in the gene include methods in which protection from cleavage agents is used to detect mismatched bases in RNA/RNA or RNA/DNA duplexes (Myers et al., *Science* 230:1242 (1985)); Cotton et al., *PNAS* 85:4397 (1988); Saleeba et al., *Meth. Enzymol.* 217:286–295 (1992)), electrophoretic mobility of mutant and wild type nucleic acid is compared (Orita et al., *PNAS* 86:2766 (1989); Cotton et al., *Mutat. Res.* 285:125–144 (1993); and Hayashi et al., *Genet. Anal. Tech. Appl.* 9:73–79 (1992)), and movement of mutant or wild-type fragments in polyacrylamide gels containing a gradient of denaturant is assayed using denaturing gradient gel electrophoresis (Myers et al., *Nature* 313:495 (1985)). Examples of other techniques for detecting point mutations include selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the kinase gene in an individual in order to select an appropriate compound or dosage regimen for treatment. FIG. 3 provides information on SNPs that have been found in the gene encoding the kinase protein of the present invention. SNPs were identified at 17 different nucleotide positions. SNPs such as these, particularly SNPs outside the ORF and in the first intron, may affect control/regulatory elements.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control kinase gene expression in cells, tissues, and organisms. A DNA antisense nucleic acid molecule is designed to be complementary to a region of the gene involved in transcription, preventing transcription and hence production of kinase protein. An antisense RNA or DNA nucleic acid molecule would hybridize to the mRNA and thus block translation of mRNA into kinase protein.

Alternatively, a class of antisense molecules can be used to inactivate mRNA in order to decrease expression of kinase nucleic acid. Accordingly, these molecules can treat a disorder characterized by abnormal or undesired kinase nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the kinase protein, such as substrate binding.

The nucleic acid molecules also provide vectors for gene therapy in patients containing cells that are aberrant in kinase gene expression. Thus, recombinant cells, which include the patient's cells that have been engineered ex vivo and returned to the patient, are introduced into an individual where the cells produce the desired kinase protein to treat the individual.

The invention also encompasses kits for detecting the presence of a kinase nucleic acid in a biological sample. Experimental data as provided in FIG. 1 indicates that kinase proteins of the present invention are expressed in humans in prostate, lung, and whole brain, as indicated by virtual northern blot analysis. In addition, PCR-based tissue screening panel indicates expression in whole brain. For example, the kit can comprise reagents such as a labeled or labelable nucleic acid or agent capable of detecting kinase nucleic acid in a biological sample; means for determining the amount of kinase nucleic acid in the sample; and means for comparing the amount of kinase nucleic acid in the sample with a standard. The compound or agent can be packaged in a suitable container. The kit can further comprise instructions for using the kit to detect kinase protein mRNA or DNA.

Nucleic Acid Arrays

The present invention further provides nucleic acid detection kits, such as arrays or microarrays of nucleic acid molecules that are based on the sequence information provided in FIGS. 1 and 3 (SEQ ID NOS:1 and 3).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application WO95/11995 (Chee et al.), Lockhart, D. J. et al (1996; Nat. Biotech. 14: 1675–1680) and Schena, M. et al. (1996; Proc. Natl. Acad. Sci. 93: 10614–10619), all of which are incorporated herein in their entirety by reference. In other embodiments, such arrays are produced by the methods described by Brown et al, U.S. Pat. No. 5,807,522.

The microarray or detection kit is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray or detection kit, it may be preferable to use oligonucleotides that are only 7–20 nucleotides in length. The microarray or detection kit may contain oligonucleotides that cover the known 5', or 3', sequence, sequential oligonucleotides which cover the full length sequence; or unique oligonucleotides selected from particular areas along the length of the sequence. Polynucleotides used in the microarray or detection kit may be oligonucleotides that are specific to a gene or genes of interest.

In order to produce oligonucleotides to a known sequence for a microarray or detection kit, the gene(s) of interest (or an ORF identified from the contigs of the present invention) is typically examined using a computer algorithm which starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray or detection kit. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one million which lends itself to the efficient use of commercially available instrumentation.

In order to conduct sample analysis using a microarray or detection kit, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray or detection kit so that the probe sequences hybridize to complementary oligonucleotides of the microarray or detection kit. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray or detection kit. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large-scale correlation studies on the sequences, expression patterns, mutations, variants, or polymorphisms among samples.

Using such arrays, the present invention provides methods to identify the expression of the kinase proteins/peptides of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention and or alleles of the kinase gene of the present invention. FIG. 3 provides information on SNPs that have been found in the gene encoding the kinase protein of the present invention. SNPs were identified at 17 different nucleotide positions. SNPs such as these, particularly SNPs outside the ORF and in the first intron, may affect control/regulatory elements.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the Human genome disclosed herein. Examples of such assays can be found in Chard, T, *An Introduction to Radioimmunoassay and Related Techniques*, Elsevier Science Publishers, Amsterdam, The Netherlands (1986); Bullock, G. R. et al., *Techniques in Immunocytochemistry*, Academic Press, Orlando, Fla. Vol. 1 (1982), Vol. 2 (1983), Vol. 3 (1985); Tijssen, P., *Practice and Theory of Enzyme Immunoassays: Laboratory Techniques in Biochemistry and Molecular Biology*, Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily be adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the Human genome disclosed herein; and (b) one or more other containers comprising one or more of the following: wash reagents, reagents capable of detecting presence of a bound nucleic acid.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified kinase gene of the present invention can be routinely identified using the sequence information disclosed herein can be readily incorporated into one of the established kit formats which are well known in the art, particularly expression arrays.

Vectors/Host Cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extra-chromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in prokaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual.* 2nd. ed., Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning: A Laboratory Manual.* 2nd. ed., Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli*, Streptomyces, and *Salmonella typhimurium.* Eukaryotic cells include, but are not limited to, yeast, insect cells such as Drosophila, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enterokinase. Typical fusion expression vectors include pGEX (Smith et al., *Gene* 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301–315 (1988)) and pET 11d (Studier et al., *Gene Expression Technology: Methods in Enzymology* 185:60–89 (1990)).

Recombinant protein expression can be maximized in host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990)119–128). Alternatively, the sequence of the nucleic acid molecule of interest can be altered to provide preferential codon usage for a specific host cell, for example *E. coli.* (Wada et al., *Nucleic Acids Res.* 20:2111–2118 (1992)).

The nucleic acid molecules can also be expressed by expression vectors that are operative in yeast. Examples of vectors for expression in yeast e.g., *S. cerevisiae* include pYepSec1 (Baldari, et al., *EMBO J.* 6:229–234 (1987)), pMFa (Kurjan et al., *Cell* 30:933–943(1982)), pJRY88 (Schultz et al, *Gene* 54:113–123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf 9 cells) include the pAc series (Smith et al., *Mol. Cell Biol* 3:2156–2165 (1983)) and the pVL series (Lucklow et al., *Virology* 170:31–39 (1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaufman et al., *EMBO J* 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance propagation or expression of the nucleic acid molecules described herein. These are found for example in Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual*. 2nd, ed., Cold Spring Harbor Laboratory, Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, which is difficult to achieve with multi-transmembrane domain containing proteins such as kinases, appropriate secretion signals are incorporated into the vector. The signal sequence can be endogenous to the peptides or heterologous to these peptides.

Where the peptide is not secreted into the medium, which is typically the case with kinases, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of Vectors and Host Cells

The recombinant host cells expressing the peptides described herein have a variety of uses. First, the cells are useful for producing a kinase protein or peptide that can be further purified to produce desired amounts of kinase protein or fragments. Thus, host cells containing expression vectors are useful for peptide production.

Host cells are also useful for conducting cell-based assays involving the kinase protein or kinase protein fragments, such as those described above as well as other formats known in the art. Thus, a recombinant host cell expressing a native kinase protein is useful for assaying compounds that stimulate or inhibit kinase protein function.

Host cells are also useful for identifying kinase protein mutants in which these functions are affected. If the mutants naturally occur and give rise to a pathology, host cells containing the mutations are useful to assay compounds that have a desired effect on the mutant kinase protein (for example, stimulating or inhibiting function) which may not be indicated by their effect on the native kinase protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a kinase protein and identifying and evaluating modulators of kinase protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the kinase protein nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence (s) can be operably linked to the transgene to direct expression of the kinase protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems that allow for regulated expression of the transgene. One example of such a system is the cre/loxP recombinase system of bacteriophage P1. For a description of the cre/loxP recombinase system, see, e.g., Lakso et al. *PNAS* 89:6232–6236 (1992). Another example of a recombinase system is the FLP recombinase system of *S. cerevisiae* (O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter $G_0$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect substrate binding, kinase protein activation, and signal transduction, may not be evident from in vitro cell-free or cell-based assays. Accordingly, it is useful to provide non-human transgenic animals to assay in vivo kinase protein function, including substrate interaction, the effect of specific mutant kinase proteins on kinase protein function and substrate interaction, and the effect of chimeric kinase proteins. It is also possible to assess the effect of null mutations, that is, mutations that substantially or completely eliminate one or more kinase protein functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

That which is claimed is:

1. An isolated nucleic acid molecule consisting of a nucleotide sequence selected from the group consisting of:
   (a) a nucleotide sequence that encodes an amino acid sequence consisting of SEQ ID NO:2;
   (b) a nucleotide sequence consisting of SEQ ID NO:1;
   (c) a nucleotide sequence consisting of SEQ ID NO:3; and
   (d) a nucleotide sequence that is completely complementary to a nucleotide sequence of (a), (b), or (c).

2. A nucleic acid vector comprising the nucleic acid molecule of claim 1.

3. An isolated host cell containing the vector of claim 2.

4. A process for producing a polypeptide comprising culturing the host cell of claim 3 under conditions sufficient for the production of said polypeptide, and recovering said polypeptide.

5. An isolated polynucleotide consisting of the nucleotide sequence set forth in SEQ ID NO:1.

6. An isolated polynucleotide consisting of the nucleotide sequence set forth in SEQ ID NO:3.

7. A vector according to claim 2, wherein said vector is selected from the group consisting of a plasmid, a virus, and a bacteriophage.

8. A vector according to claim 2, wherein said isolated nucleic acid molecule is inserted into said vector in proper orientation and correct reading frame such that a polypeptide having an amino acid sequence consisting of SEQ ID NO:2 is expressed by a cell transformed with said vector.

9. A vector according to claim 8, wherein said isolated nucleic acid molecule is operatively linked to a promoter sequence.

10. An isolated nucleic acid molecule comprising a nucleotide sequence selected from the group consisting of:
    (a) a transcript/cDNA sequence that encodes an amino acid sequence consisting of SEQ ID NO:2;
    (b) SEQ ID NO:1;
    (c) nucleotides 193–1299 of SEQ ID NO:1; and
    (d) a nucleotide sequence that is completely complementary to a nucleotide sequence of (a), (b), or (c).

11. A nucleic acid vector comprising the nucleic acid molecule of claim 10.

12. An isolated host cell containing the vector of claim 11.

13. A process for producing a polypeptide comprising culturing the host cell of claim 12 under conditions sufficient for the production of said polypeptide, and recovering said polypeptide.

14. A vector according to claim 11, wherein said vector is selected from the group consisting of a plasmid, a virus, and a bacteriophage.

15. A vector according to claim 11, wherein said isolated nucleic acid molecule is inserted into said vector in proper orientation and correct reading frame such that a polypeptide having an amino acid sequence consisting of SEQ ID NO:2 is expressed by a cell transformed with said vector.

16. A vector according to claim 15, wherein said isolated nucleic acid molecule is operatively linked to a promoter sequence.

17. An isolated nucleic acid molecule encoding a serine/threonine kinase, wherein the nucleic acid molecule consists of a nucleotide sequence selected from the group consisting of:
    (a) a nucleotide sequence that encodes a polypeptide consisting of an amino acid sequence having at least 99% sequence identity to SEQ ID NO:2;
    (b) a nucleotide sequence having at least 99% sequence identity to SEQ ID NO:1; and
    (c) a nucleotide sequence having at least 99% sequence identity to SEQ ID NO:3.

18. An isolated nucleic acid molecule consisting of a nucleotide sequence that is completely complementary to a nucleotide sequence of claim 17.

19. An isolated polynucleotide comprising the nucleotide sequence of SEQ ID NO:1.

* * * * *